US012269865B2

(12) United States Patent
Ouzounov et al.

(10) Patent No.: US 12,269,865 B2
(45) Date of Patent: Apr. 8, 2025

(54) RECOMBINANT ELASTIN AND PRODUCTION THEREOF

(71) Applicant: Geltor, Inc., San Leandro, CA (US)

(72) Inventors: Nikolay Ouzounov, San Ramon, CA (US); Tanya Eliason, Oakland, CA (US)

(73) Assignee: Geltor, Inc., San Leandro, CA (US)

( * ) Notice: Subject to any disclaimer, the term of this patent is extended or adjusted under 35 U.S.C. 154(b) by 0 days.

(21) Appl. No.: 17/493,598

(22) Filed: Oct. 4, 2021

(65) Prior Publication Data

US 2022/0127333 A1 Apr. 28, 2022

Related U.S. Application Data

(63) Continuation of application No. 16/844,226, filed on Apr. 9, 2020, now Pat. No. 11,168,126.

(60) Provisional application No. 62/889,397, filed on Aug. 20, 2019, provisional application No. 62/833,415, filed on Apr. 12, 2019.

(51) Int. Cl.
*C07K 14/78* (2006.01)
*A61K 8/64* (2006.01)
*A61Q 19/00* (2006.01)

(52) U.S. Cl.
CPC ............. *C07K 14/78* (2013.01); *A61K 8/64* (2013.01); *A61Q 19/00* (2013.01)

(58) Field of Classification Search
CPC .......... C07K 14/78; A61Q 19/00; A61K 8/64
See application file for complete search history.

(56) References Cited

U.S. PATENT DOCUMENTS

| | | | |
|---|---|---|---|
| 4,515,893 A | 5/1985 | Kung et al. | |
| 4,816,397 A | 3/1989 | Boss et al. | |
| 4,816,567 A | 3/1989 | Cabilly et al. | |
| 4,946,778 A | 8/1990 | Ladner et al. | |
| 5,091,313 A | 2/1992 | Chang | |
| 5,602,183 A | 2/1997 | Martin et al. | |
| 5,622,700 A | 4/1997 | Jardieu et al. | |
| 5,672,347 A | 9/1997 | Aggarwal et al. | |
| 5,693,762 A | 12/1997 | Queen et al. | |
| 5,714,338 A | 2/1998 | Wai Fei et al. | |
| 5,721,108 A | 2/1998 | Robinson et al. | |
| 5,725,856 A | 3/1998 | Hudziak et al. | |
| 5,736,137 A | 4/1998 | Anderson et al. | |
| 5,969,106 A * | 10/1999 | Rothstein ........ | A61K 8/64 424/193.1 |
| 6,413,742 B1 | 7/2002 | Olsen et al. | |
| 6,428,978 B1 | 8/2002 | Olsen et al. | |
| 6,617,431 B1 | 9/2003 | Gruber et al. | |
| 6,653,450 B1 | 11/2003 | Berg et al. | |
| 6,682,760 B2 | 1/2004 | Noff et al. | |
| 6,903,200 B1 | 6/2005 | Chou et al. | |
| 6,992,172 B1 | 1/2006 | Chang et al. | |
| 7,125,837 B1 | 10/2006 | Keating et al. | |
| 7,229,788 B1 | 6/2007 | Weiss | |
| 7,495,076 B2 | 2/2009 | Gu et al. | |
| 7,700,126 B2 | 4/2010 | Ng et al. | |
| 7,754,447 B2 | 7/2010 | Glover et al. | |
| 7,759,090 B2 | 7/2010 | Chou et al. | |
| 7,803,577 B2 | 9/2010 | Weiss | |
| 7,932,053 B2 | 4/2011 | Bank et al. | |
| 7,932,353 B2 | 4/2011 | Van Es et al. | |
| 8,252,553 B2 | 8/2012 | Hook et al. | |
| 8,507,652 B2 | 8/2013 | Da Cruz | |
| 8,618,250 B2 | 12/2013 | Russell et al. | |
| 8,759,487 B2 | 6/2014 | Shoseyov et al. | |
| 8,889,626 B2 | 11/2014 | Lin et al. | |
| 8,956,632 B2 | 2/2015 | Boutros | |
| 9,040,484 B2 | 5/2015 | Marinkovich et al. | |
| 9,072,724 B2 | 7/2015 | Hausmanns et al. | |
| 9,156,950 B2 | 10/2015 | Garralda et al. | |
| 9,328,154 B2 | 5/2016 | Chilkoti | |
| 9,382,310 B2 | 7/2016 | Mirochnitchenko et al. | |
| 9,591,853 B2 | 3/2017 | Belgorodsky et al. | |
| 9,675,635 B2 | 6/2017 | Minatelli et al. | |
| 9,676,837 B2 | 6/2017 | Viswanathan et al. | |
| 9,725,498 B2 | 8/2017 | Russell et al. | |
| 9,962,582 B2 | 5/2018 | Antku | |
| 10,053,501 B2 | 8/2018 | Ramshaw et al. | |
| 10,155,793 B2 | 12/2018 | Ramshaw et al. | |
| 10,232,008 B1 | 3/2019 | Moran | |

(Continued)

FOREIGN PATENT DOCUMENTS

| CN | 1403479 A | 3/2003 |
|---|---|---|
| CN | 101311193 A | 11/2008 |

(Continued)

OTHER PUBLICATIONS

Homayouni-Tabrizi et al., Cytotoxic and antioxidant capacity of camel milk peptides: Effects of isolated peptide on superoxide dismutase and catalase gene expression, Journal of food and drug analysis, 2017, 25, pp. 567-575.*
EBI Accession No. USPOP:ABL21271. Database Accession No. ABL21271. EMBL-EBI. Retrieved Feb. 14, 2023 at https://www.ebi.ac.uk/Tools/dbfetch/. One page.
EBI Accession No. USPOP:ABU27708. Database Accession No. ABU27708. EMBL-EBI. Retrieved Feb. 14, 2023 at https://www.ebi.ac.uk/Tools/dbfetch/. 2 pages.
EP20787564.2 Extended European Search Report dated Dec. 23, 2022.
Amino acid sequence of SEQ ID No. 572 in US20130237486A1, pp. 1-2, accessed Jul. 15, 2020 at URL: http://seqdata.uspto.gov/?pageRequest=viewSequenceDocID=US20130237486A1&seqID=572. United States Patent and Trademark Office Publication Site for Issued and Published Sequences (PSIPS).

(Continued)

*Primary Examiner* — Li N Komatsu
(74) *Attorney, Agent, or Firm* — Rikki A. Hullinger; Casimir Jones, S.C.

(57) ABSTRACT

This disclosure provides non-naturally occurring truncated elastin molecules. The non-naturally occurring truncated elastin may improve the firmness, elasticity, brightness, hydration, tactile texture, and/or visual texture of skin. The non-naturally occurring truncated elastin may reduce degradation of the extracellular matrix.

29 Claims, 6 Drawing Sheets

Specification includes a Sequence Listing.

(56) References Cited

U.S. PATENT DOCUMENTS

| | | | |
|---|---|---|---|
| 10,358,464 B2 | 7/2019 | Hook et al. | |
| 10,941,406 B2 | 3/2021 | Ouzounov | |
| 11,028,148 B2 | 6/2021 | Ouzounov et al. | |
| 11,041,015 B2 | 6/2021 | Ouzounov et al. | |
| 11,168,126 B2 | 11/2021 | Ouzounov et al. | |
| 11,174,300 B2 | 11/2021 | Ouzounov et al. | |
| 11,180,541 B2 | 11/2021 | Ouzounov et al. | |
| 11,214,609 B2 | 1/2022 | Ouzounov et al. | |
| 11,332,505 B2 | 5/2022 | Ouzounov et al. | |
| 2002/0132753 A1 | 9/2002 | Rosen et al. | |
| 2008/0200409 A1 | 8/2008 | Wilson et al. | |
| 2010/0209940 A1* | 8/2010 | Veidal | G01N 33/6893 435/7.1 |
| 2013/0078209 A1 | 3/2013 | Yu et al. | |
| 2013/0237486 A1 | 9/2013 | Bella | |
| 2014/0200531 A1 | 7/2014 | Jordan et al. | |
| 2014/0309401 A1 | 10/2014 | Hayashida et al. | |
| 2015/0150764 A1 | 6/2015 | Pinsky | |
| 2016/0130315 A1 | 5/2016 | Kim et al. | |
| 2016/0215018 A1 | 7/2016 | Yang et al. | |
| 2018/0282776 A1 | 10/2018 | Douchin et al. | |
| 2019/0276515 A1 | 9/2019 | Bruno-Bonnet et al. | |
| 2020/0009184 A1 | 1/2020 | Akthakul et al. | |
| 2020/0184381 A1 | 6/2020 | Persikov et al. | |
| 2020/0247874 A1 | 8/2020 | Ouzounov et al. | |
| 2020/0255497 A1 | 8/2020 | Ouzounov et al. | |
| 2022/0332775 A1 | 10/2022 | Ouzounov et al. | |

FOREIGN PATENT DOCUMENTS

| | | |
|---|---|---|
| CN | 101311196 A | 11/2008 |
| CN | 101374859 A | 2/2009 |
| CN | 102471769 A | 5/2012 |
| CN | 103897057 A | 7/2014 |
| CN | 104667335 A | 6/2015 |
| CN | 109350555 A | 2/2019 |
| EP | 0036776 A2 | 9/1981 |
| EP | 0535446 A1 | 4/1993 |
| EP | 0420937 B1 | 11/1994 |
| EP | 1323820 A2 | 7/2003 |
| EP | 2941277 B1 | 9/2018 |
| EP | 3395860 A1 | 10/2018 |
| JP | 2003137807 A | 5/2003 |
| JP | 2003516730 A | 5/2003 |
| JP | 2003277399 A | 10/2003 |
| JP | 2006151847 A | 6/2006 |
| JP | 2013095708 A | 5/2013 |
| JP | 2016124798 A | 7/2016 |
| JP | 2017523780 A | 8/2017 |
| JP | 2020535812 A | 12/2020 |
| KR | 20020059719 A | 7/2002 |
| KR | 20160093739 A | 8/2016 |
| KR | 20180056237 A | 5/2018 |
| KR | 20190024916 A | 3/2019 |
| WO | WO-9304173 A1 | 3/1993 |
| WO | WO-9404690 A1 | 3/1994 |
| WO | WO-9519181 A1 | 7/1995 |
| WO | WO-9523865 A1 | 9/1995 |
| WO | WO-9630046 A1 | 10/1996 |
| WO | WO-9640210 A1 | 12/1996 |
| WO | WO-9726912 A2 | 7/1997 |
| WO | WO-9738710 A1 | 10/1997 |
| WO | WO-9806248 A2 | 2/1998 |
| WO | WO-9823761 A1 | 6/1998 |
| WO | WO-9845331 A2 | 10/1998 |
| WO | WO-9851793 A1 | 11/1998 |
| WO | WO-9903886 A1 | 1/1999 |
| WO | WO-0009018 A1 | 2/2000 |
| WO | WO-0075348 A1 | 12/2000 |
| WO | WO-0140309 A2 | 6/2001 |
| WO | WO-2004056312 A2 | 7/2004 |
| WO | WO-2005021772 A1 | 3/2005 |
| WO | WO-2005094868 A1 | 10/2005 |
| WO | WO-2008000445 A1 | 1/2008 |
| WO | WO-2009134511 A1 | 11/2009 |
| WO | WO-2010071938 A1 | 7/2010 |
| WO | WO-2011008904 A1 | 1/2011 |
| WO | WO-2012063088 A2 | 5/2012 |
| WO | WO-2015012682 A2 | 1/2015 |
| WO | WO-2015012683 A1 | 1/2015 |
| WO | WO-2016004334 A1 | 1/2016 |
| WO | WO-2017083398 A1 | 5/2017 |
| WO | WO-2017125585 A2 | 7/2017 |
| WO | WO-2017156418 A1 | 9/2017 |
| WO | WO-2017160636 A1 | 9/2017 |
| WO | WO-2017125585 A9 | 10/2017 |
| WO | WO-2017172994 A1 | 10/2017 |
| WO | WO-2017206326 A1 | 12/2017 |
| WO | WO-2018014453 A1 | 1/2018 |
| WO | WO-2018041684 A1 | 3/2018 |
| WO | WO-2018078276 A1 | 5/2018 |
| WO | WO-2018119530 A1 | 7/2018 |
| WO | WO-2018144093 A2 | 8/2018 |
| WO | WO-2019023555 A1 | 1/2019 |
| WO | WO-2019046943 A1 | 3/2019 |
| WO | WO-2019068018 A2 | 4/2019 |
| WO | WO-2019077312 A1 | 4/2019 |
| WO | WO-2019099561 A1 | 5/2019 |
| WO | WO-2019166418 A1 | 9/2019 |
| WO | WO-2020205848 A1 | 10/2020 |
| WO | WO-2020210440 A1 | 10/2020 |
| WO | WO-2022072696 A1 | 4/2022 |

OTHER PUBLICATIONS

Anonymous, "ColF1—Fibrillar collagen—Podocoryna carnera (Hydrozoan)—colF1 gene & protein" (Jan. 1, 1998), XP055541622, Retrieved from the Internet: URL:https://www.uniportorg/uniport/076966#entry_information [retrieved on Jan. 14, 2019].

Blast search results for SEQ ID No. 76, pp. 1-24 (accessed Jun. 28, 2021).

Bochicchio et al., Investigating the Role of (2S,4r)-4-Hydroxyproline in Elastin Model Peptides. Biomacromolecules 14: 4278-4288 (2013).

Bornert, Olivier et al. "Analysis of the functional consequences of targeted exon deletion in COL7A1 reveals prospects for dystrophic epidermolysis bullosa therapy", Molecular Therapy. Jul. 1, 2016;24(7):1302-11.

Bornhorst JA, Falke JJ. [16] Purification of proteins using polyhistidine affinity tags. In Methods in enzymology Jan. 1, 2000 (vol. 326, pp. 245-254). Academic Press.

Brown-Augsburger et al., Identification of an Elastin Cross-linking Domain that Joins Three Peptide Chains. Journal of Biological Chemistry 270(30): 17778-17783 (1995).

Cayley, D. Scott, et al., "Biophysical characterization of changes in amounts and activity of *Escherichia coli* cell and compartment water and turgor pressure in response to osmotic stress", Biophysical Journal, (Apr. 2000), 78(4):1748-1764.

Chandrakasan et al. Preparation of intact monomeric collagen from rat tail tendon and skin and the structure of the nonhelical ends in solution. J Biol Chem. Oct. 10, 1976;251(19):6062-7.

Chou, M-Y, et al., "Genomic organization and characterization of the human type XXI collagen (COL21A1) gene", Genomics. Mar. 1, 2002;79(3):395-401.

Chu et al. Multiexon deletion in an osteogenesis imperfecta variant with increased type III collagen mRNA. J Biol Chem. Jan. 25, 1985;260(2):691-4.

Collagen, type XXI, alpha 1, isoform CRA_e [*Homo sapiens*], from https://www.ncbi.nlm.nih.gov/protein/EAX04452.1?report=genbank&log$=protalign&blast_rank=1&RID=GVNGXK5R01 R, p. 1-3, accessed Jul. 14, 2020. Record created Dec. 18, 2006.

Definition of Serum by Merriam-Webster, from https://www.merriam-webster.com/dictionary/serum, pp. 1-12, accessed Apr. 18, 2019.

Dinh et al. Using superfolder green fluorescent protein for periplasmic protein localization studies. J Bacteriol 193(18):4984-4987 (Sep. 2011). Epub Jul. 15, 2011. doi: 10.1128/JB.00315-11.

Drumm et al. Genetic Variation and Clinical Heterogeneity in Cystic Fibrosis. Annu Rev Pathol. 2012; 7: 267-282. Published online Oct. 17, 2011. doi: 10.1146/annurev-pathol-011811-120900.

(56) References Cited

OTHER PUBLICATIONS

Dulbecco's Modified Eagle Medium (DMEM). Product Information. Product Code: AT068. HiMedia Laboratories Pvt Ltd., Mumbai, India. 2011. 2 pages.

EP20186437.8 Extended European Search Report dated Jan. 22, 2021.

Fleischmajer et al. Rotary shadowing of collagen monomers, oligomers, and fibrils during tendon fibrillogenesis. J Histochem Cytochem. Jan. 1991;39(1):51-8.

GenBank Accession No. AJ009690. Version No. AJ009690.1. Podocoryne carnea mRNA for fibrillar collagen, partial. Record created Jul. 30, 1988. 2 pages. Retrieved Mar. 26, 2020 at URL: https://www.ncbi.nlm.nih.gov/nucleotide/3355656?report=genbanklog$=nuclalign&blast_rank=1&RID=TSYP7CMV014.

GenBank Accession No. CAA08789. Version No. CAA08789.1. fibrillar collagen, partial [Podocoryna carnea]. Record created Mar. 9, 1999. 2 pages. Retrieved Apr. 28, 2020 at URL: https://www.ncbi.nlm.nih.gov/protein/4379341?report=genbank&log$=protalign&blast_rank=1&RID=T1N9ZEUW014.

GenBank Accession No. XP_016874317. Version No. XP_016874317.1. collagen alpha-1(II) chain isoform X1 [*Homo sapiens*]. Record created Jun. 6, 2016. 3 pages. Accessed Jun. 18, 2020 at URL: https://www.ncbi.nlm.nih.gov/protein/XP_016874317.1?report=genbank&log$=protalign&blast_rank=11&RID=ER8N7H11014.

Gortz, H.—D et al., "Changes in Fine Structure and Polypeptide Pattern during Development of Holospora obtuse, a bacterium Infecting the macronucleus of Paramecium caudatum", Journal of Bacteriology, (Oct. 1, 1990), 172(10):5664-5669, XP055373233, Retrieved from the Internet: URL: https://www.ncbi.nlm.nih.gov/pmc/articles/PMC526880/pdf/jbacter00164-0156.pdf, [retrieved May 16, 2017].

Grosso et al. PGAIPG, a Repeated Hexapeptide of Bovine Tropoelastin, Is a Ligand for the 67-kDa Bovine Elastin Receptor. Matrix. Mar. 1993;13(2):157-64. doi: 10.1016/s0934-8832(11)80074-0.

Gumpert et al. Characteristic properties and biological significance of stable protoplast type L-forms. In Protoplasts, Lecture Proceedings of the 6th International Protoplast Symposium: Basel. Experientia 1983, 46(suppl):227-241.

Haworth, R.S. et al., "Uncoupler resistance in *E. coli* Tuv and Cuv is due to the exclusion of uncoupler by the outer membrane", Biochim Biophys Acta., (Aug. 9, 1990), 1019(1):67-72, XP023349580, ISBN: 0005-2728, DOI: 10.1016/0005-2728(90)90125-N [retrieved on Aug. 9, 1990]. Abstract only.

Hoischen et al. Lipid and fatty acid composition of cytoplasmic membranes from Streptomyces hygroscopicus and its stable protoplast-type L form. J Bacteriol 179(11):3430-3436 (Jun. 1997).

Hong et al., Fibrillar Type I Collagen Enhances the Differentiation and Proliferation of Myofibroblasts by Lowering alpha2beta1 Integrin Expression in Cardiac Fibrosis. Biomed Res Int. 2017; 2017: 1790808. Published online Jan. 30, 2017. doi: 10.1155/2017/1790808. 11 pages.

International Preliminary Report on Patentability, dated Oct. 2, 2018, for International Patent Application No. PCT/US2017/024857.

International Search Report and Written Opinion of the Searching Authority for International Patent Application No. PCT/US2017/024857, dated May 31, 2017.

International Search Report and Written Opinion of the Searching Authority for International Patent Application No. PCT/US2018/053601, dated Apr. 10, 2019.

Joly et al. Chapter 20: Practical Applications for Periplasmic Protein Accumulation, in The Periplasm, ed. Ehrmann, M., ASM Press, Washington D.C., pp. 345-360 (2007).

Krapf et al. Deciphering the aggregation mechanism of bacteria (Shewanella oneidensis MR1) in the presence of polyethyleneimine: Effects of the exopolymeric superstructure and polymer molecular weight. Colloids Surf B Biointerfaces. Mar. 1, 2016;139:285-93. doi: 10.1016/j.colsurfb.2015.12.015. Epub Dec. 8, 2015.

Kuzan et al. An Estimation of the Biological Properties of Fish Collagen in an Experimental In Vitro Study. Adv Clin Exp Med. May-Jun. 2015;24(3):385-92. doi: 10.17219/acem/31704.

Lucas et al. A molecular, morphometric and mechanical comparison of the structural elements of byssus from Mytilus edulis and Mytilus galloprovincialis. J Exp Biol. Jun. 2002;205(Pt 12):1807-17.

Luo et al. Collagen-like peptides and peptide-polymer conjugates in the design of assembled materials. Eur Polym J. Oct. 2013; 49(10): 2998-3009. doi: 10.1016/j.eurpolymj.2013.05.013. Available online Jun. 4, 2013.

Paul-Dauphin et al. Bias and precision in visual analogue scales: a randomized controlled trial. Am J Epidemiol. Nov. 15, 1999;150(10):1117-27.

PCT/US2020/025934 International Search Report and Written Opinion dated Jul. 2, 2020.

PCT/US2020/027399 International Search Report and Written Opinion dated Jun. 26, 2020.

Peptidecutter of SEQ ID No. 4 in Chou et al., from https://web.expasy.org/cgi-bin/peptide_cutter/peptidecutter.ol, pp. 1-8, accessed Jan. 29, 2021.

Phosphate buffered saline. Protocols Online (Oct. 3, 2016). Retrieved Aug. 7, 2020 from URL: https://www.protocolsonline.com/recipes/phosphate-buffered-saline-pbs/. 3 pages.

Pilizota, Teuta and J. W. Shaevitz, "Fast, Multiphase Volume Adaptation to Hyperosmotic Shock by *Escherichia coli*", PLoS ONE, (Apr. 2012), 7(4): e35205. https://doi.org/10.1371/journal.pone.0035205.

Protease cleavage of SEQ ID No. 61 in WO 2019/068018A2, from ExPASy—PeptideCutter, SIB Swiss Institute of Bioinformatics, accessed Oct. 15, 2020 at URL: https://web.expasy.org/cgi-bin/peptide_cutter/peptidecutter.p1, pp. 1-2.

Ramshaw, John A. M., et al., "Gly-XY tripeptide frequencies in collagen: a context for host—guest triple-helical peptides", Journal of structural biology. Jan. 1, 1998;122(1-2):86-91.

Rodriguez et al. Collagen: A Review on Its Sources and Potential Cosmetic Applications. J Cosmet Dermatol. Feb. 2018;17(1):20-26. doi: 10.1111/jocd.12450. Epub Nov. 16, 2017.

Schmid, V. et al., "The extracellular matrix (mesoglea) of hydrozoan jellyfish and its ability to support cell adhesion and spreading", In Hydrobiologia Jun. 1, 1991 (vol. 216, No. 1, pp. 3-10). Kluwer Academic Publishers.

Schrader et al., Elastin is heterogeneously cross-linked. J Biol Chem 293(39): 15107-15119 (2018).

Sewing et al. Jellyfish collagen matrices conserve the chondrogenic phenotype in two-and three-dimensional collagen matrices. J Tissue Eng Regen Med. Mar. 2017;11(3):916-925. doi: 10.1002/term.1993. Epub Jan. 29, 2015.

Shigemura et al. Effect of Prolyl-hydroxyproline (Pro-Hyp), a food-derived collagen peptide in human blood, on growth of fibroblasts from mouse skin. J Agric Food Chem. Jan. 28, 2009;57(2):444-9. doi: 10.1021/jf802785h.

Shin et al. Enhancement of the Tumor Penetration of Monoclonal Antibody by Fusion of a Neuropilin-Targeting Peptide Improves the Antitumor Efficacy. Mol Cancer Ther 13(3):651-661, with supplementary information pp. 1-27 (Mar. 2014).

Teale et al., Ultraviolet fluorescence of the aromatic amino acids. Biochem J. 65(3):476-482 (1957).

Tomaro-Duchesneau et al. Microencapsulation for the Therapeutic Delivery of Drugs, Live Mammalian and Bacterial Cells, and Other Biopharmaceutics: Current Status and Future Directions. J Pharm (Cairo) 2013:103527 (2013). Published online Dec. 4, 2012. doi: 10.1155/2013/103527.

Tris buffer, from http://cshprotocols.cshlp.org/content/2011/2/pdb.rec12394.full, pp. 1-2, accessed Nov. 16, 2020.

Turczynski et al., Targeted Exon Skipping Restores Type VII Collagen Expression and Anchoring Fibril Formation in an In Vivo RDEB Model. Journal of Investigative Dermatology 136: 2387-2395 (2016).

U.S. Appl. No. 16/144,914 Final Office Action dated Feb. 5, 2021.

U.S. Appl. No. 16/839,035 Non-Final Office Action dated Jul. 7, 2021.

U.S. Appl. No. 16/839,035 Non-Final Office Action dated Nov. 27, 2020.

(56) References Cited

OTHER PUBLICATIONS

U.S. Appl. No. 16/839,042 Final Office Action dated Dec. 3, 2020.
U.S. Appl. No. 16/839,042 Notice of Allowance dated Apr. 16, 2021.
U.S. Appl. No. 16/839,042 Notice of Allowance dated Feb. 8, 2021.
U.S. Appl. No. 16/839,044 Final Office Action dated Dec. 10, 2020.
U.S. Appl. No. 16/839,047 Notice of Allowance dated Feb. 23, 2021.
U.S. Appl. No. 16/144,914 Notice of Allowance dated Sep. 1, 2021.
U.S. Appl. No. 16/144,914 Office Action dated Jul. 10, 2020.
U.S. Appl. No. 16/839,035 Office Action dated Jul. 24, 2020.
U.S. Appl. No. 16/839,042 Office Action dated Aug. 24, 2020.
U.S. Appl. No. 16/839,044 Office Action dated Aug. 7, 2020.
U.S. Appl. No. 16/839,047 Office Action dated Oct. 21, 2020.
Water, from http://www.biology-online.org/dictionary/Water, accessed Apr. 24, 2014, 3 pages.
What Is Sorbic Acid? From https://www.healthline.com/health/food-nutrition/what-is-sorbic-acid, accessed Sep. 9, 2019, 3 pages.
Willing et al. Heterozygosity for a large deletion in the alpha 2(I) collagen gene has a dramatic effect on type I collagen secretion and produces perinatal lethal osteogenesis imperfecta. J Biol Chem. Jun. 15, 1988;263(17):8398-404.
Woodley et al., Intravenously Injected Recombinant Human Type VII Collagen Homes to Skin Wounds and Restores Skin Integrity of Dystrophic Epidermolysis Bullosa. Journal of Investigative Dermatology 133: 1910-1913 (2013).
Yampolsky et al. The Exchangeability of Amino Acids in Proteins. Genetics. Aug. 2005; 170(4): 1459-1472. doi: 10.1534/genetics.104.039107.
Zhuang et al. Effects of Collagen and Collagen Hydrolysate From Jellyfish (Rhopilema Esculentum) on Mice Skin Photoaging Induced by UV Irradiation. J Food Sci. Aug. 2009;74(6):H183-8. doi: 10.1111/j.1750-3841.2009.01236.x.
Co-pending U.S. Appl. No. 17/491,228, inventors Brightman; Laura et al., filed Sep. 30, 2021.
Co-pending U.S. Appl. No. 17/532,978, inventors Ouzounov; Nikolay et al., filed Nov. 22, 2021.
U.S. Appl. No. 16/844,226 Final Office Action dated Feb. 4, 2021.
U.S. Appl. No. 16/839,035 Notice of Allowance dated Oct. 26, 2021.
U.S. Appl. No. 16/844,226 Notice of Allowance dated Sep. 16, 2021.
U.S. Appl. No. 16/844,226 Office Action dated Oct. 29, 2020.
Co-pending U.S. Appl. No. 18/191,556, inventors Co; Julia et al., filed Mar. 28, 2023.
EP20781827.9 Extended European Search Report dated Jun. 6, 2023.
Katayama et al. Regulation of extracellular matrix production by chemically synthesized subfragments of type I collagen carboxy propeptide. Biochemistry 1991, 30, 7097-7104.
PCT/US2021/052966 International Search Report and Written Opinion dated Dec. 10, 2021.
U.S. Appl. No. 17/532,978 Office Action dated May 25, 2023.
U.S. Appl. No. 17/532,978 Office Action dated Dec. 22, 2023.
Zhuang, et al. Effects of collagen and collagen hydrolysate from jellyfish umbrella on histological and immunity changes of mice photoaging. Nutrients. vol. 5 (2013): 223-233.
GenBank Accession No. EAX04451. Version No. EAX04451.1. collagen, type XXI, alpha 1, isoform CRA_d [*Homo sapiens*]. Record created Dec. 18, 2006. 2 pages. Retrieved Mar. 22, 2024 at URL: https://www.ncbi.nlm.nih.gov/protein/EAX04451.1?report=genbank&log$=protalign&blast_rank=2&RID=WP6DGNX7013.
GenBank Accession No. EAX04452. Version No. EAX04452.1. collagen, type XXI, alpha 1, isoform CRA_e [*Homo sapiens*]. Record created Dec. 18, 2006. 2 pages. Retrieved Mar. 22, 2024 at URL: https://www.ncbi.nlm.nih.gov/protein/EAX04452.1?report=genbank&log$=protalign&blast_rank=1&RID=WP6DGNX7013.
GenBank Accession No. NP_001305681. Version No. NP_001305681.1. collagen alpha-1(XXI) chain isoform b precursor [*Homo sapiens*]. Record created Jan. 14, 2016. 3 pages. Retrieved Mar. 22, 2024 at URL: https://www.ncbi.nlm.nih.gov/protein/NP_001305681.1/.
Green fluorescent protein. Wikipedia. [Website] Retrieved Mar. 22, 2024 at URL: https://en.wikipedia.org/wiki/Green_fluorescent_protein. 10 pages.
Lee, Jan-Hun, et al. Development of Screening Method for the Soluble Recombinant Protein using β-Lactamase as a Fusion Partner. Korean Chem. Eng. Res. 47, 5 (2009): 624-629. With English abstract.
Pai et al. Topical peptides as cosmeceuticals. Indian Journal of Dermatology, Venereology, and Leprology, vol. 83, Issue 1, pp. 9-18 (Jan.-Feb. 2017).

\* cited by examiner

A   B

RECOMBINANT ELASTIN AND PRODUCTION THEREOF

CROSS-REFERENCE

This application is a continuation of U.S. patent application Ser. No. 16/844,226, filed Apr. 9, 2020, now U.S. Pat. No. 11,168,126, issued Nov. 9, 2021, which claims the benefit of U.S. Provisional Application Nos. 62/833,415, filed Apr. 12, 2019, and 62/889,397, filed Aug. 20, 2019, which applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Sep. 29, 2021, is named 57607_706_301_SL.txt and is 44,966 bytes in size.

BACKGROUND

Elastin is an elastic protein that is crucial for the proper functioning of arteries, lung, tendons, ligament, skin, and other tissue. Elastin provides the tissues with the ability to stretch and return to their original shape. The protein tropoelastin is the building block of elastin. In contrast to other structural proteins, like collagen, that include a family of genes, there is one tropoelastin gene in humans. When the gene encoding tropoelastin is expressed, the single tropoelastin gene is spliced to produce different forms of the tropoelastin protein. Many tropoelastin molecules associate together to form elastin.

The structure of natural elastin is similar to collagen with an amino acid sequence rich in glycine and proline. The individual polypeptide strands are composed of repeating triplet amino acid sequences designated as GLY-X-Y interspersed with strings of alanines that provide flexibility. X and Y can be any amino acid and the first amino acid is glycine. The amino acids proline and hydroxyproline are found in high concentrations in elastin. Elastin is normally covalently crosslinked to other elastin peptides by the action of lysyl oxidase enzyme. Because of the extensive crosslinking of elastin peptides, it is difficult to extract elastins from animal tissues.

Certain domains of elastin may act as signaling domains for intracellular communication. In addition, certain elastin domains may function as binding domains for polypeptides and other biological molecules. Degradation products of elastin have been demonstrated to activate cellular processes such as phagocytosis. These cell interacting domains are interspaced with stretches of alanine that produce the flexible stretchy structure that is characteristic of elastin. The stretches of alanine are also rich in lysines that, in tissues, get converted to allysine by lysyl oxidase and crosslink together into a fishing net-like structure, making extraction of elastin from animal tissues very difficult which requires the breaking down of the elastin molecule for release. Due to this difficult extraction process, commercially available elastins are only 3-5 kDa in size.

In human natural elastin, there are two sections of the molecule, each of which contains three contiguous repeats of VGVAPG (SEQ ID NO: 1), namely, VGVAPGVGVAPGVGVAPG (SEQ ID NO: 3). The amino acid sequence VGVAPG (SEQ ID NO: 1) has been reported to promote extracellular matrix degradation.

SUMMARY

In one aspect, a non-naturally occurring polypeptide is provided consisting of an amino acid sequence having at least 80% sequence identity to an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence having at least 85% sequence identity to an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence having at least 90% sequence identity to an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence having at least 95% sequence identity to an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide of consists of an amino acid sequence having at least 98% sequence identity to an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19, or a truncate thereof (e.g., a polypeptide having at least 50, 60, 70, 80, 90, 100, 110, 120, 130, 140, or 150 amino acids); and one or more selected from the group consisting of: a secretion tag, a histidine tag, a fluorescent protein, and a protease cleavage site. In some cases, the non-naturally occurring polypeptide consists of an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19; and one or more selected from the group consisting of: a secretion tag, a histidine tag, a fluorescent protein, and a protease cleavage site. In some cases, the non-naturally occurring polypeptide consists of an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19, or a truncate thereof (e.g., a polypeptide having at least 50, 60, 70, 80, 90, 100, 110, 120, 130, 140, or 150 amino acids). In some cases, the non-naturally occurring polypeptide consists of an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19. In some cases, the secretion tag is DsbA. In some cases, the non-naturally occurring polypeptide is a recombinant polypeptide.

In another aspect, a composition is provided comprising between 0.001% and 30% w/w of a non-naturally occurring polypeptide of any one of the preceding. In some cases, the composition comprises between 0.001% and 1% w/w of the non-naturally occurring polypeptide, between 0.001% and 0.05% w/w of the non-naturally occurring polypeptide, between 0.001% and 0.03% w/w of the non-naturally occurring polypeptide, between 0.001% and 0.02% w/w of the non-naturally occurring polypeptide, between 0.001% and 0.01% w/w of the non-naturally occurring polypeptide, between 0.005% and 0.1% w/w of the non-naturally occurring polypeptide, between 0.005% and 0.03% w/w of the non-naturally occurring polypeptide, between 0.005% and 0.02% w/w of the non-naturally occurring polypeptide, or between 0.005% and 0.01% w/w of the non-naturally occurring polypeptide. In some cases, the composition is capable of stimulating growth of fibroblast cells, stimulating synthesis of tropoelastin, decreasing formation of thymine-thymine (TT) dimer formation, or any combination thereof. In some cases, the composition is formulated for topical application. In some cases, the composition comprises one or more of a topical carrier and a preservative. In some cases, the topical carrier is selected from the group consisting of: water, oil glycereth-8 esters, glycerin, coconut alkanes, hydroxyethyl acrylate/sodium acryloyldimethyl taurate copolymer, pentylene glycol, disodium EDTA, caprylyl glycol, chlorphenesin, phenoxyethanol, liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, and cyclopentasiloxane. In some cases, the preservative is selected from the group consisting of: tocopherol, diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, methyl paraben, sorbic acid, GERMABEN® II, rosemary extract, and EDTA. In some cases, the composition is a cosmetic.

In another aspect, a method of treating the skin of a subject is provided, the method comprising administering to the skin of a subject a composition of any one of the preceding, thereby treating the skin of the subject. In some cases, the treating comprises decreasing skin damage, promoting the repair of damaged skin, protecting the skin against UV damage, increasing viability of skin cells, protection of skin cells from the effects of urban dust exposure, or any combination thereof. In some cases, viability of fibroblast cells, keratinocyte cells, or both, present in the skin of the subject is increased. In some cases, synthesis of procollagen by fibroblast cells present in the skin of the subject is increased. In some cases, expression of one or more anti-oxidant gene by keratinocytes present in the skin of the subject is increased. In some cases, the one or more anti-oxidant gene is selected from the group consisting of: SOD2, GPX2, GPX4, GSTK1, GSTZ1, GSTA4, GSTM2, CCS, GPX1, GLRX, PRDX5, PRDX6, and PRDX2. In some cases, expression of one or more pro-apoptotic genes by keratinocytes present in the skin of the subject is decreased. In some cases, the one or more pro-apoptotic gene is selected from the group consisting of: APAF1, BAK1, CASP7, CASP8, FADD, MCL1, and MET. In some cases, production of inflammatory cytokines by a keratinocyte present in the skin of the subject is decreased. In some cases, the inflammatory cytokine is IL-1α. In some cases, viability of keratinocytes present in the skin of the subject is increased.

In yet another aspect, a polynucleotide is provided encoding a non-naturally occurring polypeptide according to any one of the preceding. In some cases, the polynucleotide is contained within a vector. In some cases, the polynucleotide comprises a nucleic acid sequence comprising at least 80% sequence identity to a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16, and SEQ ID NO: 18. In some cases, the polynucleotide comprises a nucleic acid sequence comprising at least 85% sequence identity to a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16, and SEQ ID NO: 18. In some cases, the polynucleotide comprises a nucleic acid sequence comprising at least 90% sequence identity to a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16, and SEQ ID NO: 18. In some cases, the polynucleotide comprises a nucleic acid sequence comprising at least 95% sequence identity to a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16, and SEQ ID NO: 18. In some cases, the polynucleotide comprises a nucleic acid sequence comprising at least 98% sequence identity to a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16, and SEQ ID NO: 18. In some cases, the polynucleotide comprises a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16, and SEQ ID NO: 18. In some cases, the polynucleotide further comprises a nucleic acid sequence encoding one or more of a secretion tag, a histidine tag, a fluorescent protein, and a protease cleavage site. In some cases, the nucleic acid sequence is codon-optimized for expression in a host cell.

In yet another aspect, a recombinant cell is provided comprising at least one copy of a heterologous nucleic acid sequence encoding a non-naturally occurring polypeptide of any one of the preceding. In some cases, the recombinant cell is a microbial cell. In some cases, the microbial cell is a bacterial cell. In some cases, the bacterial cell is of the species *Escherichia coli*. In some cases, the heterologous nucleic acid sequence has at least 95% sequence identity to a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16; and SEQ ID NO: 18. In some cases, the heterologous nucleic acid sequence comprises a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16; and SEQ ID NO: 18. In some cases, the heterologous nucleic acid sequence is codon-optimized for expression in a cell. In some cases, the recombinant cell is capable of secreting the non-naturally occurring polypeptide extracellularly.

In yet another aspect, a composition is provided comprising a recombinant cell of any one of the preceding, and a culture media comprising a non-naturally occurring polypeptide of any one of the preceding.

In yet another aspect, a method of producing a non-naturally occurring polypeptide is provided, the method comprising: a) incubating a recombinant cell of any one of the preceding in a culture media, wherein the recombinant cell secretes the recombinant polypeptide into the culture media; b) collecting the culture media comprising the recombinant polypeptide secreted thereto; and c) purifying the recombinant polypeptide from the culture media.

In another aspect, a non-naturally occurring polypeptide is provided consisting of an amino acid sequence having at least 80% sequence identity to an amino acid sequence according to SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence having at least 85% sequence identity to an amino acid sequence according to SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence having at least 90% sequence identity to an amino acid sequence according to SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence having at least 95% sequence identity to an amino acid sequence according to SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence having at least 98% sequence identity to an amino acid sequence according to SEQ ID NO: 19, or a truncate thereof (e.g., a polypeptide having at least 50, 60, 70, 80, 90, 100, 110, 120, 130, 140, or 150 amino acids); and optionally, one or more selected from the group consisting of: a secretion tag, a histidine tag, a fluorescent protein, and a protease cleavage site. In some cases, the non-naturally occurring polypeptide consists of an amino acid sequence according to SEQ ID NO: 19, or a truncate thereof (e.g., a polypeptide having at least 50, 60, 70, 80, 90, 100, 110, 120, 130, 140, or 150 amino acids); and one or more selected from the group consisting of: a secretion tag, a histidine tag, a fluorescent protein, and a protease cleavage site. In some cases, the non-naturally occurring polypeptide consists of an amino acid sequence according to SEQ ID NO: 19, or a truncate thereof (e.g., a polypeptide having at least 50, 60, 70, 80, 90, 100, 110, 120, 130, 140, or 150 amino acids). In some cases, the non-naturally occurring polypeptide consists of an amino acid sequence according to SEQ ID NO: 19. In some cases, the secretion tag is DsbA. In some cases, the non-naturally occurring polypeptide is a recombinant polypeptide. In another aspect, a composition is provided comprising between 0.001% and 30% w/w of the non-naturally occurring polypeptide. In some cases, the composition comprises between 0.001% and 1% w/w of the non-naturally occurring polypeptide, between 0.001% and 0.05% w/w of the non-naturally occurring polypeptide, between 0.001% and 0.03% w/w of the non-naturally occurring polypeptide, between 0.001% and 0.02% w/w of the non-naturally occurring polypeptide, between 0.001% and 0.01% w/w of the non-naturally occurring polypeptide, between 0.005% and 0.1% w/w of the non-naturally occurring polypeptide, between 0.005% and 0.03% w/w of the non-naturally occurring polypeptide, between 0.005% and 0.02% w/w of the non-naturally occurring polypeptide, or between 0.005% and 0.01% w/w of the non-naturally occurring polypeptide. In some cases, the composition is capable of one or more selected from the group consisting of: stimulating growth of fibroblast cells, increasing viability of fibroblast cells or keratinocyte cells, stimulating synthesis of tropoelastin, stimulating synthesis of procollagen, stimulating expression of one or more anti-oxidant gene, reducing expression of one or more pro-apoptotic gene, decreasing production of one or more inflammatory cytokines, and decreasing formation of thymine-thymine (TT) dimer formation. In some cases, the composition is formulated for topical application. In some cases, the composition comprises one or more of a topical carrier and a preservative. In some cases, the topical carrier is selected from the group consisting of: water, oil glycereth-8 esters, glycerin, coconut alkanes, hydroxyethyl acrylate/sodium acryloyldimethyl taurate copolymer, pentylene glycol, disodium EDTA, caprylyl glycol, chlorphenesin, phenoxyethanol, liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, and cyclopentasiloxane. In some cases, the preservative is selected from the group consisting of: tocopherol, diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, methyl paraben, sorbic acid, Germaben II, rosemary extract, and EDTA. In some cases, the composition is a cosmetic. In another aspect, a recombinant cell is provided comprising at least one copy of a heterologous nucleic acid sequence encoding the non-naturally occurring polypeptide. In some cases, the recombinant cell is of the species *Escherichia coli*.

In certain embodiments herein are various polypeptides, compositions comprising such polypeptides, and methods of using such polypeptides and/or compositions thereof. In certain embodiments, such polypeptides comprise non-naturally occurring and/or recombinant polypeptides, such as comprising one or more amino acid sequence that is truncated relative to a naturally occurring elastin (e.g., a full-length elastin), such as a naturally occurring elastin described herein. In certain instances, such polypeptides are described herein as a "truncated elastin". In specific embodiments, the polypeptide comprises one or more (e.g., two or more) truncated amino acid sequence of a naturally occurring human elastin.

In one aspect, a non-naturally occurring full length or a non-naturally occurring truncated human elastin molecule is provided. In one embodiment, the truncated human elastin molecule is produced by a host cell. The non-naturally occurring elastin may be a human elastin. In an embodiment, the non-naturally occurring elastin may be a full-length or a truncated elastin (e.g., relative to a naturally occurring and/or a full-length elastin).

In one embodiment, a non-naturally occurring polypeptide (e.g., a truncated human elastin) is provided, wherein the non-naturally occurring polypeptide does not comprise one or more contiguous amino acid sequences, and wherein each of the one or more contiguous amino acid sequences has the sequence of VGVAPG (SEQ ID NO: 1). In another embodiment, the non-naturally occurring polypeptide (e.g., a truncated human elastin) does not comprise two or more of the contiguous amino acid sequence VGVAPG (SEQ ID NO: 1). For example, in an embodiment, the non-naturally occurring polypeptide (e.g., a truncated human elastin) does not comprise the amino acid sequence VGVAPGVGVAPG (SEQ ID NO: 2) or the non-naturally occurring polypeptide (e.g., a truncated human elastin) does not comprise the amino acid sequence VGVAPGVGVAPGVGVAPG (SEQ ID NO: 3). In some cases, a non-naturally occurring polypeptide described herein (e.g., a truncated human elastin) reduces extracellular matrix degradation or does not promote or cause extracellular matrix degradation.

In various aspects, a non-naturally occurring polypeptide disclosed herein (e.g., a truncated human elastin) may have a molecular weight of between 1 kDa and 60 kDa, between 5 kDa and 55 kDa, between 5 kDa and 50 kDa, between 5 kDa and 45 kDa, between 5 kDa and 40 kDa, between 5 kDa and 35 kDa, between 5 kDa and 30 kDa, between 5 kDa and 25 kDa, between 5 kDa and 20 kDa, between 5 kDa and 15 kDa, between 5 kDa and 10 kDa, between 10 kDa and 40 kDa, between 10 kDa and 35 kDa, between 10 kDa and 30 kDa, between 10 kDa and 25 kDa, or between 10 kDa and 20 kDa.

In yet another embodiment, a non-naturally occurring polypeptide (e.g., a truncated human elastin) is provided, wherein the non-naturally occurring polypeptide is truncated at the C-terminal end relative to a naturally occurring and/or full-length human elastin, the N-terminal end relative to a naturally occurring and/or full-length human elastin, internally truncated relative to a naturally occurring and/or full-length human elastin, or truncated at both the C-terminal end and the N-terminal end relative to a naturally occurring and/or full-length human elastin. In some cases, a non-naturally occurring polypeptide described herein comprises a truncation (e.g., at the N-terminal end, at the C-terminal end, and/or an internal truncation) relative to SEQ ID NO: 20.

A non-naturally occurring polypeptide described herein (e.g., a truncated human elastin) may be between 10 and 700 amino acids in length, between 10 and 600 amino acids in length, between 10 and 500 amino acids in length, between 10 and 400 amino acids in length, between 10 and 300 amino acids in length, between 10 and 200 amino acids in length, between 10 and 100 amino acids in length, between 10 and 50 amino acids in length, between 50 and 800 amino acids in length, between 50 and 700 amino acids in length, between 50 and 600 amino acids in length, between 50 and 500 amino acids in length, between 50 and 400 amino acids in length, between 50 and 300 amino acids in length, between 50 and 200 amino acids in length, or between 50 and 100 amino acids in length. In another embodiment, a non-naturally occurring polypeptide described herein (e.g., a truncated human elastin) may be a molecule that is shorter by at least 1, 5, 10, 20, 50, 100, or more amino acids than full-length human tropoelastin or a full-length human elastin.

In specific embodiments, a non-naturally occurring polypeptide herein comprises an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, SEQ ID NO: 19, and a homolog thereof (e.g., having at least 80%, at least 85%, at least 90%, at least 95%, or at least 98% sequence identity thereto). In more specific embodiments, a non-naturally occurring polypeptide herein consists of an amino acid sequence selected from the group consisting of: SEQ ID NO: 5, SEQ ID NO: 7, SEQ ID NO: 8, SEQ ID NO: 10, SEQ ID NO: 13, SEQ ID NO: 15, SEQ ID NO: 17, SEQ ID NO: 19, and a homolog thereof (e.g., having at least 80%, at least 85%, at least 90%, at least 95%, or at least 98% sequence identity thereto).

In another aspect, a non-naturally occurring polypeptide described herein further comprises one or more amino acid sequences selected from the group consisting of: a secretion tag, a histidine tag, a green fluorescent protein tag, and a protease cleavage site. In one aspect, the secretion tag is DsbA, PelB, OmpA, TolB, MalE, lpp, TorA, HylA, DegP, or a hybrid secretion tag that comprises a portion of one secretion tag fused to a portion of a second secretion tag. In a specific embodiment, the secretion tag is DsbA.

In certain embodiments, compositions are provided herein. In some embodiments, such a composition comprises any polypeptides (e.g., truncated and/or non-naturally occurring elastin) described herein. In one aspect, provided herein are compositions that comprise any suitable amount such as between 0.001% w/w and 30% w/w, of any polypeptide (e.g., truncated and/or non-naturally occurring elastin) provided herein. In some cases, the composition comprises between 0.001% w/w and 1% w/w, between 0.001% w/w and 0.05% w/w, between 0.001% w/w and 0.03% w/w, between 0.001% w/w and 0.02% w/w, between 0.001% w/w and 0.01% w/w, between 0.005% w/w and 0.1% w/w, between 0.005% w/w and 0.03% w/w, between 0.005% w/w and 0.02% w/w, or between 0.005% w/w and 0.01% w/w of any polypeptide (e.g., truncated and/or non-naturally occurring elastin) provided herein.

In certain embodiments, a composition provided herein is a topical composition, such as a composition that is formulated and/or suitable for topical administration or use. The topical compositions provided herein may include any polypeptide described herein (e.g., truncated and/or non-naturally occurring elastin, e.g., in any suitable amount) and at least one additional ingredient. In one aspect, provided herein is a method, such as of providing a benefit (e.g., as described herein) to the skin of a subject, the method comprising topically administering the topical composition to the skin of a subject. In specific embodiments, the topical compositions may be used in methods for decreasing skin damage, promoting the repair of damaged skin, stimulating production of collagen by skin cells, improving skin health and moisturization, improving the appearance of skin. In certain embodiments, the topical compositions may be used in methods for increasing, promoting, stimulating, or otherwise increasing elastin production in the skin. In certain embodiments, the topical compositions may be used in methods for stimulating the growth of fibroblast cells, and/or stimulating synthesis of tropoelastin, and/or decreasing the formation of thymine-thymine (TT) dimer formation in cells. The topical compositions can further comprise at least one additional ingredient comprising a topical carrier or a preservative.

In an embodiment, the topical compositions comprise one or more topical carriers selected from the group consisting of: water, oil glycereth-8 esters, glycerin, coconut alkanes, hydroxyethyl acrylate/sodium acryloyldimethyl taurate copolymer, pentylene glycol, disodium EDTA, caprylyl glycol, chlorphenesin, phenoxyethanol, liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, and cyclopentasiloxane.

In another embodiment, the topical compositions comprise one or more preservatives selected from the group consisting of: tocopherol, diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, methyl paraben, sorbic acid, GERMABEN® II, rosemary extract, and EDTA.

In some embodiments, methods for decreasing skin damage and/or promoting the repair of damaged skin are provided. The method may comprise applying a composition (e.g., a topical composition) comprising any non-naturally occurring polypeptide described herein (e.g., a truncated and/or non-naturally occurring human elastin) to the skin of a subject. In some cases, the method increases the viability of the fibroblast cells or keratinocytes of the skin of the subject. In some cases, the application of the composition (e.g., a topical composition) increases the synthesis of tropoelastin by the fibroblast cells of the subject's skin. In some cases, the topical application of the composition (e.g., a topical composition) protects skin or keratinocytes against UV damage. In some cases, application of a composition (e.g., a topical composition) to the skin of a subject decreases thymine-thymine (TT) dimer formation.

In another aspect, a non-naturally occurring polypeptide (e.g., a truncated human elastin) is a recombinant polypeptide (e.g., produced by a host cell, e.g., by recombinant expression). The recombinant polypeptide may be a recombinant human elastin (e.g., a non-naturally occurring and/or truncated human elastin). In an embodiment, the recombinant elastin is a full-length or truncated elastin. In one embodiment, the recombinant polypeptide (e.g., a truncated human elastin) is truncated at the C-terminal end relative to a natural and/or full-length elastin, the N-terminal end relative to a natural and/or full-length elastin, internally truncated relative to a natural and/or full-length elastin, or truncated at both the C-terminal end and the N-terminal end of a natural and/or full-length elastin.

In some aspects, a recombinant polypeptide (e.g., a non-naturally occurring and/or truncated human elastin) described herein may be between 10 and 700 amino acids in length, between 10 and 600 amino acids in length, between 10 and 500 amino acids in length, between 10 and 400 amino acids in length, between 10 and 300 amino acids in length, between 10 and 200 amino acids in length, between 10 and 100 amino acids in length, between 10 and 50 amino acids in length, between 50 and 800 amino acids in length, between 50 and 700 amino acids in length, between 50 and 600 amino acids in length, between 50 and 500 amino acids in length, between 50 and 400 amino acids in length, between 50 and 300 amino acids in length, between 50 and 200 amino acids in length, or between 50 and 100 amino acids in length.

In another embodiment, a recombinant polypeptide described herein (e.g., a non-naturally occurring and/or truncated human elastin) may have a molecular weight of between 1 kDa and 60 kDa, between 5 kDa and 55 kDa, between 5 kDa and 50 kDa, between 5 kDa and 45 kDa, between 5 kDa and 40 kDa, between 5 kDa and 35 kDa, between 5 kDa and 30 kDa, between 5 kDa and 25 kDa, between 5 kDa and 20 kDa, between 5 kDa and 15 kDa, between 5 kDa and 10 kDa, between 10 kDa and 40 kDa, between 10 kDa and 35 kDa, between 10 kDa and 30 kDa, between 10 kDa and 25 kDa, or between 10 kDa and 20 kDa.

In various aspects, a recombinant host cell may comprise at least one copy of a heterologous nucleic acid sequence encoding a recombinant polypeptide described herein (e.g., a non-naturally occurring and/or truncated elastin). In some cases, a nucleic acid sequence encoding a recombinant polypeptide (e.g., a non-naturally occurring and/or truncated human elastin) may comprise a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16, SEQ ID NO: 18, and a homolog thereof (e.g., having at least 80%, at least 85%, at least 90%, at least 95%, or at least 98% sequence identity thereto). In another embodiment, a nucleic acid sequence encoding a recombinant polypeptide (e.g., a non-naturally occurring and/or truncated human elastin) may consist of a nucleic acid sequence selected from the group consisting of: SEQ ID NO: 4, SEQ ID NO: 6, SEQ ID NO: 9, SEQ ID NO: 11, SEQ ID NO: 12, SEQ ID NO: 14, SEQ ID NO: 16, SEQ ID NO: 18, and a homolog thereof (e.g., having at least 80%, at least 85%, at least 90%, at least 95%, or at least 98% sequence identity thereto).

In another embodiment, a recombinant polypeptide described herein may include one or more of the group consisting of: a secretion tag, a histidine tag, a fluorescent protein tag, and a protease cleavage site. In some cases, the secretion tag is DsbA, PelB, OmpA, TolB, MalE, lpp, TorA, HylA, DegP, or a hybrid secretion tag that comprises a portion of one secretion tag fused to a portion of a second secretion tag. In a specific embodiment, the secretion tag is DsbA.

The polynucleotides encoding the polypeptides described herein (e.g., non-naturally occurring and/or truncated elastin), and vectors comprising the polynucleotides, can be used to transform host cells which may then express the recombinant polypeptides (e.g., non-naturally occurring and/or truncated human elastin).

In another embodiment, host cells that have been engineered (e.g., recombinant host cells) to express the disclosed recombinant polypeptides (e.g., non-naturally occurring and/or truncated elastin) are provided. Host cells can be any host cell including bacterial cells, yeast cells, fungal cells, insect cells, mammalian cells, plant cells, and any other cells used to express exogenous polynucleotides. In a specific embodiment, the host cell is *Escherichia coli*. In specific embodiments, the host cell is capable of secreting the recombinant polypeptide extracellularly (e.g., into a culture medium).

In another embodiment, a method of producing a polypeptide described herein is provided (e.g., a recombinant polypeptide such as, e.g., a non-naturally occurring elastin and/or a truncated elastin). The method comprises the steps of inoculating a culture medium with a recombinant host cell comprising at least one copy of a heterologous nucleic acid sequence encoding a polypeptide described herein (e.g., a non-naturally occurring and/or truncated elastin), cultivating the host cell (e.g., culturing the host cell in the culture medium) whereby the host cell secretes the recombinant polypeptide extracellularly (e.g., into the culture medium), and isolating the recombinant polypeptide (e.g., from the host cell and/or the culture medium).

In another aspect, provided herein are methods for decreasing the production of inflammatory cytokines in a skin cell. In one embodiment, the skin cell is a keratinocyte or a fibroblast. The method comprises applying a polypeptide described herein (e.g., a non-naturally occurring and/or truncated elastin, e.g., in a topical formulation) to a skin cell or to skin of a subject. In some instances, the production of inflammatory cytokines (e.g., TNFα, IL-1α, IL-1β, IL-3, IL-6, IL-7, IL-8, IL-10, IL-18, and IL-1RA) are decreased.

In another aspect, a method for decreasing skin damage or promoting the repair of damaged skin is provided. The method may comprise applying a composition (e.g., a composition formulated for topical application) comprising a non-naturally occurring polypeptide described herein (e.g., a truncated elastin) to the skin of a subject. In some cases, the method increases the viability of the fibroblast cells or keratinocytes of the skin of the subject. In some cases, the application of the composition increases the synthesis of tropoelastin by the fibroblast cells or keratinocytes of the subject's skin. In some cases, the topical application of the composition protects skin, fibroblasts, or keratinocytes against UV damage. In some cases, thymine-thymine (TT) dimer formation is decreased by topical application of the compositions provided herein.

In another aspect, provided herein are methods of protecting skin cells against the effect of exposure to urban dust. In some cases, the method comprises applying a non-naturally occurring polypeptide described herein (e.g., a truncated elastin) to a skin cell or to skin of a subject. In some cases, the exposure of the skin cell or the skin of the subject to the non-naturally occurring polypeptide increases the viability of the skin cell after exposure to urban dust. The skin cell may be a keratinocyte or a fibroblast.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 depicts untreated control fibroblasts (A), fibroblasts treated with a 0.1% w/w solution of an exemplary polypeptide provided herein (B), fibroblasts treated with a 0.05% w/w solution of an exemplary polypeptide provided herein (C), and fibroblasts treated with a 0.025% w/w solution of an exemplary polypeptide provided herein (D).

FIG. 4 depicts a 0.2% w/w solution of an exemplary polypeptide provided herein (A), a 0.1% w/w solution of an exemplary polypeptide provided herein (B), a 0.05% w/w solution of an exemplary polypeptide provided herein (C), a 0.025% w/w solution of an exemplary polypeptide provided herein (D), and a 0.0125% w/w solution of an exemplary polypeptide provided herein (E).

FIG. 5 depicts untreated keratinocytes (A), and keratinocytes treated with an exemplary polypeptide provided herein (B).

FIG. 6 depicts untreated keratinocytes (A), and keratinocytes treated with an exemplary polypeptide provided herein (B).

DESCRIPTION

Figure 1:
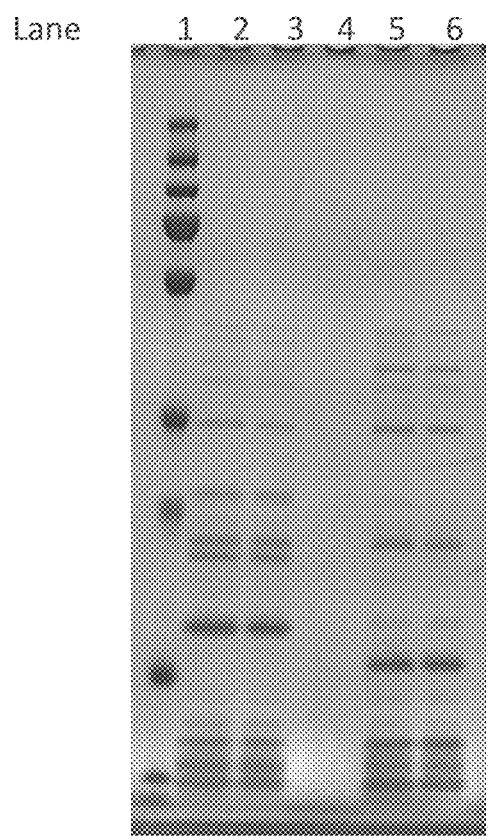
FIG. 1 shows a photograph of a protein gel. Lane 1 is the size marker. Lanes 2 and 3 show that the 23 kDa truncated human elastin of Example 10 runs on the gel at the expected molecular weight. Lane 4 is blank with no proteins loaded. Lanes 5 and 6 show that the 13 kDa truncated human elastin of Example 11 runs on the gel at the expected molecular weight.

In the following description, certain specific details are set forth in order to provide a thorough understanding of various embodiments of the disclosure. However, one skilled in the art will understand that the disclosure may be practiced without these details.

As used herein the term "about" generally refers to ±10%.

The term "consisting of" means "including and limited to". In general, a disclosure of "comprising" includes a disclosure of "consisting of".

The term "consisting essentially of" means that the composition, method or structure may include additional ingredients, steps and/or parts, but only if the additional ingredients, steps and/or parts do not materially alter the basic and novel characteristics of the claimed composition, method or structure. In general, a disclosure of "comprising" includes a disclosure of "consisting essentially of".

As used herein, the singular form "a", "an" and "the" include plural references unless the context clearly dictates otherwise. For example, the term "a compound" or "at least one compound" may include a plurality of compounds, including mixtures thereof.

Throughout this document, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals there between.

The term "elastin" or "elastin-like" as used herein refers, in some instances, to a (e.g., monomeric) polypeptide that can associate with one or more elastin or elastin-like polypeptides and/or can bind to another polypeptide, nucleic acids, polysaccharides, lipids or other molecules. Generally, the terms "elastin" or "elastin-like" refer to a polypeptide that has one or more functions associated with a naturally occurring elastin. The non-naturally occurring polypeptides provided herein (e.g., a truncated elastin) may be termed "elastin" or "elastin-like" when they have one or more functions associated with a naturally occurring elastin. The term "tropoelastin" as used herein generally refers to polypeptides that can be further processed (e.g., by cleavage, splicing, etc.) to produce an elastin polypeptide. A non-limiting example of an elastin is a naturally occurring human elastin having an amino acid sequence according to SEQ ID NO: 20.

The term "expression vector" or "vector" as used herein generally refers to a nucleic acid assembly which is capable of directing the expression of the exogenous gene. The expression vector may include a promoter which is operably linked to the exogenous gene, restriction endonuclease sites, nucleic acids that encode one or more selection markers, and other nucleic acids useful in the practice of recombinant technologies.

The term "extracellular matrix" as used herein generally refers to a network of extracellular macromolecules such as elastin, collagen, enzymes, and glycoproteins that provide the scaffolding for cells in multicellular organisms. The extracellular matrix may provide structural components that mediate cell adhesion, cell to cell communication, and other functions.

The term "fibroblast" as used herein generally refers to a cell that synthesizes tropoelastin, procollagen and other structural proteins. Fibroblasts may be widely distributed in the body and may be found in skin, connective tissue, and other tissues.

The term "fluorescent protein" generally refers to a protein that may be used in genetic engineering technologies as a reporter of expression of an exogenous polynucleotide. The protein when exposed to ultraviolet or blue light fluoresces and emits a bright visible light. Proteins that emit green light include green fluorescent protein (GFP) and proteins that emit red light include red fluorescent protein (RFP).

The term "gene" as used herein generally refers to a polynucleotide that encodes a specific protein, and which may refer to the coding region alone or may include regulatory sequences preceding (5' non-coding sequences) and following (3' non-coding sequences) the coding sequence.

The term "histidine tag" generally refers to a 2-30 contiguous series of histidine residues (SEQ ID NO: 21) on a recombinant polypeptide.

The term "host cell" generally refers to a cell that is engineered to express an introduced exogenous polynucleotide.

The term "keratinocyte" generally refers to a cell that produces keratins, tropoelastin, and other cellular components found in the epidermal layer of the skin.

The term "non-naturally occurring" as used herein generally refers to a gene, a polypeptide, or a protein, for example, an elastin, that is not normally found in nature. The non-naturally occurring elastin may be recombinantly produced (e.g., by expression by a recombinant host cell). The non-naturally occurring elastin may be a recombinant elastin (e.g., produced by a recombinant host cell). The non-naturally occurring elastin may be a truncated elastin. Other non-naturally occurring elastin polypeptides include chimeric elastins. A chimeric elastin may be a polypeptide wherein one portion of an elastin polypeptide is contiguous with a portion of a second elastin polypeptide. For example, a molecule comprising a portion of a human elastin contiguous with a portion of another human polypeptide may be a chimeric elastin. In another embodiment, the non-naturally occurring elastin comprises a fusion polypeptide that includes additional amino acids such as a secretion tag, histidine tag, green fluorescent protein, and/or protease cleavage site.

In general, disclosure of an elastin or a truncated elastin provided herein, such as having a specific amino acid sequence, includes polypeptides having or comprising that precise amino acid sequence and homologs thereof. In some instances, homologs of an amino acid sequence provided herein may have a longer or shorter sequence and may have a substitution of one or more amino acid residue of such amino acid sequence. Such homologs have a specific sequence identity to the recited sequence, such as in an amount provided herein. Sequence identity, such as for the purpose of assessing percent identity, may be measured by any suitable alignment algorithm, including but not limited to the Needleman-Wunsch algorithm (see e.g. the EMBOSS Needle aligner available at ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at ebi.ac.uk/Tools/psa/emboss_water/nucleotide.html, optionally with default settings). Optimal alignment may be assessed using any suitable parameters of a chosen algorithm, including default parameters. In some cases, a non-naturally occurring elastin may have at least 60%, 65%, 70%, 75%, 80%, 85%, 90%, 95%, 97%, 98%, 99%, or 100% sequence identity to a sequence disclosed herein.

The term "protease cleavage site" generally refers to an amino acid sequence that is cleaved by a specific protease.

The term "secretion tag" or "signal peptide" generally refers to an amino acid sequence that recruits the host cell's cellular machinery to transport an expressed protein to a particular location or cellular organelle of the host cell.

The term "truncated elastin" generally refers to a monomeric polypeptide that is smaller than a full-length elastin wherein one or more portions of the full-length elastin is not present. Elastin polypeptides may be truncated at the C-terminal end relative to a full-length elastin, the N-terminal end relative to a full-length elastin, truncated by removal of internal portion(s) of the full-length elastin polypeptide (e.g., an internal truncation), or truncated at both the C-terminal end and the N-terminal end relative to a full-length elastin. In a non-limiting embodiment, a truncated human elastin may comprise an amino acid sequence according to SEQ ID NO. 19, or a homolog thereof. Generally, a truncated elastin provided herein may have a function and/or provide a benefit (e.g., as provided herein) similar or substantially similar to that of a natural or a full-length elastin. In some cases, a truncated elastin provided herein may have improved or increased function and/or benefit (e.g., as provided herein) as compared to a natural or a full-length elastin.

When used in reference to an amino acid position, a "truncation" is inclusive of said amino acid position. For example, an N-terminal truncation at amino acid position 100 of a full-length protein means a truncation of 100 amino acids from the N-terminus of the full-length protein (i.e., the truncated protein is missing amino acid positions 1 through 100 of the full-length protein). Similarly, a C-terminal truncation at amino acid position 901 of a full-length protein (assuming a 1000 amino acid full-length protein) means a truncation of 100 amino acids from the C-terminus (i.e., the truncated protein is missing amino acid positions 901 through 1000 of the full-length protein). Similarly, an internal truncation at amino acid positions 101 and 200 means an internal truncation of 100 amino acids of the full-length protein (i.e., the truncated protein is missing amino acid positions 101 to 200 of the full-length protein).

In some embodiments, the cell culture may comprise one or more of ammonium chloride, ammonium sulfate, calcium chloride, amino acids, iron(II) sulfate, magnesium sulfate, peptone, potassium phosphate, sodium chloride, sodium phosphate, and yeast extract.

The host bacterial cell may be cultured continuously or discontinuously; in a batch process, a fed-batch process or a repeated fed-batch process.

In one aspect, a non-naturally occurring elastin is provided. In some cases, the non-naturally occurring elastin is a recombinant polypeptide that is produced by a host cell (e.g., a recombinant cell). In some cases, the non-naturally occurring elastin may be a human elastin. In some cases, the non-naturally occurring elastin may be a truncated elastin. The truncated elastin may be truncated relative to a full-length elastin (e.g., having an amino acid sequence according to SEQ ID NO: 20). The truncation may be an internal truncation relative to a full-length elastin, a truncation at the N-terminal portion relative to a full-length elastin, a truncation at the C-terminal portion relative to a full-length elastin, or a truncation at both the C-terminal end and the N-terminal end relative to a full-length elastin.

The truncated elastin may have a truncation of between 10 and 700 amino acids in length, between 10 and 600 amino acids in length, between 10 and 500 amino acids in length, between 10 and 400 amino acids in length, between 10 and 300 amino acids in length, between 10 and 200 amino acids in length, between 10 and 100 amino acids in length, between 10 and 50 amino acids in length, between 50 and 800 amino acids in length, between 50 and 700 amino acids in length, between 50 and 600 amino acids in length, between 50 and 500 amino acids in length, between 50 and 400 amino acids in length, between 50 and 300 amino acids in length, between 50 and 200 amino acids in length, or between 50 and 100 amino acids in length, relative to a full-length elastin. In another embodiment, a truncated elastin may be truncated by 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, or 750 amino acids relative to a full-length elastin. The truncated elastin may be encoded by a portion of a polynucleotide sequence or the entire polynucleotide sequence disclosed herein.

In some embodiments, a truncated elastin (e.g., amino acid sequence thereof) (e.g., of a polypeptide provided herein) may be truncated at the C-terminal end (relative to a full-length elastin) by any suitable number of amino acid residues, such as up to 10, 10 to 800, 10 to 700, 10 to 500, 10 to 400, 10 to 300, 10 to 200, 10 to 100, 50 to 800, 50 to 700, 50 to 600, 50 to 500, 50 to 400, 50 to 300, 50 to 200, 50 to 100, or the like. In some cases, a truncated elastin may be truncated at the C-terminal end (relative to a full-length elastin) by 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more amino acids.

In some embodiments, a truncated elastin (e.g., amino acid sequence thereof) (e.g., of a polypeptide provided herein) may be truncated at the N-terminal end (relative to a full-length elastin) by any suitable number of amino acid residues, such as up to 10, 10 to 800, 10 to 700, 10 to 500, 10 to 400, 10 to 300, 10 to 200, 10 to 100, 50 to 800, 50 to 700, 50 to 600, 50 to 500, 50 to 400, 50 to 300, 50 to 200, 50 to 100, or the like. In some cases, a truncated elastin may be truncated at the N-terminal end (relative to a full-length elastin) by 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more amino acids.

In some embodiments, a truncated elastin (e.g., amino acid sequence thereof) (e.g., of a polypeptide provided herein) may be truncated at both the N-terminal end and the C-terminal end relative to a full-length elastin. In some instances, a truncated elastin may be truncated at the N-terminal end (relative to a full-length elastin) by any suitable number of amino acid residues, such as up to 10, 10 to 800, 10 to 700, 10 to 500, 10 to 400, 10 to 300, 10 to 200, 10 to 100, 50 to 800, 50 to 700, 50 to 600, 50 to 500, 50 to 400, 50 to 300, 50 to 200, 50 to 100, or the like; and may be truncated at the C-terminal end (relative to a full-length elastin) by any suitable number of amino acid residues, such as up to 10, 10 to 800, 10 to 700, 10 to 500, 10 to 400, 10 to 300, 10 to 200, 10 to 100, 50 to 800, 50 to 700, 50 to 600, 50 to 500, 50 to 400, 50 to 300, 50 to 200, 50 to 100, or the like. In some cases, a truncated elastin may be truncated at the N-terminal end (relative to a full-length elastin) by 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more amino acids; and may be truncated at the C-terminal end (relative to a full-length elastin) by 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more amino acids.

In some embodiments, a truncated elastin (e.g., amino acid sequence thereof) (e.g., of a polypeptide provided herein) may be internally truncated (relative to a full-length elastin) by any suitable number of amino acid residues, such as up to 10, 10 to 800, 10 to 700, 10 to 500, 10 to 400, 10 to 300, 10 to 200, 10 to 100, 50 to 800, 50 to 700, 50 to 600, 50 to 500, 50 to 400, 50 to 300, 50 to 200, 50 to 100, or the like. In some cases, a truncated elastin may be internally truncated (relative to a full-length elastin) by 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more amino acids.

A truncated elastin disclosed herein may comprise a truncation relative to a full-length elastin. In some embodiments, a truncated elastin disclosed herein may comprise a truncation relative to a full-length human elastin. In some cases, a full-length human elastin has an amino acid sequence according to SEQ ID NO: 20 provided in Table 1 below.

TABLE 1

Full-length elastin amino acid sequences

| Elastin | Amino Acid Sequence |
|---|---|
| Human elastin (without the native secretion tag) | GGVPGAIPGGVPGGVFYPGAGLGALGGGALGPGGKP LKPVPGGLAGAGLGAGLGAFPAVTFPGALVPGGVAD AAAAYKAAKAGAGLGGVPGVGGLGVSAGAVVPQPGA GVKPGKVPGVGLPGVYPGGVLPGARFPGVGVLPGVP TGAGVKPKAPGVGGAFAGIPGVGPFGGPQPGVPLGY PIKAPKLPGGYGLPYTTGKLPYGYGPGGVAGAAGKA GYPTGTGVGPQAAAAAAAKAAAKFGAGAAGVLPGVG GAGVPGVGPGAIPGIGGIAGVGTPAAAAAAAAAKAA KYGAAAGLVPGGPGFGPGVVGVPGAGVPGVGVPGAG IPVVPGAGIPGAAVPGVVSPEAAAKAAAKAAKYGAR PGVGVGGIPTYGVGAGGFPGFGVGVGGIPGVAGVPG VGGVPGVGGVPGVGISPEAQAAAAAKAAKYGAAGAG VLGGLVPGPQAAVPGVPGTGGVPGVGTPAAAAAKAA AKAAQFGLVPGVGVAPGVGVAPGVGVAPGVGLAPGV GVAPGVGVAPGVGVAPGIGPGGVAAAAKSAAKVAAK AQLRAAAGLGAGIPGLGVGVGVPGLGVGAGVPGLGV GAGVPGFGAGADEGVRRSLSPELREGDPSSSQHLPS TPSSPRVPGALAAAKAAKYGAAVPGVLGGLGALGGV GIPGGVVGAGPAAAAAAAKAAAKAAQFGLVGAAGLG GLGVGGLGVPGVGGLGGIPPAAAAKAAKYGAAGLGG VLGGAGQFPLGGVAARPGFGLSPIFPGGACLGKACG RKRK (SEQ ID NO: 20) |

In some cases, a truncated elastin as described herein may comprise an N-terminal truncation at any amino acid position between amino acid positions 1 and 68; between amino acid positions 1 and 73; between amino acid positions 1 and 78; between amino acid positions 1 and 83; between amino acid positions 1 and 88; between amino acid positions 1 and 93; or between amino acid positions 1 and 98 of SEQ ID NO: 20. In some cases, a truncated elastin as described herein may comprise a C-terminal truncation at any amino acid position between amino acid positions 213 and 760; between amino acid positions 218 and 760; between amino acid positions 223 and 760; between amino acid positions 228 and 760; between amino acid positions 233 and 760; between amino acid positions 238 and 760; or between 243 and 760 of SEQ ID NO: 20. In some cases, a truncated elastin as described herein may comprise both an N-terminal truncation and a C-terminal truncation. For example, a truncated elastin as described herein may comprise an N-terminal truncation at any amino acid position between amino acid positions 1 and 68; between amino acid positions 1 and 73; between amino acid positions 1 and 78; between amino acid positions 1 and 83; between amino acid positions 1 and 88; between amino acid positions 1 and 93; or between amino acid positions 1 and 98 of SEQ ID NO: 20; and a C-terminal truncation at any amino acid position between amino acid positions 213 and 760; between amino acid positions 218 and 760; between amino acid positions 223 and 760; between amino acid positions 228 and 760; between amino acid positions 233 and 760; between amino acid positions 238 and 760; or between 243 and 760 of SEQ ID NO: 20. In a specific embodiment, a truncated elastin disclosed herein may comprise an N-terminal truncation at amino acid position 83 of SEQ ID NO: 20; and a C-terminal truncation at amino acid position 228 of SEQ ID NO: 20.

In some cases, a truncated elastin as described herein may comprise an N-terminal truncation at any amino acid position between amino acid positions 1 and 68; between amino acid positions 1 and 73; between amino acid positions 1 and 78; between amino acid positions 1 and 83; between amino acid positions 1 and 88; between amino acid positions 1 and 93; or between amino acid positions 1 and 98 of SEQ ID NO: 20. In some cases, a truncated elastin as described herein may comprise a C-terminal truncation at any amino acid position between amino acid positions 331 and 760; between amino acid positions 336 and 760; between amino acid positions 341 and 760; between amino acid positions 346 and 760; between amino acid positions 351 and 760; between amino acid positions 356 and 760; or between amino acid positions 361 and 760 of SEQ ID NO: 20. In some cases, a truncated elastin as described herein may comprise both an N-terminal truncation and a C-terminal truncation. For example, a truncated elastin as described herein may comprise an N-terminal truncation at any amino acid position between amino acid positions 1 and 68; between amino acid positions 1 and 73; between amino acid positions 1 and 78; between amino acid positions 1 and 83; between amino acid positions 1 and 88; between amino acid positions 1 and 93; or between amino acid positions 1 and 98 of SEQ ID NO: 20; and a C-terminal truncation at any amino acid position between amino acid positions 331 and 760; between amino acid positions 336 and 760; between amino acid positions 341 and 760; between amino acid positions 346 and 760; between amino acid positions 351 and 760; between amino acid positions 356 and 760; or between amino acid positions 361 and 760 of SEQ ID NO: 20. In a specific embodiment, a truncated elastin disclosed herein may comprise an N-terminal truncation at amino acid position 83 of SEQ ID NO: 20; and a C-terminal truncation at amino acid position 346 of SEQ ID NO: 20.

In some cases, a truncated elastin may comprise any amino acid sequence provided in Table 2 below. In some cases, a truncated elastin may consist of any amino acid sequence provided in Table 2 below. In some cases, a truncated elastin may consist essentially of any amino acid sequence provided in Table 2 below. In specific embodiments, the non-naturally occurring elastin is or comprises an amino acid sequence of any one of SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19. In some embodiments, the truncated elastin comprises an amino acid sequence having at least 80%, at least 85%, at least 90%, at least 95%, or at least 98% sequence identity to any one of SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19.

In some embodiments, the truncated elastin may be a truncate (e.g., a polypeptide having at least 50, at least 60, at least 70, at least 80, at least 90, at least 100, at least 110, at least 120, at least 130, at least 140, or at least 150 amino acids) of any one of SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19; or may be a truncate (e.g., a polypeptide having at least 50, at least 60, at least 70, at least 80, at least 90, at least 100, at least 110, at least 120, at least 130, at least 140, or at least 150 amino acids) of an amino acid sequence having at least 80%, at least 85%, at least 90%, at least 95%, or at least 98% sequence identity to any one of SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19. For example, the truncated elastin may have an N-terminal truncation, a C-terminal truncation, and/or an internal truncation relative to any one of SEQ ID NO: 5, SEQ ID NO: 7, SEQ ID NO: 8, SEQ ID NO: 10, SEQ ID NO: 13, SEQ ID NO: 15, SEQ ID NO: 17, and SEQ ID NO: 19; or an N-terminal truncation, a C-terminal truncation, and/or an internal truncation relative to an amino acid sequence having at least 80%, at least 85%, at least 90%, at least 95%, or at least 98% sequence identity to any one of SEQ ID NO: 5, SEQ ID NO: 7, SEQ ID NO: 8, SE ID NO: 10, SE ID NO: 13, SE ID NO: 15, SE ID NO: 17, and SE ID NO: 19.

TABLE 2

Non-limiting examples of truncated elastins

| SEQ ID NO: | Amino acid sequence |
|---|---|
| SEQ ID NO: 5 | MKKIWLALAGLVLAFSASAGPQPGVPLGYPIKAPKLPGGYGLPY TTGKLPYGYGPGGVAGAAGKAGYPTGTGVGPQAAAAAAAKAAAK FGAGAAGVLPGVGGAGVPGVGPGAIPGIGGIAGVGTPAAAAAAAA AAKAAKYGAAAGLVPGGPGFGPGVVGVPGAGVPGVGVPGAGIPV VPGAGIPGAAVPGVVSPEAAAKAAAKAAKYGARPGVGVGGIPTY GVGAGGFPGFGVGVGGIPGVAGVPGVGGVPGVGGVPGVGISPEA QAAAAAKAAKYGAAGAGVLGGLVPGPQAAVPGVPGTGGVPGVGT P |
| SEQ ID NO: 7 | GPQPGVPLGYPIKAPKLPGGYGLPYTTGKLPYGYGPGGVAGAAG KAGYPTGTGVGPQAAAAAAAKAAAKFGAGAAGVLPGVGGAGVPG VPGAIPGIGGIAGVGTPAAAAAAAAAAKAAKYGAAAGLVPGGPG FGPGVVGVPGAGVPGVGVPGAGIPVVPGAGIPGAAVPGVVSPEA AAKAAAKAAKYGARPGVGVGGIPTYGVGAGGFPGFGVGVGGIPG VAGVPGVGGVPGVGGVPGVGISPEAQAAAAAKAAKYGAAGAGVL GGLVPGPQAAVPGVPGTGGVPGVGTP |
| SEQ ID NO: 8 | GPGGVAAAAKSAAKVAAKAQLRAAAGLGAGIPGLGVGVGVPGLG VGAGVPGLGVGAGVPGFGAGADEGVRRSLSPELREGDPSSSQHL PSTPSSPRVPGALAAAKAAKYGAAVPGVLGGLGALGGVGIPGGV VGAGPAAAAAAAKAAAKAAQFGLVGAAGLGGLGVGGLGVPGVGG LGGIPPAAAAKAAKYGAAGLGGVLGGAGQFPLGGVAARPGFGLS PIFPGGACLGKACGRKRK |
| SEQ ID NO: 10 | GGVPGAIPGGVPGGVFYPGAGLGALGGGALGPGGKPLKPVPGGL AGAGLGAGLGAFPAVTFPGALVPGGVADAAAAYKAAKAGAGLGG VPGVGGLGVSAGAVVPQPGAGVKPGKVPGVGLPGVYPGGVLPGA RFPGVGVLPGVPTGAGVKPKAPGVGGAFAGIPGVGPFGGPQPGV PLGYPIKAPKLPGGYGLPYTTGKLPYGYGPGGVAGAAGKAGYPT GTGVGPQAAAAAAAKAAAKFGAGAAGVLPGVGGAGVPGVPGAIP GIGGIAGVGTPAAAAAAAAAAKAAKYGAAAGLVPGGPGFGPGVV GVPGAGVPGVGVPGAGIPVVPGAGIPGAAVPGVVSPEAAAKAAA KAAKYGARPGVGVGGIPTYGVGAGGFPGFGVGVGGIPGVAGVPG VGGVPGVGGVPGVGISPEAQAAAAAKAAKYGAAGAGVLGGLVPG |

TABLE 2-continued

Non-limiting examples of truncated elastins

| SEQ ID NO: | Amino acid sequence |
|---|---|
| | PQAAVPGVPGTGGVPGVGTPAAAAKSAAKVAAKAQLRAAAGLGA GIPGLGVGVGVPGLGVGAGVPGLGVGAGVPGFGAGADEGVRRSL SPELREGDPSSSQHLPSTPSSPRVPGALAAAKAAKYGAAVPGVL GGLGALGGVGIPGGVVGAGPAAAAAAAKAAAKAAQFGLVGAAGL GGLGVGGLGVPGVGGLGGIPPAAAAKAAKYGAAGLGGVLGGAGQ FPLGGVAARPGFGLSPIFPGGACLGKACGRKRK |
| SEQ ID NO: 13 | MKKIWLALAGLVLAFSASAAGLGGVPGVGGLGVSAGAVVPQPGA GVKPGKVPGVGLPGVYPGGVLPGARFPGVGVLPGVPTGAGVKPK APGVGGAFAGIPGVGPFGGPQPGVPLGYPIKAPKLPGGYGLPYT TGKLPYGYGPGGVAGAAGKAGYPTGTGVGPQAAAAAAAKAAAKF GAGAAGVLPGVGGAGVPGVPGAIPGIGGIAGVGTPAAAAAAAAA AKAAKYGAAAGLVPGGPGFGPGVVGVPGAGVPGVGVPGAGIPVV PGAGIPGAAVPGVVSPE |
| SEQ ID NO: 15 | AGLGGVPGVGGLGVSAGAVVPQPGAGVKPGKVPGVGLPGVYPGG VLPGARFPGVGVLPGVPTGAGVKPKAPGVGGAFAGIPGVGPFGG PQPGVPLGYPIKAPKLPGGYGLPYTTGKLPYGYGPGGVAGAAGK AGYPTGTGVGPQAAAAAAAKAAAKFGAGAAGVLPGVGGAGVPGV PGAIPGIGGIAGVGTPAAAAAAAAAAKAAKYGAAAGLVPGGPGF GPGVVGVPGAGVPGVGVPGAGIPVVPGAGIPGAAVPGVVSPE |
| SEQ ID NO: 17 | MKKIWLALAGLVLAFSASAAGLGGVPGVGGLGVSAGAVVPQPGA GVKPGKVPGVGLPGVYPGGVLPGARFPGVGVLPGVPTGAGVKPK APGVGGAFAGIPGVGPFGGPQPGVPLGYPIKAPKLPGGYGLPYT TGKLPYGYGPGGVAGAAGKAGYPTGTGVGPQ |
| SEQ ID NO: 19 | AGLGGVPGVGGLGVSAGAVVPQPGAGVKPGKVPGVGLPGVYPGG VLPGARFPGVGVLPGVPTGAGVKPKAPGVGGAFAGIPGVGPFGG PQPGVPLGYPIKAPKLPGGYGLPYTTGKLPYGYGPGGVAGAAGK AGYPTGTGVGPQ |

In various aspects, the truncated human elastin does not comprise two or more contiguous amino acid sequences of VGVAPG (SEQ ID NO: 1). In some cases, the truncated human elastin does not comprise VGVAPGVGVAPG (SEQ ID NO: 2). In some cases, the truncated human elastin does not comprise VGVAPGVGVAPGVGVAPG (SEQ ID NO: 3). In some cases, the non-naturally occurring truncated human elastin reduces extracellular matrix degradation or does not cause extracellular matrix degradation.

In some cases, a truncated elastin may be between 100 and 150 amino acids, between 100 and 200 amino acids, between 100 and 300 amino acids, between 140 and 250 amino acids, between 140 and 200 amino acids, between 150 and 250 amino acids, between 160 and 250 amino acids, between 160 and 220 amino acids, between 170 and 200 amino acids, between 180 and 190 amino acids, or between 185 and 190 amino acids in length.

In some aspects, the truncated human elastin may have a molecular weight of at least about 5, 10, 15, 20, 25, 30, 35, 40, 45, 50 or more than 50 kDa. In some embodiments, the molecular weight is less than about 10, 15, 20, 25, 30, 35, 40, 45, or 50 kDa. In some embodiments, the molecular weight is between 1 kDa and 60 kDa, between 5 kDa and 55 kDa, between 5 kDa and 50 kDa, between 5 kDa and 45 kDa, between 5 kDa and 40 kDa, between 5 kDa and 35 kDa, between 5 kDa and 30 kDa, between 5 kDa and 25 kDa, between 5 kDa and 20 kDa, between 5 kDa and 15 kDa, between 5 kDa and 10 kDa, between 10 kDa and 40 kDa, between 10 kDa and 35 kDa, between 10 kDa and 30 kDa, between 10 kDa and 25 kDa, or between 10 kDa and 20 kDa.

The non-naturally occurring elastin may, in some embodiments, comprise a signal sequence. In general, the signal sequence may be a component of the expression vector, or it may be a part of the exogenous gene that is inserted into the vector. The signal sequence selected should be one that is recognized and processed (e.g., cleaved by a signal peptidase) by the host cell. For bacterial host cells that do not recognize and process the native signal sequence of the exogenous gene, the signal sequence may be substituted by any commonly known bacterial signal sequence. In some embodiments, recombinantly produced polypeptides can be targeted to the periplasmic space using the DsbA signal sequence. Dinh and Bernhardt, J Bacteriol, September 2011, 4984-4987.

The non-naturally occurring elastin may, in some embodiments, further comprise amino acid sequences including a secretion tag. The secretion tag may direct the elastin to the periplasmic space of the host cell. In particular embodiments, the signal peptide is derived from DsbA, PelB, OmpA, TolB, MalE, lpp, TorA, DegP, or HylA, or a hybrid secretion tag that comprises a portion of one secretion tag fused to a portion of a second secretion tag. In one aspect, the secretion tag is attached to the non-naturally occurring elastin. In another aspect, the secretion tag is cleaved from the non-naturally occurring elastin.

In some embodiments, the non-naturally occurring elastin further comprises a histidine tag. The histidine tag or polyhistidine tag may be a sequence of 2 to 20 histidine residues (SEQ ID NO: 22) that are attached to the elastin. The histidine tag may comprise 2 to 20 histidine residues (SEQ ID NO: 22), 5 to 15 histidine residues (SEQ ID NO: 23), 5 to 18 histidine residues (SEQ ID NO: 24), 5 to 16 histidine residues (SEQ ID NO: 25), 5 to 15 histidine residues (SEQ ID NO: 26), 5 to 14 histidine residues (SEQ ID NO: 27), 5 to 13 histidine residues (SEQ ID NO: 28), 5 to 12 histidine residues (SEQ ID NO: 29), 5 to 11 (SEQ ID NO: 30), 5 to 10 histidine residues (SEQ ID NO: 31), 6 to 12 histidine residues (SEQ ID NO: 32), 6 to 11 histidine residues (SEQ ID NO: 33), or 7 to 10 histidine residues (SEQ ID NO: 34). The histidine tags may be useful in purification of proteins by chromatographic methods utilizing nickel based chromatographic media. In one aspect, the histidine tag may be attached to the non-naturally occurring elastin. In another aspect, the histidine tag may be cleaved from the non-naturally occurring elastin.

In some embodiments, the non-naturally occurring elastin further comprises a fluorescent protein. Exemplary fluorescent proteins include green fluorescent protein (GFP) or red fluorescent protein (RFP). Fluorescent proteins are well known in the art. In one embodiment, the non-naturally occurring elastin comprises a GFP and/or RFP. In one embodiment, a superfolder GFP may be fused to the non-naturally occurring elastin. The superfolder GFP may be a GFP that folds properly even when fused to a poorly folded polypeptide.

In some embodiments, the non-naturally occurring elastin further comprises a protease cleavage site. The protease cleavage site may be useful to cleave the recombinantly produced elastin to remove one or more portions of the polypeptide. The portions of the polypeptide that may be removed include the secretion tag, the histidine tag, the fluorescent protein tag and/or a protease cleavage site. The proteases comprise endoproteases, exoproteases, serine proteases, cysteine proteases, threonine proteases, aspartic proteases, glutamic proteases, and metalloproteases. Exemplary protease cleavage sites include amino acids that are cleaved by Thrombin, TEV protease, Factor Xa, Enteropeptidase, and Rhinovirus 3C Protease. In one aspect, the cleavage tag maybe attached to the non-naturally occurring elastin. In another aspect, the cleavage tag may be removed by an appropriate protease from the non-naturally occurring elastin.

Provided in certain embodiments herein are (e.g., topical) compositions or formulations comprising one or more polypeptide provided herein. In some embodiments, the composition provides any suitable amount of polypeptide provided herein, such as in any suitable amount (e.g., an amount suitable to provide a benefit when given or administered to an individual or cell). In some specific embodiments, the composition comprises an amount suitable to provide a beneficial effect to the skin of a subject when (e.g., topically) administered to the skin of the subject. In specific embodiments, the composition comprises between 0.001% and 30% w/w of a polypeptide (e.g., a non-naturally occurring elastin) such as provided herein. In more specific embodiments, the composition comprises between 0.001% and 20% w/w of a polypeptide (e.g., a non-naturally occurring elastin) such as provided herein, between 0.001% and 10% w/w of a polypeptide (e.g., a non-naturally occurring elastin) such as provided herein, between 0.001% and 5% w/w of a polypeptide (e.g., a non-naturally occurring elastin) such as provided herein, between 0.001% and 2% w/w of a polypeptide (e.g., a non-naturally occurring elastin) such as provided herein, between 0.001% and 1% w/w of a polypeptide (e.g., a non-naturally occurring elastin) such as provided herein, between 0.001% and 0.5% w/w of a polypeptide (e.g., a non-naturally occurring elastin) such as provided herein, and between 0.001% and 0.2% w/w of a polypeptide (e.g., a non-naturally occurring elastin) such as provided herein.

In one aspect, the compositions that comprise non-naturally occurring human elastin are personal care products (e.g., cosmetics). In some embodiments, the compositions are formulated for topical administration. The compositions may contain other cosmetic ingredients suitable for human use. The personal care products may be useful for preventing or treating ultraviolet radiation damage to human skin or hair. The personal care products may be useful for increasing the firmness, elasticity, brightness, hydration, tactile texture, or visual texture of skin and/or stimulate collagen production. The personal care products may be applied to skin or hair. The compositions include, for example, masks, skin cleaners such as soap, cleansing creams, cleansing lotions, facial cleansers, cleansing milks, cleansing pads, facial washes, facial and body creams and moisturizers, facial serums, facial and body masks, facial Toners and mists, eye creams and eye treatments, exfoliator formulas, lip balms and lipsticks, hair shampoo, hair conditioner and body shampoos, hair and scalp serums, hair mists and sprays, eye shadow, concealer, mascara and other color cosmetics.

The compositions that comprise the non-naturally occurring elastin can further comprise at least one additional ingredient comprising a topical carrier or a preservative. The topical carrier comprises a topical carrier selected from the group consisting of liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, cyclopentasiloxane, and water. The preservative comprises a preservative selected from the group consisting of tocopherol, diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, phenoxyethanol, butylene glycol, 1,2 Hexanediol, methyl paraben, sorbic acid, GERMABEN® II, rosemary extract, and EDTA.

Also provided herein are methods of decreasing skin damage, promoting the repair of damaged skin, protecting skin against UV damage, and/or protecting skin cells against the effects of exposure to urban dust. In another embodiment, methods of increasing the firmness, elasticity, brightness, hydration, tactile texture, or visual texture of skin and/or stimulating elastin or collagen production is provided. The method comprises applying the composition comprising the non-naturally occurring elastin to the skin of a subject. Without being bound to a particular theory or mechanism, the non-naturally occurring elastin in the composition decreases skin damage by protecting against UV damage, and/or promotes the repair of damaged skin by increasing the viability of cells and/or increasing tropoelastin or procollagen synthesis when applied to skin, and/or promotes the viability of skin cells. The non-naturally occurring truncated human elastin, in one aspect, decreases the formation of thymine-thymine (TT) dimer formation.

The methods provided herein encompass the use of a composition for treatment indicated in the method, such as by the steps provided herein. In embodiments, the disclosure provides the use of a composition provided herein (e.g., a truncated elastin or a formulation comprising a truncated elastin) in a method provided herein.

In some embodiments, application of the composition stimulates the growth of fibroblast cells, and/or stimulates synthesis of tropoelastin, and/or decreases the formation of thymine-thymine (TT) dimer formation. In some embodiments, application of the composition stimulates the growth of fibroblast cells by at least about 10%, 20%, 30%, 40%, 50%, 60%, 70%, 80%, 90%, 100%, or more than 100%% compared to the skin or skin cell where the composition is not applied. In some embodiments, application of the composition stimulates the synthesis of tropoelastin by at least about 10%, 20%, 30%, 40%, 50%, 60%, 70%, 80%, 90%, 100%, or more than 100%% compared to the skin or skin cell where the composition is not applied. In some embodiments, application of the composition decreases the formation of TT dimer formation by at least about 10%, 20%, 30%, 40%, 50%, 60%, 70%, 80%, 90%, 100%, or more than 100%% compared to the skin or skin cell where the composition is not applied. In some embodiments, the formation of TT dimer formation is measured using an ELISA-based assay.

In some embodiments, disclosed herein is a method of promoting the repair of damaged skin, protecting the skin against UV damage, or increasing viability of skin cells, the method comprising the step of applying the composition to the skin or skin cell of a subject. In some embodiments, the damaged skin may be repaired by at least about 10%, 20%, 30%, 40%, 50%, 60%, 70%, 80%, 90%, 100%, or more than 100% when the composition is applied compared to the skin or skin cell where the composition is not applied. In some embodiments, the skin may be protected against UV damage by at least about 10%, 20%, 30%, 40%, 50%, 60%, 70%, 80%, 90%, 100%, or more than 100% when the composition is applied compared to the skin or skin cell where the composition is not applied. In some embodiments, viability of skin cells is increased by at least about 10%, 20%, 30%, 40%, 50%, 60%, 70%, 80%, 90%, 100%, or more than 100% compared to the skin or skin cell where the composition is not applied. In some embodiments, the skin cell may be a keratinocyte. In some embodiments, the skin cell may be a fibroblast. In some embodiments, the viability of fibroblasts may be measured using an MTT assay.

In some embodiments, disclosed herein is a method of increasing the synthesis of procollagen by fibroblast cells by applying the composition to the skin or skin cell of a subject. In some embodiments, the synthesis of procollagen by fibroblast cells present in the subject's skin may be increased by at least about 10%, 20%, 30%, 40%, 50%, 60%, 70%, 80%, 90%, 100%, or more than 100% when the composition is applied compared to the skin or skin cell where the composition is not applied. In some embodiments, the synthesis of procollagen by fibroblast cells present in the subject's skin may be increased by at least about 10%, 20%, 30%, 40%, 50%, 60%, 70%, 80%, 90%, 100%, or more than 100% as measured by an ELISA-based assay. In some embodiments, the ELISA-based assay measures levels of pro-collagen type I-C peptide.

In some embodiments, disclosed herein is a method of decreasing the production of inflammatory cytokines by a skin cell, the method comprising the step of applying a non-naturally occurring elastin or composition comprising non-naturally occurring elastin to the skin or skin cell of a subject. In some embodiments, the cytokine comprises TNFα, IL-1α, IL-1β, IL-3, IL-6, IL-7, IL-8, IL-10, IL-18, IL-1RA, or a combination thereof. In some embodiments, the inflammatory cytokine may be an interleukin, such as IL-1, IL-6 or IL-8. In some embodiments, the inflammatory cytokine may be IL-1a. In some embodiments, the production of the inflammatory cytokines by a skin cell may be decreased by at least about 10%, 20%, 30%, 40%, 50%, 60%, 70%, 80%, 90%, 100%, or more than 100% when the composition is applied compared to the skin or skin cell where the composition is not applied. In some embodiments, the skin cell may be a keratinocyte. In some embodiments, the skin cell may be a fibroblast. In some embodiments, cytokine production may be measured using an ELISA-based assay.

In some embodiments, a truncated elastin as provided herein may stimulate expression of antioxidant genes in a skin cell or skin of a subject. In some cases, a truncated elastin as provided herein may stimulate expression of one or more antioxidant genes selected from the group consisting of: SOD2, GPX2, GPX4, GSTK1, GSTZ1, GSTA4, GSTM2, CCS, GPX1, GLRX, PRDX5, PRDX6, and PRDX2. In some cases, mRNA expression may be measured (e.g., by microarray, RNA sequencing, and the like)

In some embodiments, a truncated elastin as provided herein may reduce expression of pro-apoptotic genes in skin cells or the skin of a subject. In some cases, a truncated elastin as provided herein may reduce expression of one or more pro-apoptotic genes selected from the group consisting of: APAF1, BAK1, CASP7, CASP8, FADD, MCL1, and MET. In some cases, mRNA expression may be measured (e.g., by microarray, RNA sequencing, and the like).

In some embodiments, disclosed herein is a method of increasing viability of skin cells, the method comprising the step of applying a non-naturally occurring elastin or composition comprising non-naturally occurring elastin to the skin or the skin cell of a subject. In some embodiments, the viability of skin cells may be increased by at least about 10%, 20%, 30%, 40%, 50%, 60%, 70%, 80%, 90%, 100%, or more than 100% when the composition is applied compared to the skin or skin cell where the composition is not applied. In some embodiments, the skin cell may be a keratinocyte. In some embodiments, the skin cell may be a fibroblast.

In some embodiments, disclosed herein is a method of protecting skin cells against the effects of exposure to urban dust, the method comprising the step of applying a non-naturally occurring elastin or the composition comprising a non-naturally occurring elastin to the skin or the skin cell of a subject, wherein the viability of the skin cells is increased. In some embodiments, viability of the skin cells may be increased by at least about 10%, 20%, 30%, 40%, 50%, 60%, 70%, 80%, 90%, 100%, or more than 100% compared to untreated cells. In some embodiments, the skin cell may be a keratinocyte. In some embodiments, the skin cell may be a fibroblast. In some embodiments, the viability may be measured using an MTT assay.

In some embodiments, the composition has anti-oxidative capacity. In some embodiments, the anti-oxidative capacity may be measured using an oxygen radical absorbance capacity (ORAC) assay. In some embodiments, the antioxidative capacity may be measured in Trolox equivalent units. In some embodiments, the antioxidative capacity of the composition may be at least about 50 μM, 100 μM, 150 μM, 200 μM, 250 μM, or more than 250 μM Trolox equivalent units.

In some embodiments, the non-naturally occurring elastin may be encoded by a polynucleotide (e.g., a non-naturally occurring elastin; e.g., for expression in a host cell). The polynucleotides may encode for a full-length elastin or a truncated elastin. In various embodiments, the polynucleotide may comprise a polynucleotide according to any one of SEQ ID NO: 4, SEQ ID NO: 6, SEQ ID NO: 9, SEQ ID NO: 11, SEQ ID NO: 12, SEQ ID NO: 14, SEQ ID NO: 16, SEQ ID NO: 18, or a homolog thereof (e.g., having at least 80%, at least 85%, at least 90%, at least 95%, or at least 98% sequence identity thereto). In some cases, the polynucleotide may be codon optimized (e.g., for expression in a host cell).

The polynucleotides may be, in one aspect, contained within a vector (e.g., to transform host cells). The polynucleotides may further comprise nucleic acids that encode enzymes that permit the host organism to grow in the presence of a selection agent. The selection agents may include certain sugars, including galactose containing sugars, or antibiotics, including ampicillin, hygromycin, G418 and others. Enzymes that are used to confer resistance to the selection agent may include β-galactosidase.

In one aspect, host cells that express the disclosed polynucleotides (and the polypeptides encoded by said polynucleotides) are provided. In some cases, the host cell may comprise at least one copy of a heterologous nucleic acid sequence (e.g., encoding a polypeptide described herein). Host cells can be any host cell including gram negative bacterial cells, gram positive bacterial cells, yeast cells, insect cells, mammalian cells, plant cells, or any other cells used to express exogenous polynucleotides. In a specific embodiment, the host cell is *Escherichia coli*. In various aspects, the host cell may be capable of secreting the non-naturally occurring elastin extracellularly (e.g., into a culture medium).

Any necessary supplements besides carbon, nitrogen, and inorganic phosphate sources may also be included at appropriate concentrations introduced alone or as a mixture with another supplement or medium such as a complex nitrogen source. In certain embodiments, the medium further comprises one or more ingredients selected from: ammonium chloride, ammonium sulfate, calcium chloride, casamino acids, iron(II) sulfate, magnesium sulfate, peptone, potassium phosphate, sodium chloride, sodium phosphate, and yeast extract.

Another embodiment provides methods of producing a non-naturally occurring elastin. The method comprises inoculating a culture medium with a recombinant host cell comprising at least one copy of a heterologous nucleic acid sequence encoding the non-naturally occurring elastin, cultivating the host cell (e.g., culturing the host cell in a culture medium), and isolating the non-naturally occurring elastin from the host cell. In some cases, the method comprises culturing a recombinant host cell in a culture medium, wherein the recombinant host cell secretes the non-naturally occurring elastin into the culture medium, collecting the culture medium containing the non-naturally occurring elastin secreted thereto, and purifying and/or isolating the non-naturally occurring elastin from the culture medium (e.g., by centrifugation, filtration, and the like).

In another aspect, a process for fermentative preparation of a protein is provided. The process comprises the steps of:
a) culturing a recombinant bacterial cell in a medium comprising a magnesium salt, wherein the concentration of magnesium ions in the medium is at least about 6 mM, and wherein the bacterial cell comprises an exogenous gene encoding the protein; and
b) harvesting the protein from the medium.

The bacteria may be cultured continuously (as described, for example, in WO 05/021772) or discontinuously in a batch process (batch cultivation) or in a fed-batch or repeated fed-batch process for the purpose of producing the target protein. In some embodiments, protein production is conducted on a large-scale. Various large-scale fermentation procedures are available for production of recombinant proteins. Large-scale fermentations have at least 1,000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 20 liters in volumetric capacity.

For accumulation of the target protein, the host cell is cultured under conditions sufficient for accumulation of the target protein. Such conditions include, e.g., temperature, nutrient, and cell-density conditions that permit protein expression and accumulation by the cell. Moreover, such conditions are those under which the cell can perform basic cellular functions of transcription, translation, and passage of proteins from one cellular compartment to another for the secreted proteins, as are known to those skilled in the art.

The bacterial cells are cultured at suitable temperatures. For *E. coli* growth, for example, the typical temperature ranges from about 20° C. to about 39° C. In one embodiment, the temperature is from about 20° C. to about 37° C. In another embodiment, the temperature is at about 30° C. In one embodiment, the host cells, in the non-switched state or switched state, are cultivated at one temperature and switched to a different temperature to induce protein production. The host cells are cultivated first at one temperature to propagate the cells, then to induce protein production the cell are cultivated at a lower temperature. The first temperature may be 23°, 24°, 25°, 26°, 27°, 28°, 29°, 30°, 31°, 32°, 33°, 34°, 35°, 36°, or 37° C. The second temperature may be 20°, 21°, 22°, 23°, 24°, 25°, 26°, 27°, 28°, 29°, 30°, 31°, 32°, 33°, 34°, 35° or 36° C. The cultivation at the second temperature may be conducted between 1 hour and 100 hours, between 5 hours and 90 hours, between 5 hours and 80 hours, between 5 hours and 80 hours, between 5 hours and 70 hours, between 10 hours and 70 hours, between 15 hours and 70 hours, between 15 hours and 65 hours, between 15 hours and 60 hours, between 20 hours and 60 hours, between 20 hours and 55 hours, between 20 hours and 50 hours, between 24 hours and 50 hours, between 24 hours and 48 hours, between 30 hours and 50 hours, between 30 hours and 45 hours, or between 30 hours and 40 hours.

The pH of the culture medium may be any pH from about 5-9, depending mainly on the host organism. For E. coli, the pH may be from about 6.0 to about 7.4, about 6.2 to about 7.2, about 6.2 to about 7.0, about 6.2 to about 6.8, about 6.2 to about 6.6, about 6.4, or about 6.5.

For induction of gene expression, typically the cells are cultured until a certain optical density is achieved, e.g., an OD600 of about 1.1, at which point induction is initiated (e.g., by addition of an inducer, by depletion of a repressor, suppressor, or medium component, etc.) to induce expression of the exogenous gene encoding the target protein. In some embodiments, expression of the exogenous gene may be inducible by an inducer selected from, e.g., isopropyl-β-d-1-thiogalactopyranoside, lactose, arabinose, maltose, tetracycline, anhydrotetracycline, vavlycin, xylose, copper, zinc, and the like. The induction of gene expression can also be accomplished by decreasing the dissolved oxygen levels during fermentation. The dissolved oxygen levels of the fermentation during cell propagation may be between 10% and 30%. To induce gene expression the dissolved oxygen level may be reduced to below 10%, 9%, 8%, 7%, 6%, 5%, 4%, 3%, 2%, 1%, or 0%. In host cells, in either the physiological state or the switched state, protein production can be induced by lowering the temperature of the fermentation as disclosed herein.

EXAMPLES

Example 1. 25 kDa Truncated Human Elastin

A non-naturally occurring truncated human elastin without a His tag, linker, and/or thrombin cleavage site is disclosed below. The non-naturally occurring truncated human elastin was truncated relative to full-length human elastin (SEQ ID NO: 20). The codon-optimized nucleotide sequence encoding this elastin and the amino acid sequence are disclosed below. In SEQ ID NO: 4, the DsbA secretion tag is encoded by nucleotides 1-57 and encodes amino acids 1-19 of SEQ ID NO: 5. In SEQ ID NO: 4, the non-naturally occurring truncated human elastin sequence is encoded by nucleotides 58-927 and encodes amino acids 20-309 of SEQ ID NO: 5.

The codon-optimized nucleotide sequence encoding this non-naturally occurring truncated elastin is provided in SEQ ID NO 4.

```
                                              (SEQ ID NO: 4)
ATGAAAAAGATTTGGCTGGCGCTGGCTGGTTTAGTTTTAGCGTTTAGCGC

ATCGGCGGGTCCGCAACCTGGGGTTCCGTTAGGTTATCCGATTAAAGCAC

CGAAACTGCCCGGCGGTTATGGTCTGCCGTACACAACCGGTAAACTGCCG

TATGGTTATGGCCCGGGTGGAGTTGCGGGTGCAGCAGGTAAAGCGGGTTA

TCCTACCGGAACCGGTGTAGGTCCGCAGGCCGCTGCTGCCGCCGCCGCAA

AAGCAGCGGCTAAATTTGGCGCCGGAGCAGCGGGTGTTCTGCCTGGAGTT

GGTGGTGCGGGCGTGCCAGGGGTACCTGGTGCAATTCCGGGTATTGGTGG

TATTGCCGGTGTCGGCACCCCGGCCGCGGCAGCTGCGGCAGCGGCGGCTG

CCAAAGCTGCTAAATACGGTGCCGCGGCGGGTCTGGTGCCAGGAGGTCCG

GGTTTTGGTCCGGGAGTGGTTGGCGTGCCTGGCGCAGGCGTTCCTGGTGT
```

-continued
```
GGGCGTTCCAGGTGCAGGGATTCCTGTTGTGCCTGGTGCCGGTATTCCCG

GCGCGGCCGTTCCGGGGGTGGTTAGCCCGGAAGCCGCAGCGAAGGCTGCG

GCAAAGGCAGCAAAGTATGGCGCACGCCCAGGAGTCGGCGTGGGTGGTAT

CCCGACCTATGGGGTGGGCGCAGGGGGTTTTCCTGGTTTCGGCGTAGGTG

TAGGAGGTATACCGGGCGTGGCCGGTGTACCAGGGGTTGGTGGCGTCCCT

GGTGTTGGCGGTGTGCCAGGTGTTGGTATTTCACCGGAAGCACAGGCAGC

AGCCGCAGCTAAGGCAGCGAAATATGGTGCCGCCGGCGCAGGAGTTTTAG

GTGGGCTGGTTCCGGGCCCGCAGGCAGCTGTGCCGGGGGTTCCAGGCACC

GGTGGTGTCCCTGGAGTCGGTACGCCGTAA
```

The amino acid sequence of the 25 kDa non-naturally occurring truncated human elastin sequence including the DsbA secretion signal is disclosed in SEQ ID NO: 5.

```
                                              (SEQ ID NO: 5)
MKKIWLALAGLVLAFSASAGPQPGVPLGYPIKAPKLPGGYGLPYTTGKLP

YGYGPGGVAGAAGKAGYPTGTGVGPQAAAAAAAKAAAKFGAGAAGVLPGV

GGAGVPGVPGAIPGIGGIAGVGTPAAAAAAAAAKAAKYGAAAGLVPGGP

GFGPGVVGVPGAGVPGVGVPGAGIPVVPGAGIPGAAVPGVVSPEAAAKAA

AKAAKYGARPGVGVGGIPTYGVGAGGFPGFGVGVGGIPGVAGVPGVGGVP

GVGGVPGVGISPEAQAAAAAKAAKYGAAGAGVLGGLVPGPQAAVPGVPGT

GGVPGVGTP
```

The codon-optimized nucleotide sequence encoding the non-naturally occurring truncated human elastin without the DsbA secretion tag is provided in SEQ ID NO: 6.

```
                                              (SEQ ID NO: 6)
GGTCCGCAACCTGGGGTTCCGTTAGGTTATCCGATTAAAGCACCGAAACT

GCCCGGCGGTTATGGTCTGCCGTACACAACCGGTAAACTGCCGTATGGTT

ATGGCCCGGGTGGAGTTGCGGGTGCAGCAGGTAAAGCGGGTTATCCTACC

GGAACCGGTGTAGGTCCGCAGGCCGCTGCTGCCGCCGCCGCAAAAGCAGC

GGCTAAATTTGGCGCCGGAGCAGCGGGTGTTCTGCCTGGAGTTGGTGGTG

CGGGCGTGCCAGGGGTACCTGGTGCAATTCCGGGTATTGGTGGTATTGCC

GGTGTCGGCACCCCGGCCGCGGCAGCTGCGGCAGCGGCGGCTGCCAAAGC

TGCTAAATACGGTGCCGCGGCGGGTCTGGTGCCAGGAGGTCCGGGTTTTG

GTCCGGGAGTGGTTGGCGTGCCTGGCGCAGGCGTTCCTGGTGTGGGCGTT

CCAGGTGCAGGGATTCCTGTTGTGCCTGGTGCCGGTATTCCCGGCGCGGC

CGTTCCGGGGGTGGTTAGCCCGGAAGCCGCAGCGAAGGCTGCGGCAAAGG

CAGCAAAGTATGGCGCACGCCCAGGAGTCGGCGTGGGTGGTATCCCGACC

TATGGGGTGGGCGCAGGGGGTTTTCCTGGTTTCGGCGTAGGTGTAGGAGG

TATACCGGGCGTGGCCGGTGTACCAGGGGTTGGTGGCGTCCCTGGTGTTG

GCGGTGTGCCAGGTGTTGGTATTTCACCGGAAGCACAGGCAGCAGCCGCA

GCTAAGGCAGCGAAATATGGTGCCGCCGGCGCAGGAGTTTTAGGTGGGCT

GGTTCCGGGCCCGCAGGCAGCTGTGCCGGGGGTTCCAGGCACCGGTGGTG

TCCCTGGAGTCGGTACGCCGTAA
```

The amino acid sequence of the non-naturally occurring truncated human elastin without the DsbA secretion tag is disclosed in SEQ ID NO: 7.

(SEQ ID NO: 7)
GPQPGVPLGYPIKAPKLPGGYGLPYTTGKLPYGYGPGGVAGAAGKAGYPT

GTGVGPQAAAAAAAKAAAKFGAGAAGVLPGVGGAGVPGVPGAIPGIGGIA

GVGTPAAAAAAAAAAKAAKYGAAAGLVPGGPGFGPGVVGVPGAGVPGVGV

PGAGIPVVPGAGIPGAA VPGVVSPEAAAKAAAKAAKYGARPGVGVGGIP

TYGVGAGGFPGFGVGVGGIPGVAGVPGVGGVPGVGGVPGVGISPEAQAAA

AAKAAKYGAAGAGVLGGLVPGPQAAVPGVPGTGGVPGVGTP

The polynucleotide of SEQ ID NO: 4 was synthesized by Gen9 DNA (now Ginkgo Bioworks) internal DNA synthesis. Overlaps between the pET28 vector and SEQ ID NO: 4 and SEQ ID NO: 6 were designed to be between 20 and 30 bp long and added using PCR with the enzyme PRIME-STAR® GXL polymerase (takarabio.com/products/pcr/gc-rich-pcr/primestar-gxl-dna-polymerase). The opened pET28a vector and insert DNA (SEQ ID NO: 4) were then assembled together into the final plasmid using IN-FUSION® Cloning (takarabio.com/products/cloning/in-fusion-cloning). Sequence of plasmid was then verified through Sanger sequencing through Genewiz (genewiz.com/en).

The transformed cells were cultivated in minimal media and frozen in 1.5 mL aliquots with vegetable glycerin at a ratio of 50:50 of cells to glycerin. One vial of this frozen culture was revived in 50 mL of minimal media overnight at 37° C., 200 rpm. Cells were transferred into 300 mL of minimal media and grown for 6-9 hours to reach an OD600 of 5-10.

Minimal media used in this example and throughout this disclosure is prepared as follows:
1) Autoclave 5 L of 550 g/kg Glucose syrup at concentration in DI water. (VWR, product #97061-170).
2) Autoclave in 3946 mL of DI water:
20 g $(NH_4)_2HPO_4$ (VWR, product #97061-932).
66.5 g $KH_2PO_4$ (VWR, product #97062-348).
22.5 g $H_3C_6H_5O_7$ (VWR, product #BDH9228-2.5KG).
8.85 g $MgSO_4 \cdot 7H_2O$ (VWR, product #97062-134).
10 mL of 1000× Trace metals formulation (Table 3).
After autoclaving, add
118 g of (1) to (2)
5 mL of 25 mg/mL Kanamycin Sulfate (VWR-V0408)
Use 28% $NH_4OH$ (VWR, product #BDH3022) to adjust pH to 6.1.

TABLE 3

Trace metals formulation

Ferrous Sulfate Heptahydrate, 27.8 g/L (Spectrum, 7782-63-0)
Zinc Sulfate heptahydrate, 2.88 g/L (Spectrum, 7446-20-0)
Calcium chloride dihydrate, 2.94 g/L (Spectrum, 2971347)
Sodium molybdate dihydrate, 0.48 g/L (Spectrum, 10102-40-6)
Manganese chloride tetrahydrate, 1.26 g/L (Spectrum, 13446-34-9)
Sodium selenite, 0.35 g/L (Spectrum, 10102-18-8)
Boric acid, 0.12 g/L (Spectrum, 10043-35-3

The fermentations were performed at various temperatures ranging from 25° to 28° C. For some fermentations, the temperature of the fermentation was maintained at a constant temperature. For other fermentations, the temperature of the fermentations was maintained for a desired period of time and when cell densities of OD600 of 10-20 were reached, the temperature was reduced to induce protein production. Typically, the temperature was reduced from 28° C. to 25° C.; the fermentation at 25° C. was continued for 40-60 hours.

The purified non-naturally occurring truncated elastin was analyzed on an SDS-PAGE gel and a clear band was observed at the expected size of 25 kilodaltons in a location void of a band in the control strain.

Example 2. 21 kDa Truncated Human Elastin

A non-naturally occurring truncated human elastin is synthesized according to the method of Example 1.

The amino acid sequence of a 21 kDa non-naturally occurring truncated human elastin truncated at the N-terminal relative to a full-length human elastin (SEQ ID NO: 20) is disclosed in SEQ ID NO: 8. The 21 kDa non-naturally occurring truncated human elastin has amino acids 1-522 deleted from the full length human elastin (SEQ ID NO: 20).

(SEQ ID NO: 8)
GPGGVAAAAKSAAKVAAKAQLRAAAGLGAGIPGLGVGVGVPGLGVGAGVP

GLGVGAGVPGFGAGADEGVRRSLSPELREGDPSSSQHLPSTPSSPRVPGA

LAAAKAAKYGA AVPGVLGGLGALGGVGIPGGVVGAGPAAAAAAAKAAAK

AAQFGLVGAAGLGGLGVGGLGVPGVGGLGGIPPAAAAKAAKYGAAGLGGV

LGGAGQFPLGGVAARPGFGLSPIFPGGACLGKACGRKRK

The codon optimized polynucleotide sequence encoding the 21 kDa non-naturally occurring truncated human elastin is disclosed in SE ID NO: 9.

(SEQ ID NO: 9)
GGTCCGGGCGGTGTCGCAGCAGCAGCTAAAAGCGCGGCGAAAGTTGCGGC

CAAAGCCCAACTGCGCGCCGCCGCGGGCCTCGGTGCAGGTATTCCGGGGC

TGGGTGTCGGAGTTGGAGTCCCGGGTTTGGGCGTGGGCGCGGGAGTTCCG

GGACTGGGAGTGGGTGCCGGAGTTCCTGGCTTTGGTGCAGGCGCAGATGA

AGGTGTTCGTCGTAGCCTGAGTCCGGAACTGCGTGAAGGTGATCCGAGTA

GCAGCCAGCATCTGCCGAGCACCCCGAGCAGCCCGCGTGTTCCGGGTGCA

TTAGCTGCAGCAAAAGCCGCCAAGTATGGTGCAGCCGTGCCGGGCGTCTT

AGGTGGTCTGGGCGCCCTGGGTGGTGTAGGCATTCCGGGAGGTGTTGTGG

GTGCAGGACCGGCCGCCGCAGCTGCGGCCGCCAAAGCAGCTGCAAAAGCG

GCCCAGTTTGGTTTAGTGGGCGCCGCAGGTTTAGGCGGTTTAGGTGTGGG

TGGACTGGGTGTACCTGGCGTAGGCGGTCTGGGTGGAATTCCGCCCGCAG

CGGCCGCGAAAGCGGCAAAATATGGCGCGGCAGGCCTGGGCGGCGTGCTG

GGTGGGGCAGGTCAGTTTCCGCTGGGCGGGGTTGCCGCACGTCCGGGATT

TGGTCTGAGCCCGATTTTCCCTGGCGGCGCATGTCTGGGTAAAGCATGTG

GTCGTAAACGTAAATAA

The cells are cultivated and the polynucleotide of SEQ ID NO: 9 is expressed as disclosed in Example 1.

Example 3. 60 kDa Truncated Human Elastin

The amino acid sequence of a 60.3 kDa non-naturally occurring truncated human elastin truncated internally relative to a full-length human elastin (SEQ ID NO: 20) is disclosed in SEQ ID NO: 10. The 60.3 kDa non-naturally occurring truncated human elastin has amino acids 461-527 deleted from the full length human elastin (SEQ ID NO: 20).

(SEQ ID NO: 10)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQAAAAAKAAKYGAAGAGVLGGLVPGPQAAVPGVPG

TGGVPGVGTPAAAAKSAAKVAAKAQLRAAAGLGAGIPGLGVGVGVPGLGV

GAGVPGLGVGAGVPGFGAGADEGVRRSLSPELREGDPSSSQHLPSTPSSP

RVPGALAAAKAAKYGAAVPGVLGGLGALGGVGIPGGVVGAGPAAAAAAAK

AAAKAAQFGLVGAAGLGGLGVGGLGVPGVGGLGGIPPAAAAKAAKYGAAG

LGGVLGGAGQFPLGGVAARPGFGLSPIFPGGACLGKACGRKRK

The codon optimized polynucleotide sequence encoding the 60.3 kDa non-naturally occurring truncated human elastin is disclosed in SEQ ID NO: 11.

(SEQ ID NO: 11)
GGTGGCGTACCAGGCGCAATTCCTGGGGGTGTCCCAGGCGGTGTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGGC

AGCAGCCGCAGCTAAGGCAGCGAAATATGGTGCCGCCGGCGCAGGAGTTT

TAGGTGGGCTGGTTCCGGGCCCGCAGGCAGCTGTGCCGGGGGTTCCAGGC

ACCGGTGGTGTCCCTGGAGTCGGTACGCCGGCAGCAGCAGCTAAAAGCGC

GGCGAAAGTTGCGGCCAAAGCCCAACTGCGCGCCGCCGCGGGCCTCGGTG

CAGGTATTCCGGGGCTGGGTGTCGGAGTTGGAGTCCCGGGTTTGGGCGTG

GGCGCGGGAGTTCCGGGACTGGGAGTGGGTGCCGGAGTTCCTGGCTTTGG

TGCAGGCGCAGATGAAGGTGTTCGTCGTAGCCTGAGTCCGGAACTGCGTG

AAGGTGATCCGAGTAGCAGCCAGCATCTGCCGAGCACCCCGAGCAGCCCG

CGTGTTCCGGGTGCATTAGCTGCAGCAAAAGCCGCCAAGTATGGTGCAGC

CGTGCCGGGCGTCTTAGGTGGTCTGGGCGCCCTGGGTGGTGTAGGCATTC

CGGGAGGTGTTGTGGGTGCAGGACCGGCCGCCGCAGCTGCGGCCGCCAAA

GCAGCTGCAAAAGCGGCCCAGTTTGGTTTAGTGGGCGCCGCAGGTTTAGG

CGGTTTAGGTGTGGGTGGACTGGGTGTACCTGGCGTAGGCGGTCTGGGTG

GAATTCCGCCCGCAGCGGCCGCGAAAGCGGCAAAATATGGCGCGGCAGGC

CTGGGCGGCGTGCTGGGTGGGGCAGGTCAGTTTCCGCTGGGCGGGGTTGC

CGCACGTCCGGGATTTGGTCTGAGCCCGATTTTCCCTGGCGGCGCATGTC

TGGGTAAAGCATGTGGTCGTAAACGTAAATAA

The cells are cultivated and the polynucleotide of SEQ ID NO: 11 is expressed as disclosed in Example 1.

Example 4. Effect of Truncated Elastin on Fibroblast Cell Viability, Procollagen Synthesis, and Tropoelastin Synthesis A human fibroblast cell culture is used to assess the ability of the non-naturally occurring truncated human elastin molecule of Example 1 to affect procollagen and tropoelastin synthesis. The human fibroblast cell culture is also used to determine the viability of the human fibroblast cells after exposure to the truncated elastin.

A stock solution of 2% w/w truncated elastin is prepared from the truncated elastin of Example 1. Aliquots from the 2% stock truncated elastin solution are then used in the experiments described below.

Preparation of Fibroblasts

Fibroblasts are seeded into the individual wells of a 24-well plate in 0.5 mL of Fibroblast Growth Media (FGM) and incubated overnight at 37±2° C. and 5±1% $CO_2$. On the following day, the media is removed via aspiration to eliminate any non-adherent cells and replaced with 0.5 mL of fresh FGM. The cells are grown until confluent, with a media change every 48 to 72 hours. Upon reaching confluency the cells are treated for 24 hours with Dulbecco's Modified Eagle Medium (DMEM) supplemented with 1.5% Fetal Bovine Serum (FBS) to wash out any effects from the growth factors included in the normal culture media. After the 24-hour wash out period the cells are treated with the truncated elastin at specified concentrations dissolved in FGM with 1.5% FBS. Transforming Growth Factor Beta (TGF-β) (20 ng/mL) is used as a positive control for collagen and elastin synthesis. Untreated cells (negative controls) receive only DMEM with 1.5% FBS. The cells are incubated for 48 hours and at the end of the incubation period, cell culture media is collected and either stored frozen (−75° C.) or assayed immediately. Materials are tested in triplicate.

MTT Assay

The MTT (3-(4,5-Dimethylthiazol-2-yl)-2,5-diphenyltetrazolium bromide, a tetrazole) assay is a colorimetric assay used to determine the metabolic activity of cells. Changes in cell number are assessed via an MTT assay. When cells are exposed to MTT, reduction of MTT by mitochondria in viable cells results in the formation of insoluble purple formazin crystals that are extracted from the cells with isopropanol and quantified spectrophotometrically. Non-living cells cannot reduce MTT and therefore cannot produce the purple formazin crystals. The intensity of the purple color is directly proportional to the number of living cells (metabolically active cells). The intensity of the purple color is directly proportional to the metabolic activity of the cells and is inversely proportional to the toxicity of the test material.

After the 2-day incubation discussed above, the cell culture medium is removed (see above) and the fibroblasts are washed twice with Phosphate Buffered Saline (PBS) to remove any remaining elastin molecules. After the final wash, 500 µL of DMEM supplemented with 0.5 mg/ml MTT is added to each well and the cells are incubated for 1 hour at 37±2° C. and 5±1% $CO_2$. After the incubation, the DMEM/MTT solution is removed and the cells are washed again once with PBS and then 0.5 mL of isopropyl alcohol is added to the well to extract the purple formazin crystals. Two hundred microliters of the isopropyl extracts is transferred to a 96-well plate and the plate read at 540 nm using isopropyl alcohol as a blank.

The mean MTT absorbance value for the negative control cells is calculated and used to represent 100% cell viability. The individual MTT absorbance values from the cells undergoing the various treatments are then divided by the mean value for the negative control cells and expressed as a percent to determine the change in cell viability caused by each treatment.

Procollagen Synthesis

Fibroblasts are the main source of the extracellular matrix peptides, including the structural proteins collagen and elastin. Procollagen is a large peptide synthesized by fibroblasts in the dermal layer of the skin and is the precursor for collagen. As the peptide is processed to form a mature collagen protein, the propeptide portion is cleaved off (type I C-peptide). Both the mature collagen protein and the type I C-peptide fragment are then released into the extracellular environment. As collagen is synthesized, the type I C-peptide fragment accumulates into the tissue culture medium. Since there is a 1:1 stoichiometric ratio between the two parts of the procollagen peptide, assaying for type I C-peptide reflects the amount of collagen synthesized. Type I C-peptide can be assayed via an Enzyme Linked Immunosorbent Assay (ELISA)-based method.

A series of type I C-peptide standards are prepared ranging from 0 ng/mL to 640 ng/mL. Next, an ELISA microplate is prepared by removing any unneeded strips from the plate frame followed by the addition of 100 µL of peroxidase-labeled anti-procollagen type I-C peptide antibody to each well used in the assay. Twenty (20) µL of either sample (collected tissue culture media) or standard is then added to appropriate wells and the microplate is covered and allowed to incubate for 3±0.25 hours at 37° C. After the incubation, the wells are aspirated and washed three times with 400 µL of wash buffer. After the last wash is removed, 100 µL of peroxidase substrate solution (hydrogen peroxide+tetramethylbenzidine as a chromogen) is added to each well and the plate is incubated for 15±5 minutes at room temperature. After the incubation, 100 µL of stop solution (1 N sulfuric acid) is added to each well and the plate is read using a microplate reader at 450 nm.

To quantify the amount of each substance present, a standard curve is generated using known concentrations of each substance. A regression analysis is performed to establish the line that best fits these data points. Absorbance values for the test materials and untreated samples are used to estimate the amount of each substance present in each sample.

Elastin Synthesis

Elastin is the main component of a network of elastic fibers that give tissues their ability to recoil after a transient stretch. This protein is released by fibroblasts (soluble elastin) into the extracellular space where it is then cross-linked to other elastin proteins to form an extensive network of fibers and sheets (insoluble elastin). Soluble elastin can be readily measured from cell culture medium via an ELISA-based method.

Soluble α-elastin is dissolved in 0.1 M sodium carbonate (pH 9.0) at a concentration of 1.25 µg/mL. 150 µL of this solution is then applied to the wells of a 96-well Maxisorp Nunc plate, and the plate is incubated overnight at 4° C. On the following day, the wells are saturated with PBS containing 0.25% Bovine Serum Albumin (BSA) and 0.05% TWEEN® 20. The plate is then incubated with this blocking solution for 1 hour at 37° C. and then washed two times with PBS containing 0.05% TWEEN® 20.

A set of α-elastin standards is generated ranging from 0 to 100 ng/ml. 180 µL of either standard or truncated elastin is then transferred to a 650 µL microcentrifuge tube. An anti-elastin antibody solution is prepared (the antibody is diluted 1:100 in PBS containing 0.25% BSA and 0.05% TWEEN® 20) and 20 µL of the solution is added to the tube. The tubes are then incubated overnight at 4+2° C. On the following day, 150 µL is transferred from each tube to the 96-well elastin ELISA plate, and the plate is incubated for 1 hour at room temperature. The plate is then washed 3 times with PBS containing 0.05% TWEEN® 20. After washing, 200 µL of a solution containing a peroxidase linked secondary antibody diluted in PBS containing 0.25% BSA and 0.05% TWEEN® 20 is added, and the plate is incubated for 1 hour at room temperature. After washing the plate three times, 200 µL of a substrate solution is added and the plate is incubated for 10 to 30 minutes in the dark at room temperature. After this final incubation, the plate is read at 460 nm using a plate reader.

Example 5. Effect of Truncated Elastin on Keratinocyte Proliferation and UVB Protection A human keratinocyte cell culture model is used to assess the ability of the test materials to exert an effect on cell proliferation. In addition, the impact of the test materials on the cell viability after an exposure to UVB is also assessed.

A stock solution of 2% w/w truncated elastin is prepared from the truncated elastin of Example 1. Aliquots from the 2% stock truncated elastin solution are then used in the experiments described below.

This study is conducted in two parts. In the first part, cultured keratinocytes are incubated with the test materials for 48 hours, after which, changes in the number of viable cells are assessed using an MTT assay. In the second part of the study, cultured keratinocytes are irradiated with UVB and then treated with the test materials for 48 hours. At the end of the 48 hour period, the number of viable cells is again assessed via an MTT assay.

Changes in cell number of viable cells can be determined using an MTT (3-(4,5-Dimethylthiazol-2-yl)-2,5-diphenyltetrazolium bromide, a tetrazole) assay. The MTT assay is a colorimetric analysis of the metabolic activity of the cell, which is a reflection of the number of viable cells. Reduction of MTT by mitochondria in viable cells results in the formation of insoluble purple formazin crystals that are extracted from the cells with isopropanol and quantified spectrophotometrically. The intensity of the purple color is directly proportional to the number of metabolically active cells.

Proliferation Assay

For the proliferation assay, the keratinocytes are seeded into 96-well plates without growth factors and incubated for 24 hours at 37±2° C. and 5±1% CO2. After this initial incubation, the media is replaced with media supplemented with the test materials. Normal media (with growth factors) is used as a positive control. After the addition of the test materials, the cells are cultured for 48 hours, as described above. At the end of the incubation period, changes in the number of viable cells are determined using an MTT assay.

UVB Protection Assay

For the UVB protection assay, the keratinocytes are seeded into 96-well plates using normal media and incubated for 24 hours at 37±2° C. and 5±1% $CO_2$. After this initial incubation, the media is replaced with 100 µL of phosphate buffered saline (PBS) and the cells are exposed to UVB (40 mJ/cm$^2$). After the UVB exposure, the PBS is replaced with fresh media supplemented with the test materials (ascorbic acid at 100 µg/mL serves as the positive control) and the cells are cultured for 48 hours at 37±2° C. and 5±1% $CO_2$. At the end of the 48 hour incubation, cell viability is determined using an MTT assay.

Example 6. Effect of Truncated Elastin on Thymine Dimer Formation

Upon exposure to ultraviolet radiation, the thymine dimer (TT dimer) content in DNA present in cells increases. Increases in TT dimer formation are correlated with skin damage and certain types of cell proliferative diseases including skin cancer.

The truncated elastin of Example 1 is tested to determine if it can reduce TT dimer formation in human epidermal keratinocytes. Human keratinocytes are seeded into 12-well plates using normal media and incubated for 24 hours at 37±2° C. and 5±1% $CO_2$. After this initial incubation, the media is replaced with 100 µL of phosphate buffered saline (PBS) and the cells are exposed to UVB (25 mJ/cm$^2$). After the UVB exposure, the PBS is replaced with fresh media supplemented with the test materials or Trolox (100 µg/ml, a positive control) and the cells are cultured overnight at 37±2° C. and 5±1% $CO_2$. At the end of the incubation, cellular DNA is extracted and assayed for thymine dimer content using an ELISA-based method.

After the overnight incubation, the cell culture media is removed from the wells and replaced with 200 µL of PBS and 20 µL of Proteinase K. After swirling the plate to mix the PBS and Proteinase K, 200 µL of buffer AL is added to each well. After again swirling the plate to mix the reagents, the plates are incubated for 10 minutes at 55±2° C. After cooling the plate to room temperature, the DNA is precipitated by the addition of 200 µL of 100% ethanol. The precipitated DNA mixtures are then transferred to DNEASY® Spin Columns in 2 mL collection tubes and centrifuged at 8,000 RPM for 1 minute. The flow through and collection tubes are discarded, and 500 µL of Wash Buffer One is added to the spin column and the column is placed into a new collection tube and centrifuged at 8,000 RPM for 1 minute. The flow through and collection tube are again discarded, and 500 µL of Wash Buffer Two is added to the spin column, and the column is placed into a new collection tube and centrifuged at 14,000 RPM for 3 minutes. The spin column is then placed into a new 1.5 mL centrifuge tube and 110 µL of ultrapure water is added to the column. The column is incubated for 1 minute at room temperature and then centrifuged at 8,000 RPM for 1 minute.

Extracted DNA is quantified via a fluorometric assay. A 2 µL aliquot of the DNA sample is mixed with 100 µL Tris-EDTA (TE) buffer in a 96-well plate. A series of DNA standards is also transferred to wells in a 96-well plate (in duplicate). Finally, 100 µL of dilute CYQUANT® Green dye is added to each well, and the fluorescence intensity of each well is determined using an excitation wavelength of 480 nm and an emission wavelength of 520 nm.

Thymine Dimer Detection can be determined using an OxiSelect™ UV-Induced DNA Damage ELISA Kit.

Aliquots of genomic DNA samples or standards are converted to single stranded DNA by incubating the samples at 95° C. for 10 minutes and then chilling on ice. 100 µL of each sample or standard is transferred to a DNA binding ELISA plate and incubated overnight at 4° C. On the following day, the wells are rinsed once with 100 µL of PBS and then blocked with 150 µL of Assay Diluent for one hour at room temperature. After removing the Assay Diluent, 100 µL of anti-CPD antibody is added to each well and the plate is incubated for one hour at room temperature. After this incubation, the plate is washed three times with 250 µL of wash buffer per well, and then 150 µL of Blocking Reagent is added to the plate. The plate is blocked again for one hour at room temperature and then washed three times as described before. 100 µL of Secondary Antibody is then added to each well, and the plate is incubated for 1 hour at room temperature. After washing the plate again, 100 µL of substrate is added to each well and the plate is incubated for 5-20 minutes to allow for color generation in the plate. The color generation reaction is stopped by the addition of 100 µL of stop solution, and the plate is read at 460 nm using a plate reader.

To quantify the amount of DNA present, a standard curve is generated using known concentrations of DNA and their respective fluorescence intensity (measured in RFUs or relative fluorescence units). A regression analysis is performed to establish the line that best fits the data points. The Relative Fluorescence Units (RFU) for each unknown sample is then used to estimate the amount of DNA.

A series of DNA standards with known amounts of thymine dimer content is used to generate a standard curve. This standard curve is used to determine the amount of DNA damage in the sample DNA. Means for each treatment group are calculated and compared using an ANOVA.

Example 7. Protective Effect of Truncated Human Elastin on Fibroblasts

The effect of non-naturally occurring truncated human elastin on fibroblast cell viability, procollagen synthesis, and elastin synthesis is determined according to the methods of Example 4.

The effect of non-naturally occurring truncated human elastin on Keratinocyte proliferation and UVB protection is determined according to the methods of Example 5.

The effect of non-naturally occurring truncated human elastin on thymine dimer formation after exposure to UV radiation is determined according to the methods of Example 6.

Example 8. Effect of Truncated Elastin on Inflammatory Cytokines

Keratinocytes and dermal fibroblasts play an important role in the immune response of the skin. In response to irritating chemicals or UV radiation (pro-inflammatory/pro-irritation stimuli), keratinocytes can release a vast array of cytokines. These cytokines are thought to help engage immune cells to the site of inflammation. Cytokines released by the keratinocytes include TNFα, IL-1α, IL-1β, IL-3, IL-6, IL-7, IL-8, IL-10, IL-18, and IL-1RA.

The testing model used for this study is the MatTek EPIDERM®. This skin model consists of normal human-derived epidermal keratinocytes that have been cultured to form a multilayered, highly differentiated model of the human epidermis. Ultrastructural analysis has revealed the presence of keratohyalin granules, tonofilament bundles, desmosomes, and a multi-layered stratum corneum containing intercellular lamellar lipid layers arranged in patterns characteristic of in vivo epidermis. Markers of mature epidermis specific differentiation, such as pro-filaggrin, the K1/K10 cytokeratin pair, involucrin, and type I epidermal transglutaminase, have been localized in this model. The MatTek EPIDERM® is also mitotically and metabolically active.

The MatTek EPIDERM® tissues are used to assess the ability of various test materials to inhibit the release of the inflammatory mediator IL-1α. Test materials are compared to an over the counter topical hydrocortisone preparation (positive control) as well as to untreated tissues (negative control 1) and untreated, non-inflamed tissues (negative control 2). This test is also used to assess the viability of the tissues after exposure to the test materials.

IL-1α, IL-6, and IL-8 are synthesized and stored in keratinocytes and have been identified as mediators of skin irritation and inflammation. Release of these cytokines can be directly measured in tissue culture media via a colorimetric based enzyme linked immunosorbent assay (ELISA). Briefly, antibodies covalently linked to a solid support can bind IL-1α, IL-6, or IL-8 present in spent culture media samples. A second antibody that is covalently attached to an acetylcholinesterase enzyme can in turn detect the specific bound cytokines. Upon addition of an appropriate color substrate, the acetylcholinesterase enzyme can generate a colored end product that can be measured spectrophotometrically.

MatTek EPIDERM® Tissues are purchased from MatTek corporation and stored at 4° C. until used. Prior to use, the tissues to be used are removed from the agarose-shipping tray and placed into a 6-well plate containing 0.9 mL of hydrocortisone free assay medium (37±2° C.). The tissues are allowed to incubate overnight at 37±2° C. and 5±1% $CO_2$. After this initial incubation, the assay medium is replaced with 0.9 mL of fresh hydrocortisone free medium (37±2° C.). Three tissues are prepared for each test material.

An inflammatory response in the tissues is initiated via UV irradiation (UVB). A UV lamp is used to give a 300 $mJ/cm^2$ dose of UVB radiation to the tissues. Immediately after the application of the inflammatory stimuli, 50 µL or mg of test material is applied directly onto the surface of the tissue. An over the counter hydrocortisone cream is used as a positive control. For a negative control, tissues are exposed to the inflammatory stimuli but are not treated with any type of anti-inflammatory material. One additional set of tissues is left without exposure to the inflammatory stimuli to provide a baseline measurement for the cytokines. The tissues are incubated at 37±2° C. and 5±1% $CO_2$ for 24 hours after exposure to the inflammatory stimuli. After the 24 hour incubation, the cell culture medium is collected and stored at −75° C. until analyzed for cytokines.

The ELISA plates are prepared by diluting the appropriate capture antibody in PBS. Next, 100 µL of the diluted capture antibody is added to the wells of a 96-well ELISA plate and the plate is incubated overnight at room temperature. On the following day, the plate is washed three times with 300 µL wash buffer (0.05% TWEENR 20 in PBS) and then blocked by adding 300 µL of blocking buffer (1% BSA in PBS) to each well. The plate is incubated with the blocking buffer for at least one hour. After the incubation, the blocking buffer is removed, and the plate is washed three times as described above.

A series of standards is prepared and 100 µL of each of these standards is dispensed into two wells (duplicates) in the appropriate 96-well plate. Subsequently, 100 µL of each sample is added to additional wells and the plate was incubated for two hours at room temperature. After the incubation, the plate is washed three times as described above. Once the last wash is removed, 100 µL of a biotin conjugated detection antibody is added. After incubating the plate for two hours at room temperature, the plate is washed again as described above. 100 µL of HRP-streptavidin is then added to each well, and the plate is incubated for 20 minutes at room temperature. Next, 100 µL of substrate solution (hydrogen peroxide+tetramethylbenzidine as a chromagen) is added to each well. Once a sufficient level of color development occurs, 50 µL of stop solution (2 N sulfuric acid) is added to each well and the plate is read at 460 nm.

After the 24 hour incubation, the tissues are rinsed twice with at least 100 µL of phosphate buffered saline to remove the test material and then transferred to a 6-well plate containing 1.0 mL of assay medium supplemented with MTT (1 mg/mL) and allowed to incubate for 3±0.25 hours at 37±2° C. and 5±1% $CO_2$. After the incubation, the tissues are rinsed at least twice with 100 µL of phosphate buffered saline, blotted dry, and then placed into a 24-well plate containing 2 mL of isopropanol per well. The 24-well plate is covered and allowed to incubate at room temperature for at least 2 hours on a rocking platform to extract the reduced MTT from the tissues. After the extraction, a 200 µL sample of the isopropanol/MTT mixture is transferred to a 96-well plate, and the absorbance of the sample is read at 540 nm with a plate reader using 200 µL of isopropanol as the blank.

Example 9. Urban Dust Protection by Truncated Elastin

A keratinocyte cell culture model is used to assess the ability of truncated elastin to exert a protective effect by promoting cell survival after exposure to urban dust.

Human epidermal keratinocytes are pretreated with the test materials and then exposed to urban dust. At the end of the treatment period, changes in cell viability are determined via an MTT assay.

Keratinocytes are seeded into the individual wells of a 96-well plate in 100 μL of medium and incubated overnight at 37±2° C. and 5±1% $CO_2$. On the following day, the media is removed via aspiration to eliminate any non-adherent cells and replaced with 100 μL of fresh medium. The cells are grown until confluent, with a media change every 48 to 72 hours.

Pre-Treatment with Test Material Followed by Urban Dust Treatment

Test materials are prepared at 2× their final desired concentrations in cell culture media. Urban dust (NIST 1649B from Sigma Chemicals) is also prepared at 2× solutions. For the pretreatment, 50 μL of 2× test material is combined with 50 μL of culture media and the cells are incubated for 24 hours. At the end of the pretreatment period, the test material containing culture media is removed and replaced with 50 μL of 2× urban dust and 50 μL of media. Another set of cells is treated with media alone (non-dust exposed) and used as a reference control to represent 100% cell viability. The cells are then incubated for 24 hours and then subjected to an MTT assay to determine changes in cell viability.

At the end of the treatment period, the cell culture medium is removed, and the cells are washed with PBS. After the wash, 100 μL of cell culture media supplemented with 0.5 mg/mL MTT is added to each well and the cells are incubated for 30 minutes at 37±2° C. and 5±1% $CO_2$. After the incubation, the media/MTT solution is removed and the cells are washed again once with PBS and then 100 μL of isopropyl alcohol is added to the wells to extract the purple formazin crystals. The 96-well plate is then read at 540 nm using isopropyl alcohol as a blank.

The mean MTT absorbance value for the non-dust exposed cells is calculated and used to represent 100% value for cell number. The individual MTT values from the cells undergoing the various treatments is then divided by the mean value for the non-dust exposed cells and expressed as a percent to determine the change in cell number caused by each treatment.

Example 10. 23 kDa Truncated Human Elastin

A non-naturally occurring truncated human elastin without a His tag, linker, and thrombin cleavage site is disclosed below. The codon-optimized nucleotide sequence encoding this truncated elastin and the amino acid sequence are disclosed below. In SEQ ID NO: 12, the DsbA secretion tag is encoded by nucleotides 1-57 and encodes amino acids 1-19 of SEQ ID NO: 13. In SEQ ID NO: 12, the truncated elastin sequence is encoded by nucleotides 58-843 and encodes amino acids 20-281 of SEQ ID NO: 13.

The codon-optimized nucleotide sequence encoding this non-naturally occurring truncated elastin is provided in SEQ ID NO 12.

(SEQ ID NO: 12)
ATGAAAAAGATTTGGCTGGCGCTGGCTGGTTTAGTTTTAGCGTTTAGCGC

ATCGGCGGCCGGTCTGGGTGGCGTGCCTGGCGTTGGTGGCCTGGGCGTTA

GCGCCGGTGCAGTTGTTCCGCAGCCTGGTGCGGGTGTTAAACCGGGTAAA

GTTCCTGGTGTTGGTCTGCCTGGTGTTTATCCAGGCGGTGTTCTGCCAGG

TGCGCGTTTTCCTGGCGTGGGTGTTCTGCCGGGTGTTCCGACCGGTGCAG

GCGTGAAACCGAAAGCACCAGGTGTTGGTGGTGCATTTGCAGGTATTCCA

GGTGTGGGTCCGTTTGGTGGTCCGCAGCCAGGCGTTCCGCTGGGTTATCC

GATTAAAGCACCGAAACTGCCTGGCGGTTATGGTCTGCCGTATACCACCG

GTAAACTGCCGTATGGTTATGGCCCTGGCGGTGTTGCCGGTGCGGCAGGT

AAAGCAGGCTATCCGACCGGTACCGGTGTAGGTCCGCAGGCAGCAGCCGC

AGCAGCGGCAAAAGCAGCAGCGAAATTTGGTGCGGGTGCAGCCGGTGTGC

TGCCAGGCGTAGGTGGCGCTGGTGTACCTGGTGTCCCTGGCGCAATTCCA

GGTATTGGCGGTATTGCAGGCGTTGGTACTCCGGCAGCTGCAGCCGCTGC

CGCAGCCGCAGCTAAAGCAGCCAAATATGGTGCAGCGGCAGGCCTGGTTC

CTGGCGGTCCAGGTTTTGGTCCGGGTGTTGTTGGCGTCCCAGGTGCCGGT

GTGCCTGGTGTGGGTGTTCCAGGTGCGGGTATTCCGGTTGTTCCTGGCGC

AGGCATTCCGGGTGCCGCAGTTCCGGGTGTAGTTAGCCCGGAATAA

The amino acid sequence of the 23 kDa non-naturally occurring truncated human elastin sequence including the DsbA secretion signal is disclosed in SEQ ID NO: 13.

(SEQ ID NO: 13)
MKKIWLALAGLVLAFSASAAGLGGVPGVGGLGVSAGAVVPQPGAGVKPGK

VPGVGLPGVYPGGVLPGARFPGVGVLPGVPTGAGVKPKAPGVGGAFAGIP

GVGPFGGPQPGVPLGYPIKAPKLPGGYGLPYTTGKLPYGYGPGGVAGAAG

KAGYPTGTGVGPQAAAAAAAKAAAKFGAGAAGVLPGVGGAGVPGVPGAIP

GIGGIAGVGTPAAAAAAAAAKAAKYGAAAGLVPGGPGFGPGVVGVPGAG

VPGVGVPGAGIPVVPGAGIPGAAVPGVVSPE

The codon-optimized nucleotide sequence encoding the non-naturally occurring truncated human elastin without the DsbA secretion tag elastin is provided in SEQ ID NO: 14.

(SEQ ID NO: 14)
GCCGGTCTGGGTGGCGTGCCTGGCGTTGGTGGCCTGGGCGTTAGCGCCGG

TGCAGTTGTTCCGCAGCCTGGTGCGGGTGTTAAACCGGGTAAAGTTCCTG

GTGTTGGTCTGCCTGGTGTTTATCCAGGCGGTGTTCTGCCAGGTGCGCGT

TTTCCTGGCGTGGGTGTTCTGCCGGGTGTTCCGACCGGTGCAGGCGTGAA

ACCGAAAGCACCAGGTGTTGGTGGTGCATTTGCAGGTATTCCAGGTGTGG

GTCCGTTTGGTGGTCCGCAGCCAGGCGTTCCGCTGGGTTATCCGATTAAA

GCACCGAAACTGCCTGGCGGTTATGGTCTGCCGTATACCACCGGTAAACT

GCCGTATGGTTATGGCCCTGGCGGTGTTGCCGGTGCGGCAGGTAAAGCAG

GCTATCCGACCGGTACCGGTGTAGGTCCGCAGGCAGCAGCCGCAGCAGCG

GCAAAAGCAGCAGCGAAATTTGGTGCGGGTGCAGCCGGTGTGCTGCCAGG

CGTAGGTGGCGCTGGTGTACCTGGTGTCCCTGGCGCAATTCCAGGTATTG

GCGGTATTGCAGGCGTTGGTACTCCGGCAGCTGCAGCCGCTGCCGCAGCC

GCAGCTAAAGCAGCCAAATATGGTGCAGCGGCAGGCCTGGTTCCTGGCGG

TCCAGGTTTTGGTCCGGGTGTTGTTGGCGTCCCAGGTGCCGGTGTGCCTG

-continued

```
GTGTGGGTGTTCCAGGTGCGGGTATTCCGGTTGTTCCTGGCGCAGGCATT

CCGGGTGCCGCAGTTCCGGGTGTAGTTAGCCCGGAATAA
```

The amino acid sequence of the non-naturally occurring truncated human elastin without the DsbA secretion tag is disclosed in SEQ ID NO: 15.

```
                                      (SEQ ID NO: 15)
AGLGGVPGVGGLGVSAGAVVPQPGAGVKPGKVPGVGLPGVYPGGVLPGAR

FPGVGVLPGVPTGAGVKPKAPGVGGAFAGIPGVGPFGGPQPGVPLGYPIK

APKLPGGYGLPYTTGKLPYGYGPGGVAGAAGKAGYPTGTGVGPQAAAAAA

AKAAAKFGAGAAGVLPGVGGAGVPGVPGAIPGIGGIAGVGTPAAAAAAAA

AAKAAKYGAAAGLVPGGPGFGPGVVGVPGAGVPGVGVPGAGIPVVPGAGI

PGAAVPGVVSPE
```

The polynucleotide of SEQ ID NO: 12 was synthesized by Twist DNA. Overlaps between the pET28 vector and SEQ ID NO: 12 were designed to be between 20 and 30 bp long and added using PCR with the enzyme PRIMESTAR® GXL polymerase (takarabio.com/products/pcr/gc-rich-pcr/primestar-gxl-dna-polymerase). The opened pET28a vector and insert DNA (SEQ ID NO: 12) were then assembled together into the final plasmid using IN-FUSION® Cloning (takarabio.com/products/cloning/in-fusion-cloning). The sequence of the plasmid was then verified using Sanger sequencing through Genewiz (genewiz.com/en).

The transformed cells were cultivated in minimal media of Example 1 and frozen in 1.5 mL aliquots with vegetable glycerin at a ratio of 50:50 of cells to glycerin. One vial of this frozen culture was revived in 50 mL of minimal media overnight at 37° C., 200 rpm. Cells were transferred into 300 mL of minimal media and grown for 6-9 hours to reach an OD600 of 5-10.

The 23 kDa non-naturally occurring truncated human elastin was detected on 12% BisTris protein gel. A photograph of the gel is depicted in FIG. 1. The 23 kDa non-naturally occurring truncated human elastin was confirmed to be the correct mass by intact mass spectrometry using liquid chromatography-mass spectrometry.

Example 11. 13 kDa Truncated Human Elastin

A non-naturally occurring truncated human without a His tag, linker, and thrombin cleavage site is disclosed below. The codon-optimized nucleotide sequence encoding this elastin and the amino acid sequence are disclosed below. In SEQ ID NO: 16, the DsbA secretion tag is encoded by nucleotides 1-57 and encodes amino acids 1-19 of SEQ ID NO: 17. In SEQ ID NO: 16, the truncated elastin sequence is encoded by nucleotides 58-489 and encodes amino acids 20-163 of SEQ ID NO: 17.

The codon-optimized nucleotide sequence encoding this elastin is provided in SEQ ID NO: 16.

```
                                      (SEQ ID NO: 16)
ATGAAAAAGATTTGGCTGGCGCTGGCTGGTTTAGTTTTAGCGTTTAGCGC

ATCGGCGGCCGGTCTGGGTGGCGTGCCTGGCGTTGGTGGCCTGGGCGTTA

GCGCCGGTGCAGTTGTTCCGCAGCCTGGTGCGGGTGTTAAACCGGGTAAA

GTTCCTGGTGTTGGTCTGCCTGGTGTTTATCCAGGCGGTGTTCTGCCAGG

TGCGCGTTTTCCTGGCGTGGGTGTTCTGCCGGGTGTTCCGACCGGTGCAG

GCGTGAAACCGAAAGCACCAGGTGTTGGTGGTGCATTTGCAGGTATTCCA

GGTGTGGGTCCGTTTGGTGGTCCGCAGCCAGGCGTTCCGCTGGGTTATCC

GATTAAAGCACCGAAACTGCCTGGCGGTTATGGTCTGCCGTATACCACCG

GTAAACTGCCGTATGGTTATGGCCCTGGCGGTGTTGCCGGTGCGGCAGGT

AAAGCAGGCTATCCGACCGGTACCGGTGTAGGTCCGCAGTAA
```

The amino acid sequence of the 13 kDa non-naturally occurring truncated human elastin sequence including the DsbA secretion signal is disclosed in SEQ ID NO: 17.

```
                                      (SEQ ID NO: 17)
MKKIWLALAGLVLAFSASAAGLGGVPGVGGLGVSAGAVVPQPGAGVKPGK

VPGVGLPGVYPGGVLPGARFPGVGVLPGVPTGAGVKPKAPGVGGAFAGIP

GVGPFGGPQPGVPLGYPIKAPKLPGGYGLPYTTGKLPYGYGPGGVAGAAG

KAGYPTGTGVGPQ
```

The codon-optimized nucleotide sequence encoding the non-naturally occurring truncated human elastin without the DsbA secretion tag is provided in SEQ ID NO: 18.

```
                                      (SEQ ID NO: 18)
GCCGGTCTGGGTGGCGTGCCTGGCGTTGGTGGCCTGGGCGTTAGCGCCGG

TGCAGTTGTTCCGCAGCCTGGTGCGGGTGTTAAACCGGGTAAAGTTCCTG

GTGTTGGTCTGCCTGGTGTTTATCCAGGCGGTGTTCTGCCAGGTGCGCGT

TTTCCTGGCGTGGGTGTTCTGCCGGGTGTTCCGACCGGTGCAGGCGTGAA

ACCGAAAGCACCAGGTGTTGGTGGTGCATTTGCAGGTATTCCAGGTGTGG

GTCCGTTTGGTGGTCCGCAGCCAGGCGTTCCGCTGGGTTATCCGATTAAA

GCACCGAAACTGCCTGGCGGTTATGGTCTGCCGTATACCACCGGTAAACT

GCCGTATGGTTATGGCCCTGGCGGTGTTGCCGGTGCGGCAGGTAAAGCAG

GCTATCCGACCGGTACCGGTGTAGGTCCGCAGTAA
```

The amino acid sequence of the non-naturally occurring truncated human elastin without the DsbA secretion tag is disclosed in SEQ ID NO: 19.

```
                                      (SEQ ID NO: 19)
AGLGGVPGVGGLGVSAGAVVPQPGAGVKPGKVPGVGLPGVYPGGVLPGAR

FPGVGVLPGVPTGAGVKPKAPGVGGAFAGIPGVGPFGGPQPGVPLGYPIK

APKLPGGYGLPYTTGKLPYGYGPGGVAGAAGKAGYPTGTGVGPQ
```

The polynucleotide of SEQ ID NO: 16 was synthesized by Twist DNA. Overlaps between the pET28 vector and SEQ ID NO: 16 were designed to be between 20 and 30 bp long and added using PCR with the enzyme PRIMESTAR® GXL polymerase (takarabio.com/products/pcr/gc-rich-pcr/primestar-gxl-dna-polymerase). The opened pET28a vector and insert DNA (SEQ ID NO: 16) were then assembled together into the final plasmid using IN-FUSION® Cloning (takarabio.com/products/cloning/in-fusion-cloning). The sequence of the plasmid was then verified through Sanger sequencing through Genewiz (genewiz.com/en).

The transformed cells were cultivated in minimal media and frozen in 1.5 mL aliquots with vegetable glycerin at a ratio of 50:50 of cells to glycerin. One vial of this frozen culture was revived in 50 mL of minimal media overnight at 37° C., 200 rpm. Cells were transferred into 300 mL of minimal media and grown for 6-9 hours to reach an OD600 of 5-10.

The 13 kDa non-naturally occurring truncated human elastin was detected on 12% BisTris protein gel. A photograph of the gel is depicted in FIG. 1. The 13 kDa non-naturally occurring truncated human elastin was confirmed to be the correct mass by intact mass spectrometry using liquid chromatography-mass spectrometry

Figure 2:
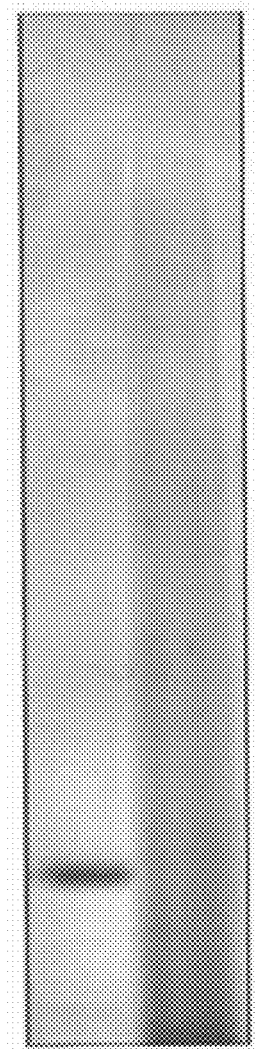
FIG. 2 depicts an SDS-PAGE protein gel showing high purity and homogeneity of a recombinantly produced polypeptide (comprising a non-naturally occurring truncated elastin amino acid sequence) described herein. Lane A depicts the recombinantly produced polypeptide, and Lane B depicts a commercially-available elastin.

Example 12. Purity and Uniformity of a 13 kDa Non-Naturally Occurring Truncated Elastin A polypeptide with an amino acid sequence according to SEQ ID NO: 19 was analyzed by SDS-PAGE to assess purity and uniformity. FIG. 2 demonstrates that the polypeptide with an amino acid sequence according to SEQ ID NO: 19 appeared as a single band on an SDS-PAGE protein gel, indicating high purity and homogeneity. In contrast, a commercially-available elastin appeared as a smear on the protein gel indicating high heterogeneity.

Figure 3:
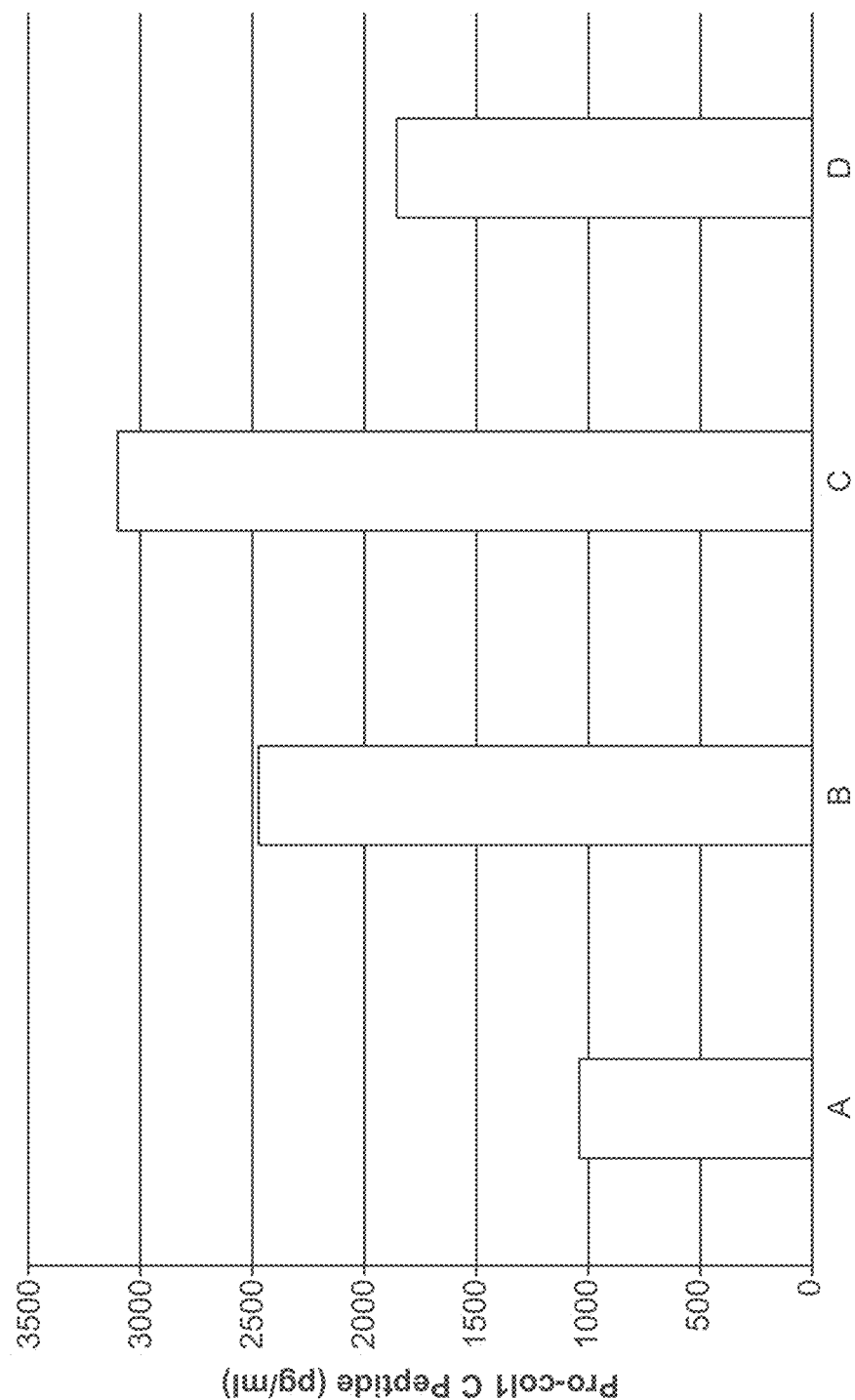
FIG. 3 depicts secretion levels of pro-collagen type I C-peptide after treatment of fibroblasts with an exemplary polypeptide (comprising a non-naturally occurring truncated elastin amino acid sequence) provided herein.

Example 13. In Vitro Study of a Non-Naturally Occurring Truncated Human Elastin Non-Naturally Occurring Truncated Human Elastin Stimulates Fibroblast Production of Collagen Type I Protein Fibroblasts are the main source of the extracellular matrix peptides, including the structural proteins collagen and elastin. Human primary fibroblasts were evaluated for collagen type I protein secretion. Fibroblasts were cultured with a polypeptide according to SEQ ID NO: 19 for 48 hours. The culture supernatants were analyzed by ELISA for pro-collagen type I C-peptide, a readout for total secreted collagen type I protein. FIG. 3 demonstrates that fibroblasts treated with a 0.1% w/w solution (FIG. 3, "B"), a 0.05% w/w solution (FIG. 3, "C"), and a 0.025% w/w solution (FIG. 3, "D") of a polypeptide according to SEQ ID NO: 19 secreted higher levels of collagen type I than untreated control fibroblasts (FIG. 3, "A").

Figure 4:
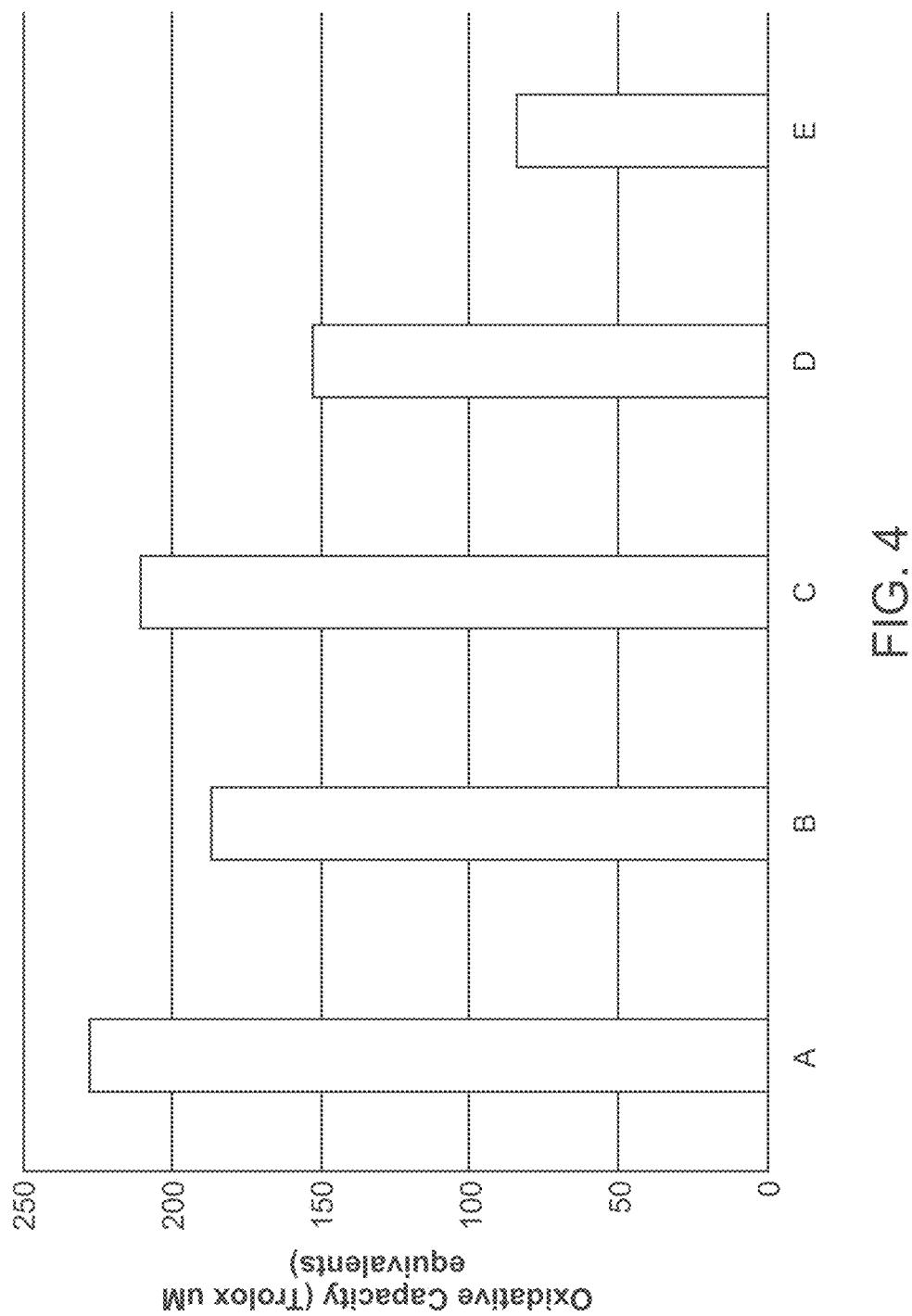
FIG. 4 depicts the anti-oxidative capacity of an exemplary polypeptide (comprising a non-naturally occurring truncated elastin amino acid sequence) provided herein.

Non-Naturally Occurring Truncated Human Elastin Demonstrates Anti-Oxidative Capacity An oxygen radical absorbance capacity (ORAC) assay was performed to analyze the anti-oxidative capacity of a polypeptide according to SEQ ID NO: 19. The ORAC assay is a cell-free assay that uses a fluorescent readout to measure anti-oxidative capacity. Data is reported in Trolox (Vitamin E) equivalents (TEs). As shown in FIG. 4, a 0.0125% w/w solution (FIG. 4, "E"), a 0.025% w/w solution (FIG. 4, "D"), a 0.05% w/w solution (FIG. 4, "C"), a 0.1% w/w solution (FIG. 4, "B"), and a 0.2% w/w solution (FIG. 4, "A") of a polypeptide according to SEQ ID NO: 19 each demonstrated anti-oxidative properties. For example, a 0.2% w/w solution of a polypeptide according to SEQ ID NO: 19 demonstrated anti-oxidative properties equivalent to 228 μM Trolox.

Figure 5:
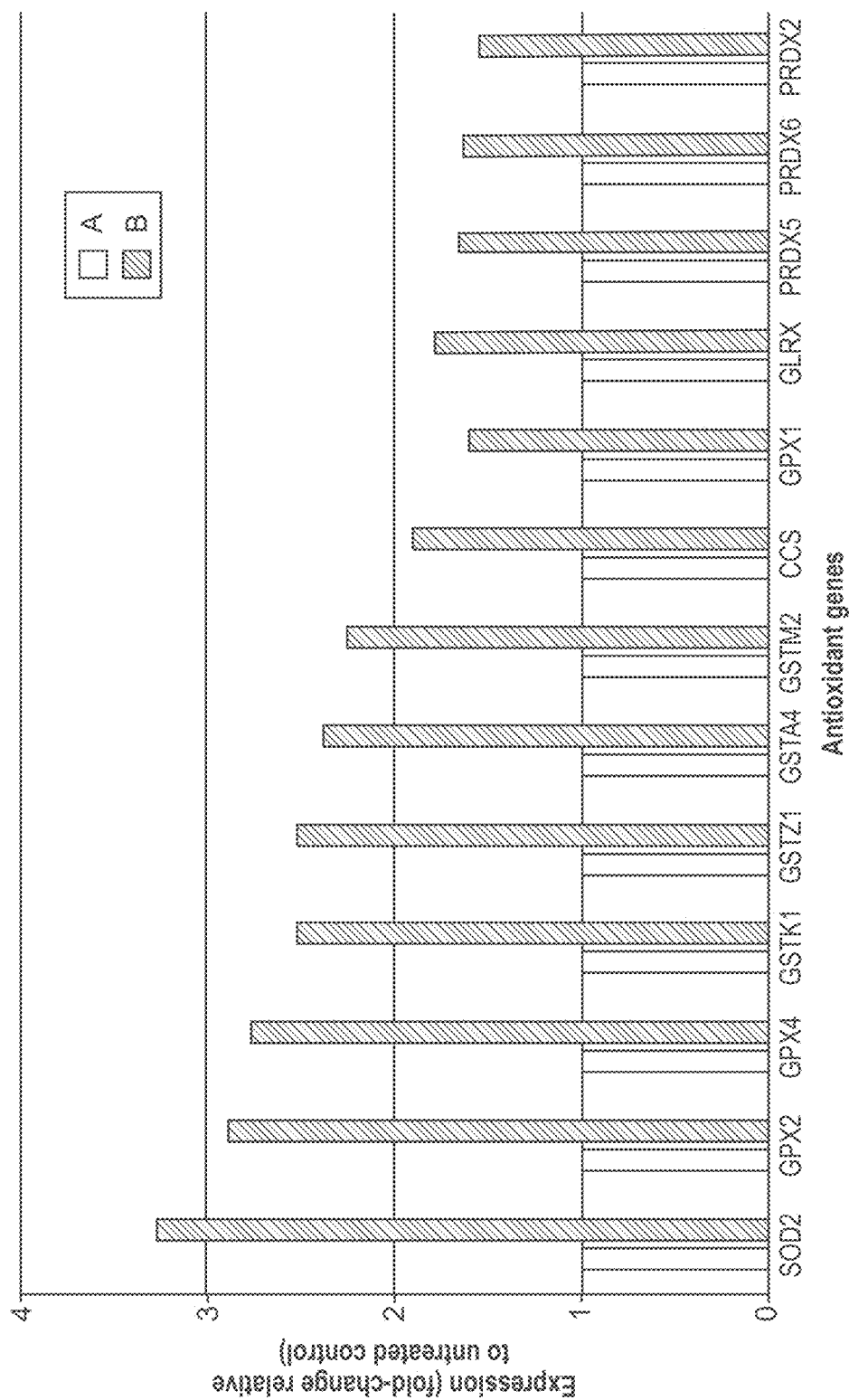
FIG. 5 depicts expression levels of mRNA of various anti-oxidant genes after treatment of keratinocytes with an exemplary polypeptide (comprising a non-naturally occurring truncated elastin amino acid sequence) provided herein.

Non-Naturally Occurring Truncated Human Elastin Stimulates Antioxidant Genes in Keratinocytes Keratinocytes were incubated for 24 hours with media alone or with 0.03% w/w solution of a polypeptide according to SEQ ID NO: 19. RNA was extracted from the cells and analyzed by Clariom microarray (ThermoFisher) for global gene expression. FIG. 5 demonstrates that many antioxidant genes, including SOD2, GPX2, GPX4, GSTK1, GSTZ1, GSTA4, GSTM2, CCS, GPX1, GLRX, PRDX5, PRDX6, and PRDX2, were upregulated in keratinocytes treated with a polypeptide according to SEQ ID NO: 19 (FIG. 5, "B"), relative to untreated cells (FIG. 5, "A").

Figure 6:
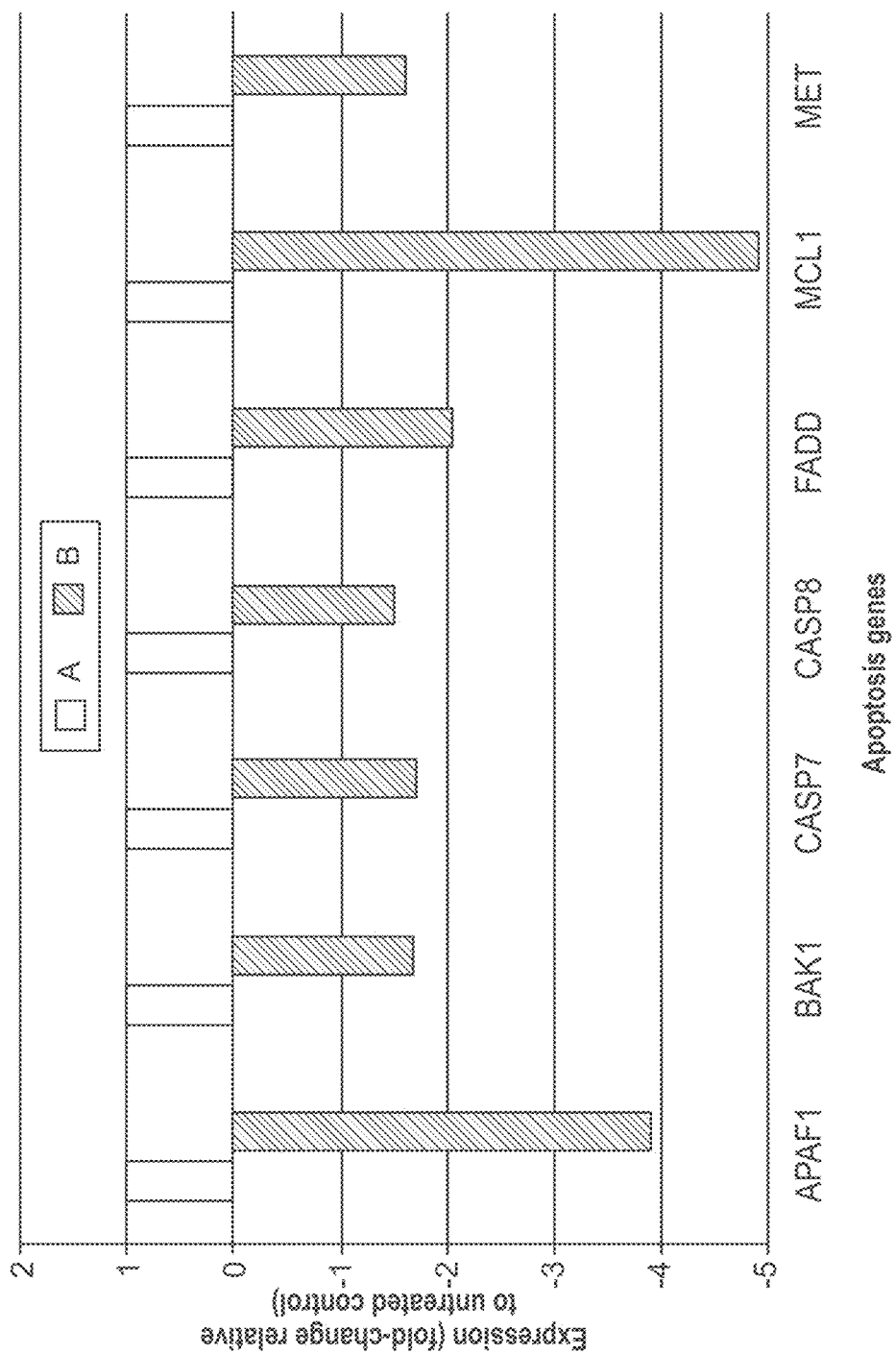
FIG. 6 depicts expression levels of mRNA of various pro-apoptotic genes after treatment of keratinocytes with an exemplary polypeptide (comprising a non-naturally occurring truncated elastin amino acid sequence) provided herein.

Non-Naturally Occurring Truncated Human Elastin Reduces Expression of Apoptosis Genes in Keratinocytes Keratinocytes were incubated for 24 hours with media alone (untreated) or with 0.03% w/w solution of a polypeptide according to SEQ ID NO: 19. RNA was extracted from the cells and analyzed by Clariom microarray (ThermoFisher) for global gene expression. FIG. 6 demonstrates that many pro-apoptotic genes, including APAF1, BAK1, CASP7, CASP8, FADD, MCL1, and MET, were downregulated in keratinocytes treated with a polypeptide according to SEQ ID NO: 19 (FIG. 6, "B"), relative to untreated cells (FIG. 6, "A").

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A non-naturally occurring polypeptide produced in a microbial host cell, wherein the non-naturally occurring polypeptide comprises the amino acid sequence having at least 80% sequence identity to a truncate of SEQ ID NO: 20, wherein the truncate of SEQ ID NO: 20 has an N-terminal truncation and a C-terminal truncation relative to SEQ ID NO: 20, wherein the amino acid sequence having at least 80% sequence identity to the truncate of SEQ ID NO: 20 comprises the amino acid sequence having at least 80% sequence identity to SEQ ID NO: 19, and wherein the non-naturally occurring polypeptide is monomeric and lacks a cross-linked structure of natural elastin.

2. The non-naturally occurring polypeptide of claim 1, wherein the non-naturally occurring polypeptide comprises the amino acid sequence having at least 85% sequence identity to the truncate of SEQ ID NO: 20.

3. The non-naturally occurring polypeptide of claim 1, wherein the non-naturally occurring polypeptide comprises the amino acid sequence having at least 90% sequence identity to the truncate of SEQ ID NO: 20.

4. The non-naturally occurring polypeptide of claim 1, wherein the non-naturally occurring polypeptide comprises the amino acid sequence having at least 95% sequence identity to the truncate of SEQ ID NO: 20.

5. The non-naturally occurring polypeptide of claim 1, wherein the non-naturally occurring polypeptide comprises the amino acid sequence having at least 99% sequence identity to the truncate of SEQ ID NO: 20.

6. The non-naturally occurring polypeptide of claim 1, wherein the non-naturally occurring polypeptide comprises the amino acid sequence having 100% sequence identity to the truncate of SEQ ID NO: 20.

7. The non-naturally occurring polypeptide of claim 1, wherein the amino acid sequence having at least 80% sequence identity to the truncate of SEQ ID NO: 20 comprises the amino acid sequence having at least 85% sequence identity to SEQ ID NO: 19.

8. The non-naturally occurring polypeptide of claim 1, wherein the amino acid sequence having at least 80% sequence identity to the truncate of SEQ ID NO: 20 comprises the amino acid sequence having at least 90% sequence identity to SEQ ID NO: 19.

9. The non-naturally occurring polypeptide of claim 1, wherein the amino acid sequence having at least 80% sequence identity to the truncate of SEQ ID NO: 20 comprises the amino acid sequence having at least 95% sequence identity to SEQ ID NO: 19.

10. The non-naturally occurring polypeptide of claim 1, wherein the amino acid sequence having at least 80% sequence identity to the truncate of SEQ ID NO: 20 comprises the amino acid sequence having at least 99% sequence identity to SEQ ID NO: 19.

11. The non-naturally occurring polypeptide of claim 1, wherein the amino acid sequence having at least 80% sequence identity to the truncate of SEQ ID NO: 20 comprises the amino acid sequence having 100% sequence identity to SEQ ID NO: 19.

12. The non-naturally occurring polypeptide of claim 1, wherein the microbial host cell is a bacterial cell, a yeast cell, or a fungal cell.

13. The non-naturally occurring polypeptide of claim 12, wherein the microbial host cell is *Escherichia coli*.

14. A composition comprising from 0.001% w/w to 30% w/w of the non-naturally occurring polypeptide of claim 1.

15. The composition of claim 14, wherein the composition comprises from 0.001% w/w to 5% w/w of the non-naturally occurring polypeptide.

16. The composition of claim 14, wherein the composition is formulated for topical application.

17. The composition of claim 16, wherein the composition comprises a topical carrier, a preservative, or both.

18. The composition of claim 17, wherein the topical carrier is selected from the group consisting of: water, oil glycereth-8 esters, glycerin, coconut alkanes, hydroxyethyl acrylate/sodium acryloyldimethyl taurate copolymer, pentylene glycol, disodium ethylenediaminetetraacetic acid (EDTA), caprylyl glycol, chlorphenesin, phenoxyethanol, liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, and cyclopentasiloxane.

19. The composition of claim 17, wherein the preservative is selected from the group consisting of: tocopherol, diiodomethyl-p-tolylsulfone, 2-bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-ethylbicyclooxazolidine, methyl paraben, sorbic acid, rosemary extract, and EDTA.

20. The composition of claim 14, wherein the composition is a cosmetic.

21. The composition of claim 20, wherein the cosmetic is selected from the group consisting of: a mask, a skin cleaner, a soap, a cleansing cream, a cleansing lotion, a facial cleanser, a cleansing milk, a cleansing pad, a facial wash, a facial cream, a body cream, a facial moisturizer, a body moisturizer, a facial serum, a facial mask, a body mask, a facial toner, a facial mist, an eye cream, an eye treatment, an exfoliator formula, a lip balm, a lipstick, an eye shadow, a concealer, a mascara, a color cosmetic, and any combination thereof.

22. The composition of claim 14, wherein the composition is formulated as a personal care product for application to hair.

23. The composition of claim 22, wherein the personal care product is selected from the group consisting of: a hair shampoo, a hair conditioner, a hair serum, a scalp serum, a hair mist, and a hair spray.

24. A method for improving the appearance of skin, the method comprising applying the composition of claim 16 to the skin of a subject, thereby improving the appearance of the skin.

25. The method of claim 24, wherein the improving the appearance of skin is selected from the group consisting of: increasing firmness of the skin, increasing elasticity of the skin, increasing brightness of the skin, increasing hydration of the skin, increasing tactile texture of the skin, increasing visual texture of the skin, and any combination thereof.

26. A method for improving skin health, the method comprising applying the composition of claim 16 to the skin of a subject, wherein the applying results in decreasing skin damage, promoting repair of damaged skin, protecting the skin against ultraviolet (UV) damage, increasing viability of skin cells, protecting skin cells from the effects of urban dust exposure, or any combination thereof, thereby improving skin health.

27. The method of claim 26, wherein the improving skin health is selected from the group consisting of: increased viability of skin fibroblast cells, increased viability of skin keratinocyte cells, increased synthesis of procollagen by skin fibroblast cells, increased expression of at least one antioxidant gene by skin keratinocytes, decreased expression of one or more pro-apoptotic genes by skin keratinocytes, decreased expression of inflammatory cytokines by skin keratinocytes, and any combination thereof.

28. A method for treating damage to hair, the method comprising applying the composition of claim 22 to the hair of a subject, thereby treating the damage to hair.

29. The method of claim 28, wherein the damage to hair is caused by ultraviolet radiation.

* * * * *

SEQUENCE LISTING

```
<160> NUMBER OF SEQ ID NOS: 34

<210> SEQ ID NO 1
<211> LENGTH: 6
<212> TYPE: PRT
<213> ORGANISM: Homo sapiens

<400> SEQUENCE: 1

Val Gly Val Ala Pro Gly
1               5

<210> SEQ ID NO 2
<211> LENGTH: 12
<212> TYPE: PRT
<213> ORGANISM: Homo sapiens

<400> SEQUENCE: 2

Val Gly Val Ala Pro Gly Val Gly Val Ala Pro Gly
```

<210> SEQ ID NO 3
<211> LENGTH: 18
<212> TYPE: PRT
<213> ORGANISM: Homo sapiens

<400> SEQUENCE: 3

Val Gly Val Ala Pro Gly Val Gly Val Ala Pro Gly Val Gly Val Ala
1               5                   10                  15

Pro Gly

<210> SEQ ID NO 4
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgaaaaaga tttggctggc gctggctggt ttagttttag cgtttagcgc atcggcgggt      60
ccgcaacctg gggttccgtt aggttatccg attaaagcac cgaaactgcc cggcggttat     120
ggtctgccgt acacaaccgg taaactgccg tatggttatg gcccgggtgg agttgcgggt     180
gcagcaggta aagcgggtta tcctaccgga accggtgtag tccgcaggc cgctgctgcc     240 gccgccgcaa agcagcggc taaatttggc gccggagcag cgggtgttct gcctggagtt     300
ggtggtgcgg gcgtgccagg ggtacctggt gcaattccgg gtattggtgg tattgccggt     360
gtcggcaccc cggccgcggc agctgcggca gcggcggctg ccaaagctgc taaatacggt     420
gccgcggcgg gtctggtgcc aggaggtccg ggttttggtc cgggagtggt tggcgtgcct     480
ggcgcaggcg ttcctggtgt gggcgttcca ggtgcaggga ttcctgttgt gcctggtgcc     540
ggtattcccg cgcggccgt tccggggtg gttagcccgg aagccgcagc gaaggctgcg     600
gcaaaggcag caaagtatgg cgcacgccca ggagtcggcg tgggtggtat cccgacctat     660
ggggtgggcg caggggtttt cctggtttc ggcgtaggtg taggaggtat accgggcgtg     720
gccggtgtac caggggttgg tggcgtccct ggtgttggcg gtgtgccagg tgttggtatt     780
tcaccggaag cacaggcagc agccgcagct aaggcagcga aatatggtgc cgccggcgca     840
ggagttttag gtgggctggt tccgggcccg caggcagctg tgccgggggt tccaggcacc     900
ggtggtgtcc ctggagtcgg tacgccgtaa                                     930

<210> SEQ ID NO 5
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Lys Ile Trp Leu Ala Leu Ala Gly Leu Val Leu Ala Phe Ser
1               5                   10                  15

Ala Ser Ala Gly Pro Gln Pro Gly Val Pro Leu Gly Tyr Pro Ile Lys
                20                  25                  30

Ala Pro Lys Leu Pro Gly Gly Tyr Gly Leu Pro Tyr Thr Thr Gly Lys
            35                  40                  45

Leu Pro Tyr Gly Tyr Gly Pro Gly Gly Val Ala Gly Ala Ala Gly Lys

```
                50                  55                  60
Ala Gly Tyr Pro Thr Gly Thr Gly Val Gly Pro Gln Ala Ala Ala
 65                  70                  75                  80

Ala Ala Ala Lys Ala Ala Ala Lys Phe Gly Ala Gly Ala Ala Gly Val
                 85                  90                  95

Leu Pro Gly Val Gly Gly Ala Gly Val Pro Gly Val Pro Gly Ala Ile
                100                 105                 110

Pro Gly Ile Gly Gly Ile Ala Gly Val Gly Thr Pro Ala Ala Ala
            115                 120                 125

Ala Ala Ala Ala Ala Ala Lys Ala Ala Lys Tyr Gly Ala Ala Ala Gly
            130                 135                 140

Leu Val Pro Gly Gly Pro Gly Phe Gly Pro Gly Val Val Gly Val Pro
145                 150                 155                 160

Gly Ala Gly Val Pro Gly Val Gly Val Pro Gly Ala Gly Ile Pro Val
                165                 170                 175

Val Pro Gly Ala Gly Ile Pro Gly Ala Ala Val Pro Gly Val Val Ser
            180                 185                 190

Pro Glu Ala Ala Ala Lys Ala Ala Ala Lys Ala Ala Lys Tyr Gly Ala
            195                 200                 205

Arg Pro Gly Val Gly Val Gly Gly Ile Pro Thr Tyr Gly Val Gly Ala
210                 215                 220

Gly Gly Phe Pro Gly Phe Gly Val Gly Val Gly Gly Ile Pro Gly Val
225                 230                 235                 240

Ala Gly Val Pro Gly Val Gly Gly Val Pro Gly Val Gly Gly Val Pro
                245                 250                 255

Gly Val Gly Ile Ser Pro Glu Ala Gln Ala Ala Ala Ala Lys Ala
            260                 265                 270

Ala Lys Tyr Gly Ala Ala Gly Ala Gly Val Leu Gly Gly Leu Val Pro
            275                 280                 285

Gly Pro Gln Ala Ala Val Pro Gly Val Pro Gly Thr Gly Gly Val Pro
            290                 295                 300

Gly Val Gly Thr Pro
305

<210> SEQ ID NO 6
<211> LENGTH: 873
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ggtccgcaac ctggggttcc gttaggttat ccgattaaag caccgaaact gcccggcggt      60
tatggtctgc cgtacacaac cggtaaactg ccgtatggtt atggcccggg tggagttgcg     120
ggtgcagcag gtaaagcggg ttatcctacc ggaaccggtg taggtccgca ggccgctgct     180
gccgccgccg caaaagcagc ggctaaattt ggcgccggag cagcgggtgt tctgcctgga     240
gttggtggtg cgggcgtgcc agggggtacct ggtgcaattc cgggtattgg tggtattgcc     300
ggtgtcggca ccccggccgc ggcagctgcg gcagcggcgg ctgccaaagc tgctaaatac     360
ggtgccgcgg cgggtctggt gccaggaggt ccgggttttg gtccgggagt ggttggcgtg     420
cctggcgcag gcgttcctgg tgtgggcgtt ccaggtgcag ggattcctgt tgtgcctggt     480
gccggtattc ccggcgcggc cgttccgggg gtggttagcc cggaagccgc agcgaaggct     540
```

```
gcggcaaagg cagcaaagta tgcgcacgc ccaggagtcg gcgtgggtgg tatcccgacc    600
tatggggtgg gcgcagggg ttttcctggt tcggcgtag gtgtaggagg tataccgggc     660
gtggccggtg taccaggggt tggtggcgtc cctggtgttg gcggtgtgcc aggtgttggt    720
atttcaccgg aagcacaggc agcagccgca gctaaggcag cgaaatatgg tgccgccggc    780
gcaggagttt aggtgggct ggttccgggc ccgcaggcag ctgtgccggg ggttccaggc     840
accggtggtg tccctggagt cggtacgccg taa                                 873
```

<210> SEQ ID NO 7
<211> LENGTH: 290
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Gly Pro Gln Pro Gly Val Pro Leu Gly Tyr Pro Ile Lys Ala Pro Lys
1               5                   10                  15

Leu Pro Gly Gly Tyr Gly Leu Pro Tyr Thr Thr Gly Lys Leu Pro Tyr
            20                  25                  30

Gly Tyr Gly Pro Gly Gly Val Ala Gly Ala Ala Gly Lys Ala Gly Tyr
        35                  40                  45

Pro Thr Gly Thr Gly Val Gly Pro Gln Ala Ala Ala Ala Ala Ala Ala
    50                  55                  60

Lys Ala Ala Ala Lys Phe Gly Ala Gly Ala Ala Gly Val Leu Pro Gly
65                  70                  75                  80

Val Gly Gly Ala Gly Val Pro Gly Val Pro Gly Ala Ile Pro Gly Ile
                85                  90                  95

Gly Gly Ile Ala Gly Val Gly Thr Pro Ala Ala Ala Ala Ala Ala Ala
            100                 105                 110

Ala Ala Ala Lys Ala Ala Lys Tyr Gly Ala Ala Ala Gly Leu Val Pro
        115                 120                 125

Gly Gly Pro Gly Phe Gly Pro Gly Val Val Gly Val Pro Gly Ala Gly
    130                 135                 140

Val Pro Gly Val Gly Val Pro Gly Ala Gly Ile Pro Val Val Pro Gly
145                 150                 155                 160

Ala Gly Ile Pro Gly Ala Ala Val Pro Gly Val Val Ser Pro Glu Ala
                165                 170                 175

Ala Ala Lys Ala Ala Lys Ala Ala Lys Tyr Gly Ala Arg Pro Gly
            180                 185                 190

Val Gly Val Gly Gly Ile Pro Thr Tyr Gly Val Gly Ala Gly Gly Phe
        195                 200                 205

Pro Gly Phe Gly Val Gly Val Gly Gly Ile Pro Gly Val Ala Gly Val
    210                 215                 220

Pro Gly Val Gly Gly Val Pro Gly Val Gly Gly Val Pro Gly Val Gly
225                 230                 235                 240

Ile Ser Pro Glu Ala Gln Ala Ala Ala Ala Lys Ala Ala Lys Tyr
                245                 250                 255

Gly Ala Ala Gly Ala Gly Val Leu Gly Gly Leu Val Pro Gly Pro Gln
            260                 265                 270

Ala Ala Val Pro Gly Val Pro Gly Thr Gly Gly Val Pro Gly Val Gly
        275                 280                 285

Thr Pro
    290
```

<210> SEQ ID NO 8
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Gly Pro Gly Gly Val Ala Ala Ala Lys Ser Ala Ala Lys Val Ala
1               5                   10                  15

Ala Lys Ala Gln Leu Arg Ala Ala Gly Leu Gly Ala Gly Ile Pro
                20                  25                  30

Gly Leu Gly Val Gly Val Gly Val Pro Gly Leu Gly Val Gly Ala Gly
            35                  40                  45

Val Pro Gly Leu Gly Val Gly Ala Gly Val Pro Gly Phe Gly Ala Gly
        50                  55                  60

Ala Asp Glu Gly Val Arg Arg Ser Leu Ser Pro Glu Leu Arg Glu Gly
65                  70                  75                  80

Asp Pro Ser Ser Ser Gln His Leu Pro Ser Thr Pro Ser Ser Pro Arg
                85                  90                  95

Val Pro Gly Ala Leu Ala Ala Ala Lys Ala Ala Lys Tyr Gly Ala Ala
                100                 105                 110

Val Pro Gly Val Leu Gly Gly Leu Gly Ala Leu Gly Gly Val Gly Ile
            115                 120                 125

Pro Gly Gly Val Val Gly Ala Gly Pro Ala Ala Ala Ala Ala Ala
        130                 135                 140

Lys Ala Ala Ala Lys Ala Ala Gln Phe Gly Leu Val Gly Ala Ala Gly
145                 150                 155                 160

Leu Gly Gly Leu Gly Val Gly Leu Gly Val Pro Gly Val Gly Gly
                165                 170                 175

Leu Gly Gly Ile Pro Pro Ala Ala Ala Ala Lys Ala Ala Lys Tyr Gly
            180                 185                 190

Ala Ala Gly Leu Gly Gly Val Leu Gly Gly Ala Gly Gln Phe Pro Leu
        195                 200                 205

Gly Gly Val Ala Ala Arg Pro Gly Phe Gly Leu Ser Pro Ile Phe Pro
    210                 215                 220

Gly Gly Ala Cys Leu Gly Lys Ala Cys Gly Arg Lys Arg Lys
225                 230                 235

<210> SEQ ID NO 9
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
ggtccgggcg gtgtcgcagc agcagctaaa agcgcggcga agttgcggc caaagcccaa      60 ctgcgcgccg ccgcgggcct cggtgcaggt attccgggc tgggtgtcgg agttggagtc    120
ccgggtttgg gcgtgggcgc gggagttccg ggactgggag tgggtgccgg agttcctggc   180
tttggtgcag gcgcagatga aggtgttcgt cgtagcctga gtccggaact gcgtgaaggt   240
gatccgagta gcagccagca tctgccgagc accccgagca gcccgcgtgt tccgggtgca   300
ttagctgcag caaaagccgc caagtatggt gcagccgtgc cgggcgtctt aggtggtctg   360

-continued

```
ggcgccctgg gtggtgtagg cattccggga ggtgttgtgg gtgcaggacc ggccgccgca      420
gctgcggccg ccaaagcagc tgcaaaagcg cccagtttg gtttagtggg cgccgcaggt       480
ttaggcggtt taggtgtggg tggactgggt gtacctggcg taggcggtct gggtggaatt      540
ccgcccgcag cggccgcgaa agcggcaaaa tatggcgcgg caggcctggg cggcgtgctg      600
ggtggggcag gtcagtttcc gctgggcggg gttgccgcac gtccgggatt tggtctgagc      660 ccgatttttcc ctggcggcgc atgtctgggt aaagcatgtg tcgtaaacg taaataa       717
```

<210> SEQ ID NO 10
<211> LENGTH: 693
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Ala Gly Val
                245                 250                 255

Pro Gly Val Pro Gly Ala Ile Pro Gly Ile Gly Ile Ala Gly Val
            260                 265                 270

Gly Thr Pro Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
```

```
                290                 295                 300
Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Lys Ala Ala Ala
                340                 345                 350

Lys Ala Ala Lys Tyr Gly Ala Arg Pro Gly Val Gly Val Gly Gly Ile
                355                 360                 365

Pro Thr Tyr Gly Val Gly Ala Gly Gly Phe Pro Gly Phe Gly Val Gly
370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
                420                 425                 430

Val Leu Gly Gly Leu Val Pro Gly Pro Gln Ala Ala Val Pro Gly Val
                435                 440                 445

Pro Gly Thr Gly Gly Val Pro Gly Val Gly Thr Pro Ala Ala Ala Ala
                450                 455                 460

Lys Ser Ala Ala Lys Val Ala Ala Lys Ala Gln Leu Arg Ala Ala Ala
465                 470                 475                 480

Gly Leu Gly Ala Gly Ile Pro Gly Leu Gly Val Gly Val Gly Val Pro
                485                 490                 495

Gly Leu Gly Val Gly Ala Gly Val Pro Gly Leu Gly Val Gly Ala Gly
                500                 505                 510

Val Pro Gly Phe Gly Ala Gly Ala Asp Glu Gly Val Arg Arg Ser Leu
                515                 520                 525

Ser Pro Glu Leu Arg Glu Gly Asp Pro Ser Ser Gln His Leu Pro
                530                 535                 540

Ser Thr Pro Ser Ser Pro Arg Val Pro Gly Ala Leu Ala Ala Ala Lys
545                 550                 555                 560

Ala Ala Lys Tyr Gly Ala Ala Val Pro Gly Val Leu Gly Gly Leu Gly
                565                 570                 575

Ala Leu Gly Gly Val Gly Ile Pro Gly Gly Val Val Gly Ala Gly Pro
                580                 585                 590

Ala Ala Ala Ala Ala Ala Lys Ala Ala Ala Lys Ala Ala Gln Phe
                595                 600                 605

Gly Leu Val Gly Ala Ala Gly Leu Gly Gly Leu Gly Val Gly Gly Leu
                610                 615                 620

Gly Val Pro Gly Val Gly Gly Leu Gly Gly Ile Pro Pro Ala Ala Ala
625                 630                 635                 640

Ala Lys Ala Ala Lys Tyr Gly Ala Ala Gly Leu Gly Gly Val Leu Gly
                645                 650                 655

Gly Ala Gly Gln Phe Pro Leu Gly Gly Val Ala Ala Arg Pro Gly Phe
                660                 665                 670

Gly Leu Ser Pro Ile Phe Pro Gly Gly Ala Cys Leu Gly Lys Ala Cys
                675                 680                 685

Gly Arg Lys Arg Lys
                690

<210> SEQ ID NO 11
```

<211> LENGTH: 2082
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
ggtggcgtac caggcgcaat tcctgggggt gtcccaggcg gtgttttta tccgggcgcc      60
ggtcttggcg cactgggtgg cggtgcactg ggcccgggcg gcaaaccgct gaaaccggta     120
ccaggtggtt tagcaggcgc cggcttaggc gcaggtctgg gagcatttcc ggcagttacc     180
tttccagggg cactggttcc tggaggtgtg gccgatgcag ccgcggcata taaagccgct     240
aaagccggtg cgggtttagg aggcgtccca ggtgtcggtg gcctgggtgt tagcgccggt     300
gcagttgttc cgcagccggg agcagggggtt aaacctggta aagtgccggg agtaggtctg    360
ccaggcgttt atcctggtgg tgttttgccg ggtgcccgtt ttccgggcgt tggtgttctt     420
ccaggcgtgc cgaccggagc cggtgttaaa ccgaaagccc ccggtgttgg aggtgcattt     480
gcaggcatcc cgggagttgg cccgtttggt ggtccgcaac ctggggttcc gttaggttat     540
ccgattaaag caccgaaact gcccggcggt tatggtctgc cgtacacaac cggtaaactg     600
ccgtatggtt atggcccggg tggagttgcg ggtgcagcag gtaaagcggg ttatcctacc     660
ggaaccggtg taggtccgca ggccgctgct gccgccgccg caaaagcagc ggctaaattt     720
ggcgccggag cagcgggtgt tctgcctgga gttggtggtg cgggcgtgcc aggggtacct     780
ggtgcaattc cgggtattgg tggtattgcc ggtgtcggca ccccggccgc ggcagctgcg     840
gcagcggcgg ctgccaaagc tgctaaatac ggtgccgcgg cgggtctggt gccaggaggt     900
ccgggttttg gtccgggagt ggttggcgtg cctggcgcag gcgttcctgg tgtgggcgtt     960
ccaggtgcag ggattcctgt tgtgcctggt gccggtattc ccggcgcggc cgttccgggg    1020
gtggttagcc cggaagccgc agcgaaggct gcggcaaagg cagcaaagta tggcgcacgc    1080
ccaggagtcg gcgtgggtgg tatcccgacc tatggggtgg gcgcagggg ttttcctggt     1140
ttcggcgtag gtgtaggagg tataccgggc gtggccggtg taccagggggt tggtggcgtc    1200
cctggtgttg gcggtgtgcc aggtgttggt atttcaccgg aagcacaggc agcagccgca    1260
gctaaggcag cgaaatatgg tgccgccggc gcaggagttt taggtgggct ggttccgggc    1320
ccgcaggcag ctgtgccggg ggttccaggc accggtggtg tccctggagt cggtacgccg    1380
gcagcagcag ctaaaagcgc ggcgaaagtt gcggccaaag cccaactgcg cgccgccgcg    1440
ggcctcggtg caggtattcc ggggctgggt gtcggagttg gagtcccggg tttgggcgtg    1500
ggcgcgggag ttccgggact gggagtgggt gccggagttc ctggctttgg tgcaggcgca    1560
gatgaaggtg ttcgtcgtag cctgagtccg gaactgcgtg aaggtgatcc gagtagcagc    1620
cagcatctgc cgagcacccc gagcagcccg cgtgttccgg gtgcattagc tgcagcaaaa    1680
gccgccaagt atggtgcagc cgtgccgggc gtcttaggtg gtctgggcgc cctggtggt     1740
gtaggcattc cggagggtgt tgtgggtgca ggaccggccg ccgcagctgc ggccgccaaa    1800
gcagctgcaa aagcggccca gtttggttta gtgggcgccg caggtttagg cggtttaggt    1860
gtgggtggac tgggtgtacc tggcgtaggc ggtctgggtg gaattccgcc cgcagcggcc    1920
gcgaaagcgg caaaatatgg cgcggcaggc ctgggcggcg tgctgggtgg ggcaggtcag    1980
tttccgctgg gcggggttgc cgcacgtccg ggatttggtc tgagcccgat tttccctggc    2040
ggcgcatgtc tgggtaaagc atgtggtcgt aaacgtaaat aa                       2082
```

<210> SEQ ID NO 12
<211> LENGTH: 846
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

| | |
|---|---|
| atgaaaaaga tttggctggc gctggctggt ttagttttag cgtttagcgc atcggcggcc | 60 |
| ggtctgggtg gcgtgcctgg cgttggtggc ctgggcgtta gcgccggtgc agttgttccg | 120 |
| cagcctggtg cgggtgttaa accgggtaaa gttcctggtg ttggtctgcc tggtgtttat | 180 |
| ccaggcggtg ttctgccagg tgcgcgtttt cctggcgtgg gtgttctgcc gggtgttccg | 240 |
| accggtgcag gcgtgaaacc gaaagcacca ggtgttggtg gtgcatttgc aggtattcca | 300 |
| ggtgtgggtc cgtttggtgg tccgcagcca ggcgttccgc tgggttatcc gattaaagca | 360 |
| ccgaaactgc ctggcggtta tggtctgccg tataccaccg gtaaactgcc gtatggttat | 420 |
| ggccctggcg gtgttgccgg tgcggcaggt aaagcaggct atccgaccgg taccggtgta | 480 |
| ggtccgcagg cagcagccgc agcagcggca aaagcagcag cgaaatttgg tgcgggtgca | 540 |
| gccggtgtgc tgccaggcgt aggtggcgct ggtgtacctg gtgtccctgg cgcaattcca | 600 |
| ggtattggcg gtattgcagg cgttggtact ccggcagctg cagccgctgc cgcagccgca | 660 |
| gctaaagcag ccaaatatgg tgcagcggca ggcctggttc ctggcggtcc aggttttggt | 720 |
| ccgggtgttg ttggcgtccc aggtgccggt gtgcctggtg tgggtgttcc aggtgcgggt | 780 |
| attccggttg ttcctggcgc aggcattccg ggtgccgcag ttccgggtgt agttagcccg | 840 |
| gaataa | 846 |

<210> SEQ ID NO 13
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Met Lys Lys Ile Trp Leu Ala Leu Ala Gly Leu Val Leu Ala Phe Ser
1               5                   10                  15

Ala Ser Ala Ala Gly Leu Gly Gly Val Pro Gly Val Gly Gly Leu Gly
                20                  25                  30

Val Ser Ala Gly Ala Val Val Pro Gln Pro Gly Ala Gly Val Lys Pro
            35                  40                  45

Gly Lys Val Pro Gly Val Gly Leu Pro Gly Val Tyr Pro Gly Gly Val
        50                  55                  60

Leu Pro Gly Ala Arg Phe Pro Gly Val Gly Val Leu Pro Gly Val Pro
65                  70                  75                  80

Thr Gly Ala Gly Val Lys Pro Lys Ala Pro Gly Val Gly Gly Ala Phe
                85                  90                  95

Ala Gly Ile Pro Gly Val Gly Pro Phe Gly Gly Pro Gln Pro Gly Val
            100                 105                 110

Pro Leu Gly Tyr Pro Ile Lys Ala Pro Lys Leu Pro Gly Gly Tyr Gly
        115                 120                 125

Leu Pro Tyr Thr Thr Gly Lys Leu Pro Tyr Gly Tyr Gly Pro Gly Gly
    130                 135                 140

Val Ala Gly Ala Ala Gly Lys Ala Gly Tyr Pro Thr Gly Thr Gly Val
145                 150                 155                 160

Gly Pro Gln Ala Ala Ala Ala Ala Ala Lys Ala Ala Ala Lys Phe
                165                 170                 175

Gly Ala Gly Ala Ala Gly Val Leu Pro Gly Val Gly Gly Ala Gly Val
                180                 185                 190

Pro Gly Val Pro Gly Ala Ile Pro Gly Ile Gly Gly Ile Ala Gly Val
            195                 200                 205

Gly Thr Pro Ala Ala Ala Ala Ala Ala Ala Ala Lys Ala Ala
    210                 215                 220

Lys Tyr Gly Ala Ala Ala Gly Leu Val Pro Gly Pro Gly Phe Gly
225                 230                 235                 240

Pro Gly Val Val Gly Val Pro Gly Ala Gly Val Pro Gly Val Gly Val
            245                 250                 255

Pro Gly Ala Gly Ile Pro Val Val Pro Gly Ala Gly Ile Pro Gly Ala
            260                 265                 270

Ala Val Pro Gly Val Val Ser Pro Glu
            275                 280

<210> SEQ ID NO 14
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gccggtctgg gtggcgtgcc tggcgttggt ggcctgggcg ttagcgccgg tgcagttgtt      60
ccgcagcctg gtgcgggtgt taaaccgggt aaagttcctg gtgttggtct gcctggtgtt     120
tatccaggcg gtgttctgcc aggtgcgcgt tttcctggcg tgggtgttct gccgggtgtt     180
ccgaccggtg caggcgtgaa accgaaagca ccaggtgttg gtggtgcatt tgcaggtatt     240
ccaggtgtgg gtccgtttgg tggtccgcag ccaggcgttc cgctgggtta ccgattaaa      300 gcaccgaaac tgcctggcgg ttatggtctg ccgtatacca ccgtaaaact gccgtatggt     360
tatggccctg gcggtgttgc cggtgcggca ggtaaagcag gctatccgac cggtaccggt     420
gtaggtccgc aggcagcagc cgcagcagcg gcaaaagcag cagcgaaatt tggtgcgggt     480
gcagccggtg tgctgccagg cgtaggtggc gctggtgtac ctggtgtccc tggcgcaatt     540
ccaggtattg gcggtattgc aggcgttggt actccggcag ctgcagccgc tgccgcagcc     600
gcagctaaag cagccaaata tggtgcagcg gcaggcctgg ttcctggcgg tccaggttt      660 ggtccgggtg ttgttggcgt cccaggtgcc ggtgtgcctg gtgtgggtgt tccaggtgcg     720
ggtattccgg ttgttcctgg cgcaggcatt ccgggtgccg cagttccggg tgtagttagc     780
ccggaataa                                                              789

<210> SEQ ID NO 15
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Gly Leu Gly Gly Val Pro Gly Val Gly Gly Leu Gly Val Ser Ala
1               5                   10                  15

Gly Ala Val Val Pro Gln Pro Gly Ala Gly Val Lys Pro Gly Lys Val
            20                  25                  30

Pro Gly Val Gly Leu Pro Gly Val Tyr Pro Gly Gly Val Leu Pro Gly
            35                  40                  45

Ala Arg Phe Pro Gly Val Gly Val Leu Pro Gly Val Pro Thr Gly Ala
 50                  55                  60

Gly Val Lys Pro Lys Ala Pro Gly Val Gly Ala Phe Ala Gly Ile
 65                  70                  75                  80

Pro Gly Val Gly Pro Phe Gly Gly Pro Gln Pro Val Gly Pro Leu Gly
            85                  90                  95

Tyr Pro Ile Lys Ala Pro Lys Leu Pro Gly Gly Tyr Gly Leu Pro Tyr
            100                 105                 110

Thr Thr Gly Lys Leu Pro Tyr Gly Tyr Gly Pro Gly Val Ala Gly
            115                 120                 125

Ala Ala Gly Lys Ala Gly Tyr Pro Thr Gly Thr Gly Val Gly Pro Gln
145             130                 135                 140

Ala Ala Ala Ala Ala Ala Lys Ala Ala Lys Phe Gly Ala Gly
145                 150                 155                 160

Ala Ala Gly Val Leu Pro Gly Val Gly Gly Ala Gly Val Pro Gly Val
            165                 170                 175

Pro Gly Ala Ile Pro Gly Ile Gly Gly Ile Ala Gly Val Gly Thr Pro
            180                 185                 190

Ala Ala Ala Ala Ala Ala Ala Ala Lys Ala Ala Lys Tyr Gly
            195                 200                 205

Ala Ala Gly Leu Val Pro Gly Gly Pro Gly Phe Gly Pro Gly Val
            210                 215                 220

Val Gly Val Pro Gly Ala Gly Val Pro Gly Val Gly Val Pro Gly Ala
225                 230                 235                 240

Gly Ile Pro Val Val Pro Gly Ala Gly Ile Pro Gly Ala Ala Val Pro
            245                 250                 255

Gly Val Val Ser Pro Glu
            260

<210> SEQ ID NO 16
<211> LENGTH: 492
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgaaaaaga tttggctggc gctggctggt ttagttttag cgtttagcgc atcggcggcc      60
ggtctgggtg gcgtgcctgg cgttggtggc ctgggcgtta gcgccggtgc agttgttccg     120
cagcctggtg cgggtgttaa accgggtaaa gttcctggtg ttggtctgcc tggtgtttat     180
ccaggcggtg ttctgccagg tgcgcgtttt cctggcgtgg gtgttctgcc gggtgttccg     240
accggtgcag gcgtgaaacc gaaagcacca ggtgttggtg gtgcatttgc aggtattcca     300
ggtgtgggtc cgtttggtgg tccgcagcca ggcgttccgc tgggttatcc gattaaagca     360
ccgaaactgc ctggcggtta tggtctgccg tataccaccg gtaaactgcc gtatggttat     420
ggccctggcg tgttgccgg tgcggcaggt aaagcaggct atccgaccgg taccggtgta     480
ggtccgcagt aa                                                         492

```
<210> SEQ ID NO 17
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Lys Lys Ile Trp Leu Ala Leu Ala Gly Leu Val Leu Ala Phe Ser
1               5                   10                  15

Ala Ser Ala Ala Gly Leu Gly Gly Val Pro Gly Val Gly Leu Gly
            20                  25                  30

Val Ser Ala Gly Ala Val Val Pro Gln Pro Gly Ala Gly Val Lys Pro
        35                  40                  45

Gly Lys Val Pro Gly Val Gly Leu Pro Gly Val Tyr Pro Gly Gly Val
    50                  55                  60

Leu Pro Gly Ala Arg Phe Pro Gly Val Gly Val Leu Pro Gly Val Pro
65                  70                  75                  80

Thr Gly Ala Gly Val Lys Pro Lys Ala Pro Gly Val Gly Gly Ala Phe
                85                  90                  95

Ala Gly Ile Pro Gly Val Gly Pro Phe Gly Pro Gln Pro Gly Val
            100                 105                 110

Pro Leu Gly Tyr Pro Ile Lys Ala Pro Lys Leu Pro Gly Gly Tyr Gly
        115                 120                 125

Leu Pro Tyr Thr Thr Gly Lys Leu Pro Tyr Gly Tyr Pro Gly Gly
    130                 135                 140

Val Ala Gly Ala Ala Gly Lys Ala Gly Tyr Pro Thr Gly Thr Gly Val
145                 150                 155                 160

Gly Pro Gln

<210> SEQ ID NO 18
<211> LENGTH: 435
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gccggtctgg gtggcgtgcc tggcgttggt ggcctgggcg ttagcgccgg tgcagttgtt       60
ccgcagcctg gtgcgggtgt taaaccgggt aaagttcctg gtgttggtct gcctggtgtt      120
tatccaggcg gtgttctgcc aggtgcgcgt tttcctggcg tgggtgttct gccgggtgtt      180
ccgaccggtg caggcgtgaa accgaaagca ccaggtgttg gtggtgcatt tgcaggtatt      240
ccaggtgtgg gtccgtttgg tggtccgcag ccaggcgttc gctgggtta tccgattaaa       300 gcaccgaaac tgcctggcgg ttatggtctg ccgtatacca ccggtaaact gccgtatggt      360
tatggccctg gcggtgttgc cggtgcggca ggtaaagcag gctatccgac cggtaccggt      420
gtaggtccgc agtaa                                                        435

<210> SEQ ID NO 19
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19
```

-continued

```
Ala Gly Leu Gly Gly Val Pro Gly Val Gly Leu Gly Val Ser Ala
1               5                   10                  15

Gly Ala Val Val Pro Gln Pro Gly Ala Gly Val Lys Pro Gly Lys Val
            20                  25                  30

Pro Gly Val Gly Leu Pro Gly Val Tyr Pro Gly Val Leu Pro Gly
            35                  40                  45

Ala Arg Phe Pro Gly Val Gly Val Leu Pro Gly Val Pro Thr Gly Ala
50                  55                  60

Gly Val Lys Pro Lys Ala Pro Gly Val Gly Gly Ala Phe Ala Gly Ile
65              70                  75                  80

Pro Gly Val Gly Pro Phe Gly Gly Pro Gln Pro Gly Val Pro Leu Gly
            85                  90                  95

Tyr Pro Ile Lys Ala Pro Lys Leu Pro Gly Gly Tyr Gly Leu Pro Tyr
            100                 105                 110

Thr Thr Gly Lys Leu Pro Tyr Gly Tyr Gly Pro Gly Gly Val Ala Gly
            115                 120                 125

Ala Ala Gly Lys Ala Gly Tyr Pro Thr Gly Thr Gly Val Gly Pro Gln
            130                 135                 140

<210> SEQ ID NO 20
<211> LENGTH: 760
<212> TYPE: PRT
<213> ORGANISM: Homo sapiens

<400> SEQUENCE: 20

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
                20                  25                  30

Gly Gly Lys Pro Leu Lys Pro Val Pro Gly Gly Leu Ala Gly Ala Gly
                35                  40                  45

Leu Gly Ala Gly Leu Gly Ala Phe Pro Ala Val Thr Phe Pro Gly Ala
50                  55                  60

Leu Val Pro Gly Gly Val Ala Asp Ala Ala Ala Ala Tyr Lys Ala Ala
65              70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
                100                 105                 110

Gly Lys Val Pro Gly Val Gly Leu Pro Gly Val Tyr Pro Gly Gly Val
                115                 120                 125

Leu Pro Gly Ala Arg Phe Pro Gly Val Gly Val Leu Pro Gly Val Pro
            130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
            195                 200                 205

Val Ala Gly Ala Ala Gly Lys Ala Gly Tyr Pro Thr Gly Thr Gly Val
            210                 215                 220

Gly Pro Gln Ala Ala Ala Ala Ala Ala Ala Ala Lys Ala Ala Ala Lys Phe
```

```
                225                 230                 235                 240
        Gly Ala Gly Ala Ala Gly Val Leu Pro Gly Val Gly Ala Gly Val
                        245                 250                 255

Pro Gly Val Pro Gly Ala Ile Pro Gly Ile Gly Ile Ala Gly Val
                        260                 265                 270

Gly Thr Pro Ala Ala Ala Ala Ala Ala Ala Ala Lys Ala Ala
                        275                 280                 285

Lys Tyr Gly Ala Ala Ala Gly Leu Val Pro Gly Pro Gly Phe Gly
                        290                 295                 300

Pro Gly Val Val Gly Val Pro Gly Ala Gly Val Pro Gly Val Gly Val
        305                 310                 315                 320

Pro Gly Ala Gly Ile Pro Val Val Pro Gly Ala Gly Ile Pro Gly Ala
                        325                 330                 335

Ala Val Pro Gly Val Val Ser Pro Glu Ala Ala Lys Ala Ala
                        340                 345                 350

Lys Ala Ala Lys Tyr Gly Ala Arg Pro Gly Val Gly Val Gly Gly Ile
                        355                 360                 365

Pro Thr Tyr Gly Val Gly Ala Gly Gly Phe Pro Gly Phe Gly Val Gly
                        370                 375                 380

Val Gly Gly Ile Pro Gly Val Ala Gly Val Pro Gly Val Gly Gly Val
        385                 390                 395                 400

Pro Gly Val Gly Gly Val Pro Gly Val Gly Ile Ser Pro Glu Ala Gln
                        405                 410                 415

Ala Ala Ala Ala Ala Lys Ala Ala Lys Tyr Gly Ala Ala Gly Ala Gly
                        420                 425                 430

Val Leu Gly Gly Leu Val Pro Gly Pro Gln Ala Ala Val Pro Gly Val
                        435                 440                 445

Pro Gly Thr Gly Gly Val Pro Gly Val Gly Thr Pro Ala Ala Ala Ala
                        450                 455                 460

Ala Lys Ala Ala Ala Lys Ala Ala Gln Phe Gly Leu Val Pro Gly Val
        465                 470                 475                 480

Gly Val Ala Pro Gly Val Gly Val Ala Pro Gly Val Gly Val Ala Pro
                        485                 490                 495

Gly Val Gly Leu Ala Pro Gly Val Gly Val Ala Pro Gly Val Gly Val
                        500                 505                 510

Ala Pro Gly Val Gly Val Ala Pro Gly Ile Gly Pro Gly Gly Val Ala
                        515                 520                 525

Ala Ala Ala Lys Ser Ala Ala Lys Val Ala Ala Lys Ala Gln Leu Arg
        530                 535                 540

Ala Ala Ala Gly Leu Gly Ala Gly Ile Pro Gly Leu Gly Val Gly Val
        545                 550                 555                 560

Gly Val Pro Gly Leu Gly Val Gly Ala Gly Val Pro Gly Leu Gly Val
                        565                 570                 575

Gly Ala Gly Val Pro Gly Phe Gly Ala Gly Ala Asp Glu Gly Val Arg
                        580                 585                 590

Arg Ser Leu Ser Pro Glu Leu Arg Glu Gly Asp Pro Ser Ser Ser Gln
                        595                 600                 605

His Leu Pro Ser Thr Pro Ser Ser Pro Arg Val Pro Gly Ala Leu Ala
                        610                 615                 620

Ala Ala Lys Ala Ala Lys Tyr Gly Ala Ala Val Pro Gly Val Leu Gly
        625                 630                 635                 640

Gly Leu Gly Ala Leu Gly Gly Val Gly Ile Pro Gly Gly Val Val Gly
                        645                 650                 655
```

```
Ala Gly Pro Ala Ala Ala Ala Ala Lys Ala Ala Lys Ala
            660                 665                 670

Ala Gln Phe Gly Leu Val Gly Ala Ala Gly Leu Gly Gly Leu Gly Val
        675                 680                 685

Gly Gly Leu Gly Val Pro Gly Val Gly Leu Gly Gly Ile Pro Pro
690                 695                 700

Ala Ala Ala Lys Ala Ala Lys Tyr Gly Ala Ala Gly Leu Gly Gly
705                 710                 715                 720

Val Leu Gly Gly Ala Gly Gln Phe Pro Leu Gly Gly Val Ala Ala Arg
                725                 730                 735

Pro Gly Phe Gly Leu Ser Pro Ile Phe Pro Gly Gly Ala Cys Leu Gly
            740                 745                 750

Lys Ala Cys Gly Arg Lys Arg Lys
            755                 760

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 2-30 residues

<400> SEQUENCE: 21

His His His His His His His His His His His His His His His
1               5                   10                  15

His His His His His His His His His His His His His His His
                20                  25                  30

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MISC_FEATURE
<222> LOCATION: (1)..(20)
<223> OTHER INFORMATION: This sequence may encompass 2-20 residues

<400> SEQUENCE: 22

His His His His His His His His His His His His His His His His
1               5                   10                  15

His His His His
            20

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 23
```

His His His His His His His His His His His His His His His His
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(18)
<223> OTHER INFORMATION: This sequence may encompass 5-18 residues

<400> SEQUENCE: 24

His His His His His His His His His His His His His His His His
1               5                   10                  15

His His

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 5-16 residues

<400> SEQUENCE: 25

His His His His His His His His His His His His His His His His
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 26

His His His His His His His His His His His His His His His
1               5                   10                  15

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MISC_FEATURE
<222> LOCATION: (1)..(14)
<223> OTHER INFORMATION: This sequence may encompass 5-14 residues

<400> SEQUENCE: 27

His His His His His His His His His His His His His His
1               5                   10

<210> SEQ ID NO 28

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(13)
<223> OTHER INFORMATION: This sequence may encompass 5-13 residues

<400> SEQUENCE: 28

His His His His His His His His His His His His His
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: This sequence may encompass 5-12 residues

<400> SEQUENCE: 29

His His His His His His His His His His His His
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(11)
<223> OTHER INFORMATION: This sequence may encompass 5-11 residues

<400> SEQUENCE: 30

His His His His His His His His His His His
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 31

His His His His His His His His His His
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MISC_FEATURE
<222> LOCATION: (1)..(12)
<223> OTHER INFORMATION: This sequence may encompass 6-12 residues

<400> SEQUENCE: 32

His His His His His His His His His His His His
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(11)
<223> OTHER INFORMATION: This sequence may encompass 6-11 residues

<400> SEQUENCE: 33

His His His His His His His His His His His
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 7-10 residues

<400> SEQUENCE: 34

His His His His His His His His His His
1               5                   10
```